(12) United States Patent
Landry et al.

(10) Patent No.: US 7,637,952 B2
(45) Date of Patent: Dec. 29, 2009

(54) INSTRUMENTATION AND PROCEDURE FOR IMPLANTING SPINAL IMPLANT DEVICES

(75) Inventors: Michael E. Landry, Austin, TX (US); Ronald C. Todd, Austin, TX (US); Erik J. Wagner, Austin, TX (US); Stephen H. Hochschuler, Scottsdale, AZ (US)

(73) Assignee: Zimmer Spine, Inc., Minneapolis, MN (US)

(*) Notice: Subject to any disclaimer, the term of this patent is extended or adjusted under 35 U.S.C. 154(b) by 4 days.

(21) Appl. No.: 10/387,329

(22) Filed: Mar. 11, 2003

(65) Prior Publication Data

US 2003/0233145 A1  Dec. 18, 2003

Related U.S. Application Data

(60) Provisional application No. 60/363,219, filed on Mar. 11, 2002.

(51) Int. Cl.
  *A61F 2/44* (2006.01)
  *A61F 2/00* (2006.01)

(52) U.S. Cl. .............. 623/17.11; 606/90; 606/100; 623/17.16

(58) Field of Classification Search ........... 606/90, 606/99, 61, 205, 105, 206, 102, 72, 85, 100, 606/86; 623/17.11, 17.16
See application file for complete search history.

(56) References Cited

U.S. PATENT DOCUMENTS

| 3,486,505 | A | * | 12/1969 | Morrison ............... 606/90 |
| 4,388,921 | A | | 6/1983 | Sutter et al. |
| 4,401,112 | A | | 8/1983 | Rezaian |
| 4,433,677 | A | | 2/1984 | Ulrich et al. |
| 4,492,226 | A | | 1/1985 | Belykh et al. |
| 4,501,269 | A | | 2/1985 | Bagby |
| 4,503,848 | A | | 3/1985 | Caspar et al. |
| 4,570,618 | A | | 2/1986 | Wu |
| 4,604,995 | A | | 8/1986 | Stephens et al. |
| 4,641,636 | A | | 2/1987 | Cotrel |
| 4,643,178 | A | | 2/1987 | Nastari et al. |

(Continued)

FOREIGN PATENT DOCUMENTS

DE  4323956  10/1994

(Continued)

OTHER PUBLICATIONS

Danek Group, Inc. Medical Division Publication entitled, "TSRH Spinal System—Unmatched versatility," 1992, pp. 1-4.

(Continued)

*Primary Examiner*—Pedro Philogene
(74) *Attorney, Agent, or Firm*—Sprinkle IP Law Group

(57) ABSTRACT

An instrumentation set may include insertion instruments for forming an implant between bone structures. The insertion instruments may include a spreader and a separator. The bone structures may be vertebrae. Implant members may be attached to the spreader and positioned between the bone structures. The separator may be inserted into the spreader to establish a desired separation distance between the implant members. Connectors may be inserted into the implant members to join the implant members together and form the implant. The insertion instruments may be removed. A seater may be used to set the position of the connectors relative to the implant members to inhibit disassembly of the implant.

17 Claims, 46 Drawing Sheets

U.S. PATENT DOCUMENTS

| | | |
|---|---|---|
| 4,697,586 A | 10/1987 | Gazale |
| 4,714,469 A * | 12/1987 | Kenna .................. 606/61 |
| 4,743,256 A | 5/1988 | Brantigan |
| 4,763,644 A | 8/1988 | Webb |
| 4,805,602 A | 2/1989 | Puno et al. |
| 4,834,757 A | 5/1989 | Brantigan |
| 4,863,476 A | 9/1989 | Shepperd |
| 4,878,915 A | 11/1989 | Brantigan |
| 4,887,596 A | 12/1989 | Sherman |
| 4,946,458 A | 8/1990 | Harms et al. |
| 4,950,269 A | 8/1990 | Gaines, Jr. |
| 4,961,740 A | 10/1990 | Ray et al. |
| 4,966,600 A | 10/1990 | Songer et al. |
| 4,987,892 A | 1/1991 | Krag et al. |
| 5,005,562 A | 4/1991 | Cotrel |
| 5,026,373 A | 6/1991 | Ray et al. |
| 5,047,029 A | 9/1991 | Aebi et al. |
| 5,055,104 A | 10/1991 | Ray |
| 5,074,864 A | 12/1991 | Cozad et al. |
| 5,102,412 A | 4/1992 | Rogozinski |
| 5,108,399 A | 4/1992 | Eitenmuller et al. |
| 5,108,446 A | 4/1992 | Wagner et al. |
| 5,116,340 A | 5/1992 | Songer et al. |
| 5,123,926 A | 6/1992 | Pisharodi |
| 5,127,912 A | 7/1992 | Ray et al. |
| 5,129,388 A | 7/1992 | Vignaud et al. |
| 5,129,904 A | 7/1992 | Illi |
| 5,147,359 A | 9/1992 | Cozad et al. |
| 5,154,718 A | 10/1992 | Cozad et al. |
| 5,171,278 A | 12/1992 | Pisharodi |
| 5,176,678 A | 1/1993 | Tsou |
| 5,176,680 A | 1/1993 | Vignaud et al. |
| 5,181,917 A | 1/1993 | Rogozinski |
| 5,192,321 A | 3/1993 | Strokon |
| 5,192,327 A | 3/1993 | Brantigan |
| 5,201,734 A | 4/1993 | Cozad et al. |
| 5,242,445 A | 9/1993 | Ashman |
| 5,242,448 A | 9/1993 | Pettine et al. |
| 5,246,442 A | 9/1993 | Ashman et al. |
| 5,261,909 A | 11/1993 | Sutterlin et al. |
| 5,263,953 A | 11/1993 | Bagby |
| 5,281,222 A | 1/1994 | Allard et al. |
| 5,282,801 A | 2/1994 | Sherman |
| 5,290,312 A | 3/1994 | Kojimoto et al. |
| 5,290,494 A | 3/1994 | Coombes et al. |
| 5,303,718 A | 4/1994 | Krajicek |
| 5,304,179 A | 4/1994 | Wagner |
| 5,306,307 A | 4/1994 | Senter et al. |
| 5,306,309 A | 4/1994 | Wagner et al. |
| 5,312,405 A | 5/1994 | Korotko et al. |
| 5,312,410 A | 5/1994 | Miller et al. |
| 5,318,566 A | 6/1994 | Miller |
| 5,336,223 A | 8/1994 | Rogers |
| 5,336,240 A | 8/1994 | Metzler et al. |
| 5,344,422 A | 9/1994 | Frigg |
| 5,348,026 A | 9/1994 | Davidson |
| 5,357,983 A | 10/1994 | Mathews |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,370,697 A | 12/1994 | Baumgartner |
| 5,380,325 A | 1/1995 | Lahille et al. |
| 5,385,583 A | 1/1995 | Cotrel |
| 5,390,683 A | 2/1995 | Pisharodi |
| 5,395,374 A | 3/1995 | Miller et al. |
| 5,397,364 A | 3/1995 | Kozak et al. |
| 5,403,315 A | 4/1995 | Ashman |
| 5,405,391 A | 4/1995 | Hednerson et al. |
| 5,415,658 A | 5/1995 | Kilpela et al. |
| 5,417,690 A | 5/1995 | Sennett et al. |
| 5,423,820 A | 6/1995 | Miller et al. |
| 5,423,825 A | 6/1995 | Levine |
| 5,425,772 A | 6/1995 | Brantigan |
| 5,429,863 A | 7/1995 | McMillin |
| 5,431,658 A | 7/1995 | Moskovich |
| 5,443,514 A | 8/1995 | Steffee |
| 5,458,642 A | 10/1995 | Beer et al. |
| 5,466,237 A | 11/1995 | Byrd, III et al. |
| 5,474,555 A | 12/1995 | Puno et al. |
| 5,480,437 A | 1/1996 | Draenert |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland et al. |
| 5,505,732 A | 4/1996 | Michelson |
| 5,507,746 A | 4/1996 | Lin |
| 5,514,180 A | 5/1996 | Heggeness et al. |
| 5,520,690 A | 5/1996 | Errico et al. |
| 5,522,899 A | 6/1996 | Michelson |
| 5,527,341 A | 6/1996 | Gogolewski et al. |
| 5,531,746 A | 7/1996 | Errico et al. |
| 5,531,751 A | 7/1996 | Schultheiss et al. |
| 5,536,270 A | 7/1996 | Songer et al. |
| 5,536,271 A | 7/1996 | Daly et al. |
| 5,545,165 A | 8/1996 | Biedermann et al. |
| 5,549,608 A | 8/1996 | Errico et al. |
| 5,549,612 A | 8/1996 | Yapp et al. |
| 5,554,157 A | 9/1996 | Errico et al. |
| 5,554,191 A | 9/1996 | Lahille et al. |
| 5,563,124 A | 10/1996 | Damien et al. |
| 5,569,248 A | 10/1996 | Mathews |
| 5,569,253 A | 10/1996 | Farris et al. |
| 5,571,192 A | 11/1996 | Schonhoffer |
| 5,575,792 A | 11/1996 | Errico et al. |
| 5,578,033 A | 11/1996 | Errico et al. |
| 5,578,034 A | 11/1996 | Estes |
| 5,584,834 A | 12/1996 | Errico et al. |
| 5,586,984 A | 12/1996 | Errico et al. |
| 5,591,235 A | 1/1997 | Kuslich |
| 5,593,409 A | 1/1997 | Michelson |
| 5,601,553 A | 2/1997 | Trebing et al. |
| 5,601,556 A | 2/1997 | Pisharodi |
| 5,603,713 A | 2/1997 | Aust et al. |
| 5,607,424 A | 3/1997 | Tropiano |
| 5,607,425 A | 3/1997 | Rogozinski |
| 5,607,426 A | 3/1997 | Ralph et al. |
| 5,607,428 A | 3/1997 | Lin |
| 5,607,430 A | 3/1997 | Bailey |
| 5,609,592 A | 3/1997 | Brumfield et al. |
| 5,609,593 A | 3/1997 | Errico et al. |
| 5,609,594 A | 3/1997 | Errico et al. |
| 5,609,596 A | 3/1997 | Pepper |
| 5,609,635 A | 3/1997 | Michelson |
| 5,609,636 A | 3/1997 | Kohrs et al. |
| 5,611,800 A | 3/1997 | Davis et al. |
| 5,611,801 A | 3/1997 | Songer |
| 5,613,967 A | 3/1997 | Engelhardt et al. |
| 5,616,144 A | 4/1997 | Yapp et al. |
| 5,620,443 A | 4/1997 | Gertzbein et al. |
| 5,624,441 A | 4/1997 | Sherman et al. |
| 5,626,579 A | 5/1997 | Muschler et al. |
| 5,628,740 A | 5/1997 | Mullane |
| 5,628,756 A | 5/1997 | Barker, Jr. et al. |
| 5,630,816 A | 5/1997 | Kambin |
| 5,632,747 A | 5/1997 | Scarborough et al. |
| 5,634,925 A | 6/1997 | Urbanski |
| 5,643,260 A | 7/1997 | Doherty |
| 5,643,264 A | 7/1997 | Sherman et al. |
| 5,643,265 A | 7/1997 | Errico et al. |
| 5,645,084 A | 7/1997 | McKay |
| 5,645,544 A | 7/1997 | Tai et al. |
| 5,645,549 A | 7/1997 | Boyd et al. |
| 5,645,598 A | 7/1997 | Brosnahan, III |

| Patent | Date | Inventor |
|---|---|---|
| 5,647,873 A | 7/1997 | Errico et al. |
| 5,649,927 A | 7/1997 | Kilpela et al. |
| 5,651,283 A | 7/1997 | Runciman et al. |
| 5,651,789 A | 7/1997 | Cotrel |
| 5,653,708 A | 8/1997 | Howland |
| 5,653,709 A | 8/1997 | Frigg |
| 5,653,763 A | 8/1997 | Errico et al. |
| 5,658,289 A | 8/1997 | Boucher et al. |
| 5,658,335 A | 8/1997 | Allen |
| 5,658,337 A | 8/1997 | Kohrs et al. |
| 5,658,516 A | 8/1997 | Eppley et al. |
| 5,662,653 A | 9/1997 | Songer et al. |
| 5,665,088 A | 9/1997 | Gil et al. |
| 5,665,112 A | 9/1997 | Thal |
| 5,665,122 A | 9/1997 | Kambin |
| 5,667,506 A | 9/1997 | Sutterlin |
| 5,667,507 A | 9/1997 | Corin et al. |
| 5,667,508 A | 9/1997 | Errico et al. |
| 5,668,288 A | 9/1997 | Storey et al. |
| 5,669,909 A | 9/1997 | Zdeblick et al. |
| 5,669,910 A | 9/1997 | Korhonen et al. |
| 5,669,911 A | 9/1997 | Errico et al. |
| 5,671,695 A | 9/1997 | Schroeder |
| 5,672,175 A | 9/1997 | Martin |
| 5,672,176 A | 9/1997 | Biedermann et al. |
| 5,674,222 A | 10/1997 | Berger et al. |
| 5,674,295 A | 10/1997 | Ray et al. |
| 5,674,296 A | 10/1997 | Bryan et al. |
| 5,676,665 A | 10/1997 | Bryan |
| 5,676,666 A | 10/1997 | Oxland et al. |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,683,391 A | 11/1997 | Boyd |
| 5,683,392 A | 11/1997 | Richelsoph et al. |
| 5,683,393 A | 11/1997 | Ralph |
| 5,683,394 A | 11/1997 | Rinner |
| 5,688,272 A | 11/1997 | Montague et al. |
| 5,688,273 A | 11/1997 | Errico et al. |
| 5,688,274 A | 11/1997 | Errico et al. |
| 5,688,279 A | 11/1997 | McNulty et al. |
| 5,688,280 A | 11/1997 | Booth, Jr. et al. |
| 5,690,629 A | 11/1997 | Asher et al. |
| 5,690,630 A | 11/1997 | Errico et al. |
| 5,690,631 A | 11/1997 | Duncan et al. |
| 5,690,632 A | 11/1997 | Schwartz et al. |
| 5,690,633 A | 11/1997 | Taylor et al. |
| 5,690,842 A | 11/1997 | Panchison |
| 5,693,046 A | 12/1997 | Songer et al. |
| 5,693,053 A | 12/1997 | Estes |
| 5,693,100 A | 12/1997 | Pisharodi |
| 5,697,929 A | 12/1997 | Mellinger |
| 5,697,977 A | 12/1997 | Pisharodi |
| 5,700,291 A | 12/1997 | Kuslich et al. |
| 5,700,292 A | 12/1997 | Margulies |
| 5,702,391 A | 12/1997 | Lin |
| 5,702,392 A | 12/1997 | Wu et al. |
| 5,702,393 A | 12/1997 | Pfaifer |
| 5,702,394 A | 12/1997 | Henry et al. |
| 5,702,395 A | 12/1997 | Hopf |
| 5,702,396 A | 12/1997 | Hoenig et al. |
| 5,702,399 A | 12/1997 | Kilpela et al. |
| 5,702,449 A | 12/1997 | McKay |
| 5,702,450 A | 12/1997 | Bisserie |
| 5,702,451 A | 12/1997 | Biedermann et al. |
| 5,702,452 A | 12/1997 | Argenson et al. |
| 5,702,453 A | 12/1997 | Rabbe et al. |
| 5,702,454 A | 12/1997 | Baumgartner |
| 5,702,455 A | 12/1997 | Saggar |
| 5,704,936 A | 1/1998 | Mazel |
| 5,704,937 A | 1/1998 | Martin |
| 5,707,372 A | 1/1998 | Errico et al. |
| 5,707,395 A | 1/1998 | Li |
| 5,709,681 A | 1/1998 | Pennig |
| 5,709,682 A | 1/1998 | Medoff |
| 5,709,683 A | 1/1998 | Bagby |
| 5,709,684 A | 1/1998 | Errico et al. |
| 5,709,685 A | 1/1998 | Dombrowski et al. |
| 5,709,686 A | 1/1998 | Talos et al. |
| 5,713,841 A | 2/1998 | Graham |
| 5,713,898 A | 2/1998 | Stucker et al. |
| 5,713,899 A | 2/1998 | Marnay et al. |
| 5,713,900 A | 2/1998 | Benzel et al. |
| 5,713,903 A | 2/1998 | Sander et al. |
| 5,713,904 A | 2/1998 | Errico et al. |
| 5,716,355 A | 2/1998 | Jackson |
| 5,716,356 A | 2/1998 | Biedermann et al. |
| 5,716,357 A | 2/1998 | Rogozinski |
| 5,716,358 A | 2/1998 | Ochoa et al. |
| 5,716,359 A | 2/1998 | Ojima et al. |
| 5,716,415 A | 2/1998 | Steffee |
| 5,716,416 A | 2/1998 | Lin |
| 5,720,746 A | 2/1998 | Soubeiran |
| 5,720,747 A | 2/1998 | Burke |
| 5,720,748 A | 2/1998 | Kuslich et al. |
| 5,720,751 A | 2/1998 | Jackson |
| 5,722,977 A | 3/1998 | Wilhelmy |
| 5,749,916 A | 5/1998 | Richelsoph |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,785,710 A | 7/1998 | Michelson |
| 5,797,909 A | 8/1998 | Michelson |
| 5,800,550 A | 9/1998 | Sertich |
| 5,814,084 A | 9/1998 | Grivas et al. |
| 5,860,973 A | 1/1999 | Michelson |
| 5,865,847 A | 2/1999 | Kohrs et al. |
| 5,876,457 A | 3/1999 | Picha et al. |
| 5,888,227 A | 3/1999 | Cottle |
| 5,895,427 A | 4/1999 | Kuslich et al. |
| 5,897,556 A | 4/1999 | Drewry et al. |
| 5,897,593 A | 4/1999 | Kohrs et al. |
| 5,916,267 A | 6/1999 | Tienboon |
| 5,947,971 A | 9/1999 | Kuslich et al. |
| 5,961,554 A | 10/1999 | Janson et al. |
| 5,980,522 A | 11/1999 | Koros et al. |
| 5,984,922 A | 11/1999 | McKay |
| 6,030,635 A | 2/2000 | Gertzman et al. |
| 6,033,438 A | 3/2000 | Bianchi et al. |
| 6,045,579 A | 4/2000 | Hochschuler et al. |
| 6,080,193 A | 6/2000 | Hochschuler et al. |
| 6,083,225 A | 7/2000 | Winslow et al. |
| 6,090,143 A | 7/2000 | Meriwether et al. |
| 6,096,044 A | 8/2000 | Boyd et al. |
| 6,099,527 A | 8/2000 | Hochschuler et al. |
| 6,102,950 A * | 8/2000 | Vaccaro .................. 623/17.16 |
| 6,113,602 A | 9/2000 | Sand |
| 6,113,638 A | 9/2000 | Williams et al. |
| 6,123,705 A | 9/2000 | Michelson |
| 6,139,551 A | 10/2000 | Michelson et al. |
| 6,146,420 A | 11/2000 | McKay |
| 6,149,651 A | 11/2000 | Drewry et al. |
| 6,156,037 A | 12/2000 | LeHuec et al. |
| 6,159,215 A * | 12/2000 | Urbahns et al. ................ 606/86 |
| 6,174,311 B1 | 1/2001 | Branch et al. |
| 6,176,882 B1 | 1/2001 | Biedermann et al. |
| 6,183,517 B1 | 2/2001 | Suddaby |
| 6,190,414 B1 | 2/2001 | Young et al. |
| 6,193,757 B1 * | 2/2001 | Foley et al. ............. 623/17.16 |
| 6,197,033 B1 | 3/2001 | Haid, Jr. et al. |
| 6,200,322 B1 | 3/2001 | Branch et al. |
| 6,206,922 B1 | 3/2001 | Zdeblick et al. |
| 6,210,412 B1 | 4/2001 | Michelson |
| 6,224,595 B1 | 5/2001 | Michelson |

| | | |
|---|---|---|
| 6,224,607 B1 | 5/2001 | Michelson |
| 6,224,631 B1 | 5/2001 | Kohrs |
| 6,241,729 B1 | 6/2001 | Estes et al. |
| 6,241,770 B1 | 6/2001 | Michelson |
| 6,245,072 B1 | 6/2001 | Zdeblick et al. |
| 6,245,108 B1 | 6/2001 | Biscup |
| 6,251,140 B1 | 6/2001 | Marino et al. |
| 6,261,296 B1 * | 7/2001 | Aebi et al. ............. 606/90 |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Houfburg |
| 6,287,343 B1 | 9/2001 | Kuslich et al. |
| 6,290,724 B1 | 9/2001 | Marino |
| 6,296,665 B1 | 10/2001 | Strnad et al. |
| 6,302,914 B1 | 10/2001 | Michelson |
| 6,309,421 B1 | 10/2001 | Pisharodi |
| 6,325,827 B1 | 12/2001 | Lin |
| 6,342,074 B1 | 1/2002 | Simpson |
| 6,346,122 B1 | 2/2002 | Picha et al. |
| 6,371,986 B1 | 4/2002 | Bagby |
| 6,371,989 B1 | 4/2002 | Chauvin et al. |
| 6,375,655 B1 | 4/2002 | Zdeblick et al. |
| 6,387,130 B1 | 5/2002 | Stone et al. |
| 6,409,766 B1 | 6/2002 | Brett |
| 6,416,515 B1 | 7/2002 | Wagner |
| 6,419,705 B1 | 7/2002 | Erickson |
| 6,423,095 B1 | 7/2002 | Van Hoeck et al. |
| 6,428,541 B1 | 8/2002 | Boyd et al. |
| 6,432,106 B1 | 8/2002 | Fraser |
| 6,432,107 B1 | 8/2002 | Ferree |
| 6,436,098 B1 | 8/2002 | Michelson |
| 6,447,544 B1 | 9/2002 | Michelson |
| 6,447,545 B1 | 9/2002 | Bagby |
| 6,447,547 B1 | 9/2002 | Michelson |
| 6,454,806 B1 | 9/2002 | Cohen et al. |
| 6,458,159 B1 | 10/2002 | Thalgott |
| 6,461,359 B1 | 10/2002 | Tribus et al. |
| 6,468,276 B1 | 10/2002 | McKay |
| 6,471,724 B2 | 10/2002 | Zdeblick et al. |
| 6,478,800 B1 * | 11/2002 | Fraser et al. ............. 606/99 |
| 6,478,823 B1 | 11/2002 | Michelson |
| 6,482,233 B1 | 11/2002 | Aebi et al. |
| 6,485,517 B1 | 11/2002 | Michelson |
| 6,491,724 B1 | 12/2002 | Ferree |
| 6,500,205 B1 | 12/2002 | Michelson |
| 6,517,544 B1 | 2/2003 | Michelson |
| 6,520,967 B1 * | 2/2003 | Cauthen ............. 606/99 |
| 6,520,993 B2 | 2/2003 | James et al. |
| 6,524,318 B1 | 2/2003 | Longhini et al. |
| 6,562,074 B2 | 5/2003 | Gerbec et al. |
| 6,576,016 B1 | 6/2003 | Hochshuler et al. |
| 6,610,093 B1 | 8/2003 | Pisharodi |
| 6,641,614 B1 | 11/2003 | Wagner et al. |
| 6,648,917 B2 * | 11/2003 | Gerbec et al. ............. 623/17.11 |
| 6,652,533 B2 * | 11/2003 | O'Neil ............. 606/100 |
| 6,706,070 B1 | 3/2004 | Wagner et al. |
| 6,716,218 B2 * | 4/2004 | Holmes et al. ............. 606/105 |
| 6,726,720 B2 | 4/2004 | Ross et al. |
| 6,764,491 B2 * | 7/2004 | Frey et al. ............. 606/85 |
| 6,852,129 B2 | 2/2005 | Gerbec et al. |
| 6,893,464 B2 | 5/2005 | Kiester |

FOREIGN PATENT DOCUMENTS

| | | |
|---|---|---|
| EP | 0260044 | 3/1988 |
| EP | 0578320 | 1/1994 |
| EP | 0778007 | 6/1997 |
| EP | 1 306 064 A1 | 5/2003 |
| EP | 1306064 * | 5/2003 |
| FR | 2717068 | 9/1995 |
| FR | 2732887 | 10/1996 |
| FR | 2736535 | 1/1997 |
| SU | 1424826 | 9/1988 |
| WO | 88/03781 | 6/1988 |
| WO | WO 9510248 A1 | 4/1995 |
| WO | 97/00054 | 1/1997 |
| WO | 97/06753 | 2/1997 |
| WO | 98/14142 | 4/1998 |
| WO | 01/19295 | 3/2001 |
| WO | WO 0209626 A1 | 7/2002 |
| WO | WO/2003/077808 | 9/2003 |

OTHER PUBLICATIONS

Dickman Curtis A., et al., BNI Quarterly Publication entitled, "Techniques of Screw Fixation of the Cervical Spine," vol. 9. No. 4, Fall 1993, pp. 27-39.

Slone et al., RadioGraphics Publication entitled, "Spinal Fixation," vol. 13 No. 2, Mar. 1993, pp. 341-356.

Synthes Spine Publication entitled, "The Universal Spinal System—Internal Fixation for the Spine," 1994, pp. 1-15.

AcroMed Publication entitled, "The ISOLA Spinal System—Versatility, simplicity and minimal profile in the surgical treatment of the spine," 1994, pp. 1-15.

Danek Publication entitled, "AXIS—Fixation System," 1993, pp. 1-6.

Synthes Publication entitled, "Small Notched Titanium Reconstruction Plate System," 1996, pp. 1-6.

J. Neurosurg Publication entitled, "Posterior plates in the management of cervical instability: long-term results in 44 patients," vol. 81, 1994, pp. 341-349.

BNI Quarterly Publication entitled, "Lateral Mass Posterior Plating and Facet Fusion for Cervical Spine Instability," vol. 7, No. 2, 1991, pp. i,ii, 1-12.

AcroMed Publication entitled, "AcroMed Spinal Solutions for Cervical Pathologies," 7-95, pp. 1-8.

Huhn, Stephen L. et al., "Posterior Spinal Osteosynthesis for Cervical Fracture/Dislocation Using a Flexible Multistrand Cable System: Technical Note," Neurosurgery, vol. 29, No. 6, 1991, pp. 943-946.

Dickman, Curtis A. et al., "Wire Fixation for the Cervical Spine: Biomechanical Principles and Surgical Techniques," BNI Quarterly, vol. 9, No. 4, Fall 1993, pp. 2-16.

Publication by AcroMed entitled, "ACROMED Cable System by Songer," Sep. 1993, 4 pp.

M. Aebi, MD, et al., "Treatment of Cervical Spine Injuries with Anterior Plating: Indications, Techniques, and Results," vol. 16, No. 3S, Mar. 1991 Supplement, pp. S38-S45.

Foley, M.D. et al., "Aline Anterior Cervical Plating System," Smith & Nephew Richards, Inc. Orthopaedics Catalog Information, Sep. 1996, pp. 1-16.

Lowery, Gary L., M.D., Ph.D., Sofamor Danek Group, Inc. Publication entitled, "Orion Anterior Cervical Plate System: Surgical Technique," 1994, pp. 1-24.

Apfelbaum, R., M.D., Aesculap Scientific Information publication entitled, "Posterior Transarticular C1-2 Screw Fixation for Atlantoaxial Instability," 1993, pp. 1-15.

Danek Titanium Cable System publication by Danek Group, Inc., 1994, 6.pp.

Sofamor Danek publication entitled, "Atlas Cable System: Evolution of the Cable System for Spinal Applications," 1995, 2 pp.

AcroMed Publication entitled, "AcroMed Songer Cable System: Ordering information for Implants and Instruments," Apr. 1996, 4 pp.

Songer, Matthew N., M.D., "ACROMED Cable System by Songer: Technique Manual," 1993, pp. 1-20.

SpineTech, Inc. publication entitled, "BAK/Cervical Interbody Fusion System," 1994, 2 pp.

SpineTech, Inc. publications entitled, "Instrumentation BAK Interbody Fusion System," "Biomechanics BAK Interbody Fusion System," and "Porosity BAK Interbody Fusion System," 1996, 12 pp.

SpineTech, Inc. publication entitled, "The BAK Interbody Fusion System," 1996, 4 pp.

Depuy Motech, Inc. publication entitled, "Moss Miami 3-Dimensional Spinal Instrumentation: Taking Spinal Instrumentation to a New Dimension," 1995, 8 pp.

Shufflebarger, Harry L., M.D., "Moss Miami Spinal Instrumentation System: Methods of Fixation of the Spondylopelvic Junction," Lumbosacral and Spinopelvic Fixation, 1996 by Raven Publishers, Philadelphia, pp. 381-393.

SpineTech, Inc. publication entitled, "The Bone Harvester," 1996, 2 pp.

Wright Medical Technology Publication entitled, "Versalok Low Back Fixation System," 1996, pp. 1-4.

Danek Medical, Inc. Publication entitled, "TSRH Lumbar System," 1991, pp. 1-4.

Spinal Concepts Inc. Publication entitled, "The BacFix ss—Posterior Lower Back Fixation System—Written Surgical Technique," 1997, pp. 1-11.

Dialog Web results for search for English language abstract for SU1424826 published Sep. 23, 1988, downloaded and printed from www.dialogweb.com on Jan. 22, 1999 (2 pages).

Dialog Web results for search for English language abstract for DE 4323956 published Jul. 19, 1993, downloaded and printed from www.dialogweb.com on Jan. 22, 1999 (2 pages).

Dialog Web results for search for English language abstract for FR 2717068 published Sep. 15, 1995, downloaded and printed from www.dialogweb.com on Jan. 22, 1999 (1 page).

International Search Report dated Oct. 23, 2003, in PCT/US03/08230, 9 pages.

Communication Pursuant to Article 96(2) EPC issued in European Patent Application No. 03 716 666.7 dated Dec. 12, 2004, Spinal Concepts, 4 pages.

Communication Pursuant to Article 96(2) EPC issued in European Patent Application No. 03 716 666.7 dated Jan. 30, 2006, Spinal Concepts, 3 pages.

Official Action in Japanese Patent Application No. 2003-575864 dated Sep. 11, 2008 and English translation (5 pages), 10 total pages.

Danek Medical, Inc., TSRH Spinal Implant System Surgical Technique Manual 1990, 15 pages., Memphis, TN.

Danek Medical, Inc., "TRSH Crosslink Surgical Technique Manuall 990", 10 ppages, Memphis, TN.

Acromed Corp., "The ISOLA Transverse Rod Connectors: Principles and Techniques," date unknown, 10 pages, Raynham, MA.

Beadling, Lee, "FDA Clears Spinal Cages for Interbody Lumbar Fusion," Orthopedics Today Publication, date unknown, 2 pages, Thorofare, NJ.

Medpro Month, "Trends in Spine & Disk Surgery," Dec. 1996, vol. VI, No. 11-12, pp. 280-284.

Surgical Dynamics, "Ray Threaded Fusion Cage Surgical Technique Manual," 1996, 12 pages, Norwalk, CT.

Surgical Dynamics, "Ray Threaded Fusion Cage," 1996, 6 pages, Norwalk, CT.

Codman & Shurleff, Inc., "Sof'wire Cable System," Jun. 1992, 6 pages, Randolph, MA.

"Spinal Disorders" publication, 4 pages, date unknown.

O'Brien, John P., Ph.D., "Interbody Fusion of the Lumbar Spine," Orthopaedic Product News, 3 pages, at www.opnews.com, North Yorkshire, UK.

Roy, Marcel, Abstract of "Variation of Young's Modulus and Hardness in Human Lumbar Vertebrae . . . Nanoindentation," American Society of Mechanical Engineers, 1996, 4 pages.

Oxland, Thomas R., Ph.D. et al., "Biomechanical Rationale — the BAK Interbody Fusion System: . . . Solutions," SpineTech Inc., 1994, 17 pages, Minneapolis, MN.

Shufflebarger, Harry L. M.D, Clinical Issue: Rod Rotation in Scoliosis Surgery, 1995, Oakland, CA, 5 pages.

Acromed, "Instruments", Redmond Surgical Instruments, dated unknown, 3 pages, Lake Zurich, IL.

Songer, Acromed Cable System by Songer Cervical Technique Manual, Acromed, Cleveland, OH, 17 pages.

Spine Tech, Inc., Patient Information on Spinal Fusion Surgery and the BAK Interbody Fusion System, 1993, Spine Tech, Inc., Minneapolis, MN, 5 pages.

U.S. Patent and Trademark Office, Office Action issued in U.S. Appl. No. 10/387,361, mailed Sep. 4, 2004, Landry, 5 pages.

U.S. Patent and Trademark Office, Office Action issued in U.S. Appl. No. 10/387,363, mailed May 13, 2005, Landry, 4 pages.

U.S. Patent and Trademark Office, Office Action issued in U.S. Appl. No. 10/387,361, mailed Nov. 1, 2006, Landry, 5 pages.

U.S. Patent and Trademark Office, Office Action issued in U.S. Appl. No. 10/387,363, mailed Jan. 22, 2007, Landry, 6 pages.

U.S. Patent and Trademark Office, Office Action issued in U.S. Appl. No. 10/387,361, mailed Jun. 12, 2007, Landry, 6 pages.

U.S. Patent and Trademark Office, Office Action issued in U.S. Appl. No. 10/387,363, mailed Jun. 29, 2007, Landry, 6 pages.

U.S. Patent and Trademark Office, Office Action issued in U.S. Appl. No. 10/387,361, mailed Nov. 28, 2007, Landry, 6 pages.

IP Australia, Examination Report in Application No. 2003220366 mailed Feb. 05, 2008, Spinal Concepts, Inc., 2 pages.

Canadian Intellectual Property Office, Requisition by Examiner in Application No. 2,478,311 mailed Mar. 30, 2009, 2 pages, Spinal Concepts, Inc.

* cited by examiner

INSTRUMENTATION AND PROCEDURE FOR IMPLANTING SPINAL IMPLANT DEVICES

PRIORITY CLAIM

This application claims priority to U.S. Provisional Application No. 60/363,219 entitled "Instrumentation And Procedure For Implanting Fusion Devices," filed Mar. 11, 2002. The above-referenced provisional application is incorporated by reference as if fully set forth herein.

BACKGROUND

1. Field of the Invention

The present invention generally relates to the field of medical implants and more particularly to instruments used to insert spinal implants. An embodiment of the invention relates to instruments that may be used to form a spinal implant in a disc space between adjacent vertebrae during a spinal fixation procedure.

2. Description of Related Art

An intervertebral disc may be subject to degeneration. Degeneration may be caused by trauma, disease, and/or aging. An intervertebral disc that becomes degenerated may have to be partially or fully removed from a spinal column. Partial or full removal of an intervertebral disc may destabilize the spinal column resulting in subsidence or deformation of vertebrae. Destabilization of a spinal column may result in alteration of a natural separation distance between adjacent vertebrae. Maintaining the natural separation between vertebrae helps to prevent pressure from being applied to nerves that pass between vertebral bodies. Excessive pressure applied to the nerves may cause pain and/or nerve damage. During a spinal fixation procedure, a spinal implant may be inserted within a space created by the removal or partial removal of an intervertebral disc between adjacent vertebrae. The spinal implant may maintain the height of the spine and restore stability to the spine. The spinal implant may be a fusion device. Intervertebral bone growth may fuse the implant to adjacent vertebrae. The spinal implant may be an artificial disc.

A spinal implant may be inserted during a spinal fixation procedure using an anterior, lateral, or posterior spinal approach. An anterior spinal approach may be a preferred method for some spinal implant procedures. An anterior spinal approach may require less bone removal and muscle distraction than a posterior spinal approach. In addition, an anterior spinal approach may involve less risk of nerve damage than a posterior spinal approach.

During an anterior spinal approach, a surgical opening may be made in the abdomen of a patient. This opening may extend from the abdomen to an anterior surface of the spine. For some patients, the opening may be ten or more inches in depth. The opening needs to be large enough to accommodate instrumentation for insertion of a spinal implant within a disc space. A discectomy may be performed to remove or partially remove a defective or damaged intervertebral disc. The discectomy creates a disc space for a spinal implant. The amount of removed disc material may correspond to the size and type of a spinal implant to be inserted.

A type of spinal implant used to promote fusion of adjacent vertebrae may include a pair of engaging plates and struts. Struts may be positioned between the engaging plates to establish a separation distance between the engaging plates. Spinal implants having engaging plates and struts are described in U.S. Pat. No. 6,045,579 issued to Hochschuler et al., which is incorporated by reference as if fully set forth herein. Struts may separate and join engaging plates of an assembled spinal implant. The engaging plates may provide a large contact area between the spinal implant and vertebrae that are to be fused together. The large contact area may minimize subsidence and deformation of the vertebrae during use. The engaging plates may include protrusions that inhibit migration of the inserted implant. Each engaging plate may also include several openings to promote bone growth through the spinal implant to fuse the adjacent vertebrae together. The spinal implant may be formed in the disc space so that no over-distraction of the adjacent vertebrae is needed.

The engaging plates and struts may allow an anterior height of a spinal implant to differ from a posterior height of the implant. The availability of spinal implants that have different anterior and posterior heights may allow a surgeon to choose a spinal implant that will provide proper lordotic alignment and vertebral separation for a particular patient.

The struts of a spinal implant establish a separation distance between the engaging plates of the implant. The separation distance between the engaging plates may in turn establish a desired separation distance between adjacent vertebrae when the implant is formed between the vertebrae. Establishing a desired separation distance between engaging plates and adjacent vertebrae may establish a proper distance between vertebral bodies.

The struts of a spinal implant may include load-sharing members. The load-sharing members may allow a portion of a load placed on the implant to be transmitted to bone growth material placed within the implant. The transmittal of a portion of a load to bone growth material may promote bone growth in accordance with Wolff's law. Bone growth through and around a spinal implant may fuse the adjacent vertebrae together. Bone growth material inserted into the implant may be, but is not limited to, autograft bone harvested from a secondary location, such as the iliac crest; allograft material; or artificial bone growth material.

Another type of spinal implant may include a cage into which bone growth material is placed. A method of inserting the spinal implant may include forming a disc space that is slightly smaller than a height of the spinal implant and impacting the implant into the opening. Impacting an implant may be dangerous and may not inhibit an inserted implant from backing out of a disc space after insertion. An alternate method of inserting a spinal implant may involve forming a disc space that is slightly larger than a height of the implant to be inserted into the disc space by distracting the vertebrae with a distraction device. After a spinal implant is inserted, the distraction device may be removed. Distracting the adjacent vertebrae a distance that allows a spinal implant to be inserted into a disc space, however, may not be desirable. Imperfect elastic characteristics of connective tissue may not allow connective tissue to return to a pre-distracted state after the distraction device is removed.

Another type of spinal implant includes threading along a substantial portion of a length of the implant. The implant may be screwed into a prepared opening between adjacent vertebrae. The threaded implant may include self-tapping threads, or the spinal implant may be threaded into a tapped opening.

SUMMARY

An instrumentation set may be used to form a bone implant within a space between two bones of a patient. The instrumentation set may allow a significant portion of positioning and manipulation to be affected from above an incision in a patient. The instrumentation set may allow for insertion of a bone implant in a simple, efficient, and safe manner. In an embodiment, the bone implant is a spinal implant formed in a disc space between adjacent vertebrae. In other embodiments, the bone implant may be an implant placed in a space formed between two portions of a bone. The bone may be shorter than a desired length. The bone implant may be used to establish a desired length of bone. The instrumentation may require a small opening in the patient while still allowing ample visibility of a surgical site, an implant, and instrumentation during the insertion procedure.

Bone implants may be made from a wide variety of materials. Bone implants may be formed from, but are not limited to being formed from, metal, ceramics, bone, polymers, or combinations thereof. In an embodiment, a bone implant is made of a titanium alloy (such as Ti6AL4V). Portions of a bone implant that contact bone may be coated with a material, such as, but not limited to, titanium plasma spray, bone morphogenic proteins, and/or hydroxyapatite to promote osseointegration. In addition to, or instead of, coating portions of the bone implant that contact bone, portions of the bone implant that contact bone may be roughened to promote osseointegration. The portions may be roughened by any of several processing techniques, including, but not limited to, chemical etching, surface abrading, shot peening, an electric discharge process, and/or embedding particles in the surface.

A bone implant, or a portion of a bone implant, may be made of a biodegradable and/or bioabsorbable material. For example, a polymer used to form a bone implant, or a portion of a bone implant, may be, but is not limited to, a polyanhydride, an alpha polyester, and/or a polylactic acid-polyglycolic acid copolymer.

An instrumentation set for a spinal implant insertion procedure may include various insertion instruments. The insertion instruments may include, but are not limited to, a spreader, a separator, and a strut seater. The instrumentation set may also include spinal implant components. The implant components may include, but are not limited to, implant members of various sizes and lordotic alignment and connectors of various sizes. A spreader may allow implant members that form a spinal implant to be positioned between two adjacent vertebrae. A separator may be positioned between the implant members to establish a desired separation distance between the implant members. In an embodiment, a connector or connectors may be inserted through the separator and into the implant members. The connectors may join the implant members together.

A spreader may allow implant members to be positioned within a prepared disc space between vertebrae. The spreader may be sufficiently long to allow easy placement of a distal end of the spreader in the disc space from above an incision in a patient. The spreader may include holders that secure implant members of a spinal implant to the spreader. The holders and attached implant members may be positioned in a disc space during an anterior spinal implant insertion procedure. A distance between the holders may be adjusted by inserting a separator into the spreader. The separator may establish a desired separation distance between outer surfaces of the implant members without excess distraction of the vertebrae.

In addition to establishing a desired separation distance between a pair of implant members, a separator may include passages that conduct connectors to the implant members. The connectors may fix the separation distance between the implant members. In an embodiment of a spinal implant, implant members may include slots. Portions of connectors may be positioned in the slots to join the implant members together.

An embodiment of a spreader may have implant holders. An opening or openings in the implant members may press-fit onto the implant holders. Locking pins may be inserted into slots of the spreader and into implant member slots to secure the spreader to the implant members and to maintain proper alignment of the spreader slots with respect to the implant member slots. In an alternate embodiment, a spreader may have implant holders that are inserted into dovetail channels of the implant members. When the spreader is fully inserted into the dovetail channels, implant member slots will align with slots in the spreader. Gaps in the implant holders may be compressed when the spreader is inserted into the dovetailed channels. A force exerted by arms to counter the compression of the gaps may hold the implant members on the spreader. Alternatively, the implant holders may have spring members that fit into an opening in the implant members and apply a force to the dovetailed channels to hold the implant members on the spreader.

During some implant insertion procedures, a disc space may be too small to allow for insertion of implant members coupled to a spreader without protrusions of the implant members scarring surfaces of adjacent vertebrae during insertion. In some embodiments, distractors may be used to separate vertebrae to a distance that is less than the desired separation distance to be established by the spinal implant. The spinal implant may then be formed in the disc space.

In other embodiments, insertion guides may be positioned in a disc space that is too small to allow for insertion of implant members. The insertion guides may include stops that limit an insertion depth into the disc space. After placing insertion guides in the disc space, a spreader with attached implant members may be inserted into the disc space between the insertion guides. The insertion guides may be removed after insertion of the implant members and spreader.

Insertion of a separator in a spreader may force outer surfaces of implant members against vertebrae. Continued insertion of the separator into the spreader may drive protrusions of the implant members into vertebral bone. The separator may be impacted into the spreader using a mallet or a slap hammer. The separator may establish a desired separation distance between vertebrae.

After establishing a separation distance between vertebrae by inserting a separator into a spreader, connectors may be positioned in implant member slots to join implant members together. After insertion of the connectors into the implant members, the spreader and the separator may be removed from between the vertebrae.

A connector seater may be coupled to the implant members and to a connector or connectors. The connector seater may apply force to the implant members and the connector or connectors to affix the connector or connectors to the implant members. The force applied by the connector seater to the implant members and the connectors may be sufficient to deform implant member slots and/or portions of the connectors to affix the connectors to the implant members. The connector seater may include an indicator to indicate when a sufficient amount of force has been applied to the connectors and the implant members. After connectors are affixed to implant members, the connector seater may be removed from an opening in a patient. Bone growth material may be placed in a space between the implant members before the opening is closed.

The connectors may allow for minor adjustment of a distance separating the implant members so that the implant members apply a compressive load to bone growth material positioned between the implant members. If a large compressive force is applied to the implant members, the connectors and implant members may act as a single unit that dissipates the force over the large surface area of the implant members.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
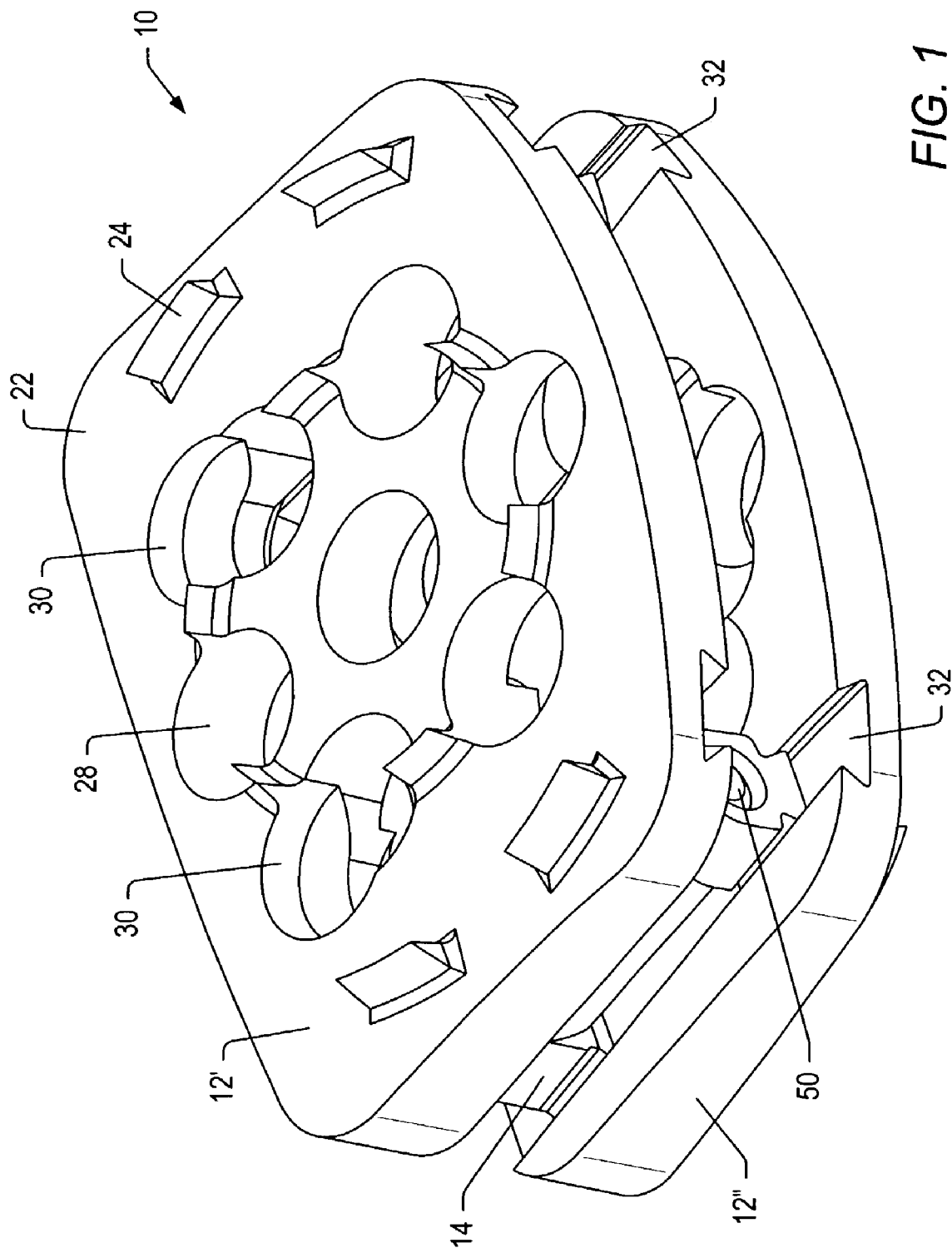
FIG. 1 shows a perspective view of an embodiment of a spinal implant.

While the invention is susceptible to various modifications and alternative forms, specific embodiments thereof are shown by way of example in the drawings and will herein be described in detail. The drawings may not be to scale. It should be understood, however, that the drawings and detailed description are not intended to limit the invention to the particular form disclosed, but to the contrary, the intention is to cover all modifications, equivalents, and alternatives falling within the spirit and scope of the present invention as defined by the appended claims.

DESCRIPTION OF PREFERRED EMBODIMENTS

Figure 2:
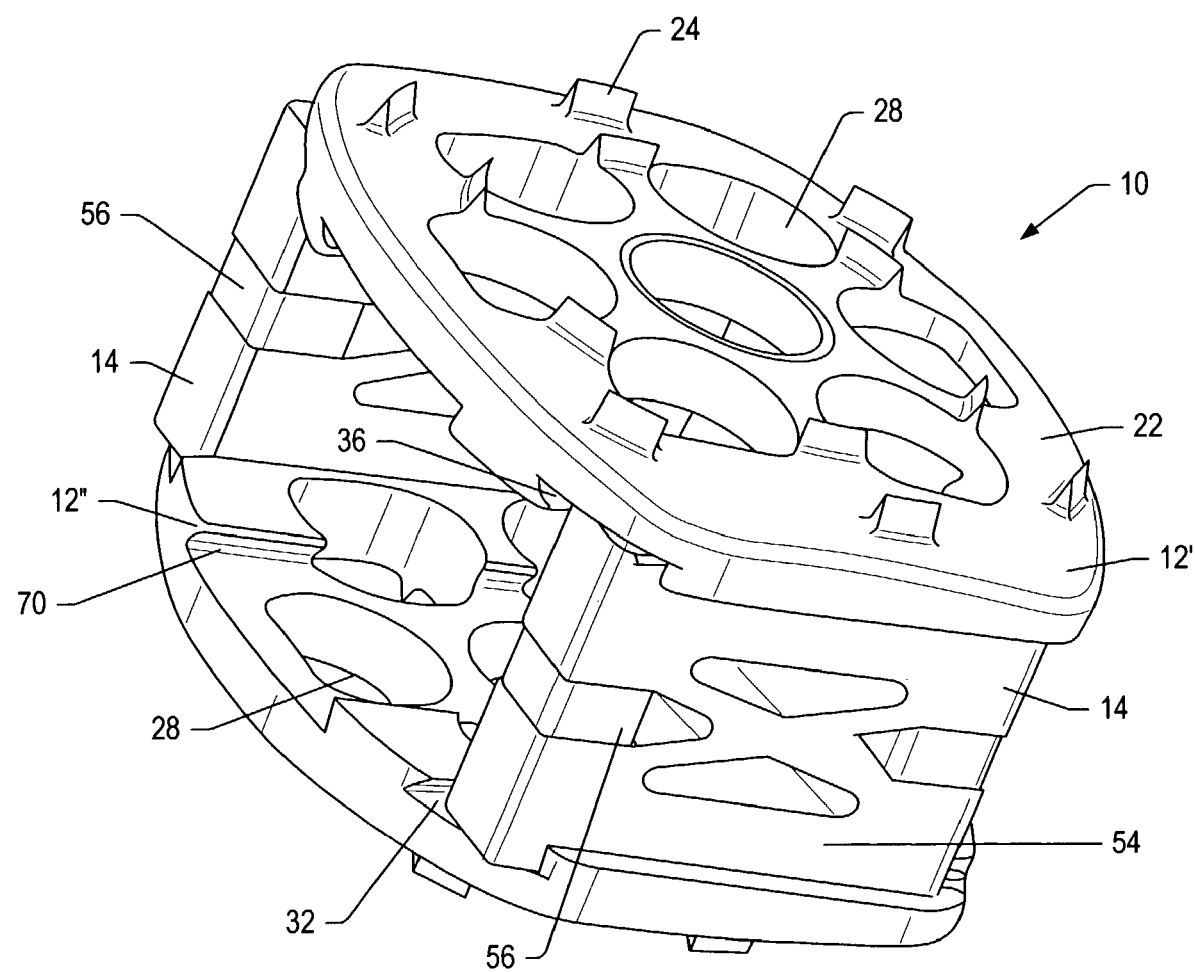
FIG. 2 shows a perspective view of an embodiment of a spinal implant.

Referring to the drawings, FIG. 1 and FIG. 2 show perspective views of embodiments of implants 10. An implant may include members and a spacer between the members. The members may be implant members that contact surfaces of bone that are to be joined together by the implant. The spacer may establish a desired distance between the members. The spacer may be a formed of one or more components. In some embodiments, implant 10 may be a spinal implant. In some embodiments, the spinal implant may be a fusion device that promotes bone growth between vertebrae to fuse the vertebrae together. In some embodiments, the spinal implant may be an artificial disc that joins two vertebrae together while still allowing for at least some motion of the vertebrae relative to each other. In some embodiments, the implant may be an implant that joins and promotes fusion of two portions of a bone (e.g., a femur).

Implant 10 may include a pair of implant members 12 and connector or connectors 14 that couple the implant members together. In an embodiment of implant 10, implant members 12 may be a pair of engaging plates and connectors 14 may be struts.

Figure 3:
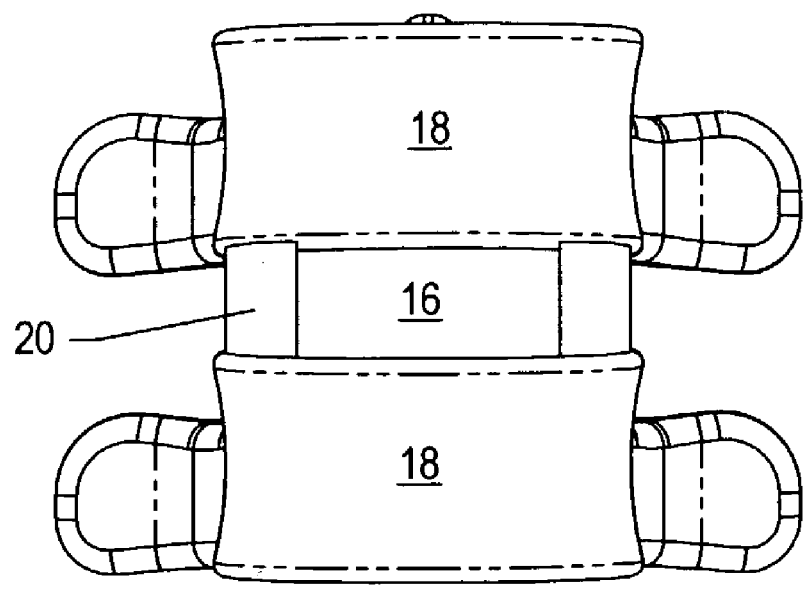
FIG. 3 shows a plan view of an intervertebral disc space between adjacent vertebrae.

FIG. 3 depicts disc space 16 between adjacent vertebrae 18. A portion or all of intervertebral disc 20 may be removed between adjacent vertebrae 18 during a discectomy that forms disc space 16.

Figure 4:
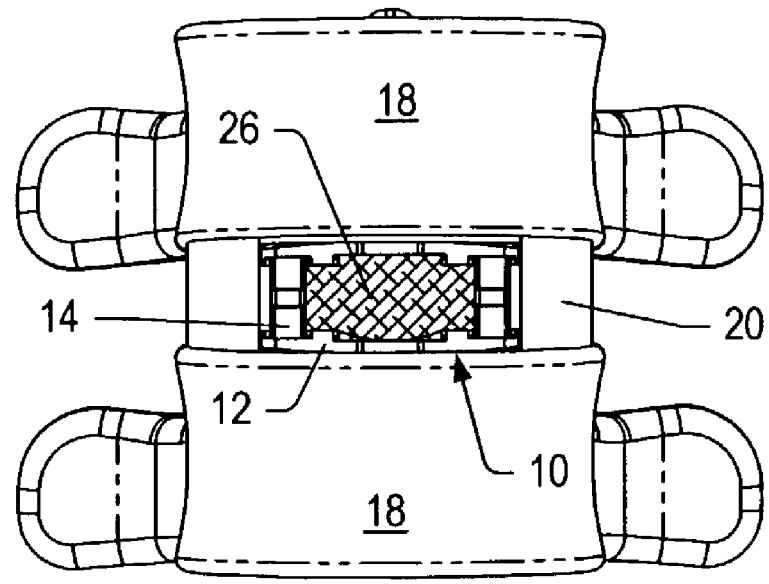
FIG. 4 shows a top view of a spinal implant positioned between adjacent vertebrae.

FIG. 4 depicts an embodiment of implant 10 inserted in disc space 16 formed in intervertebral disc 20. Implant 10 may provide spinal column stability and promote bone growth that fuses adjacent vertebrae 18 together.

Figure 5:
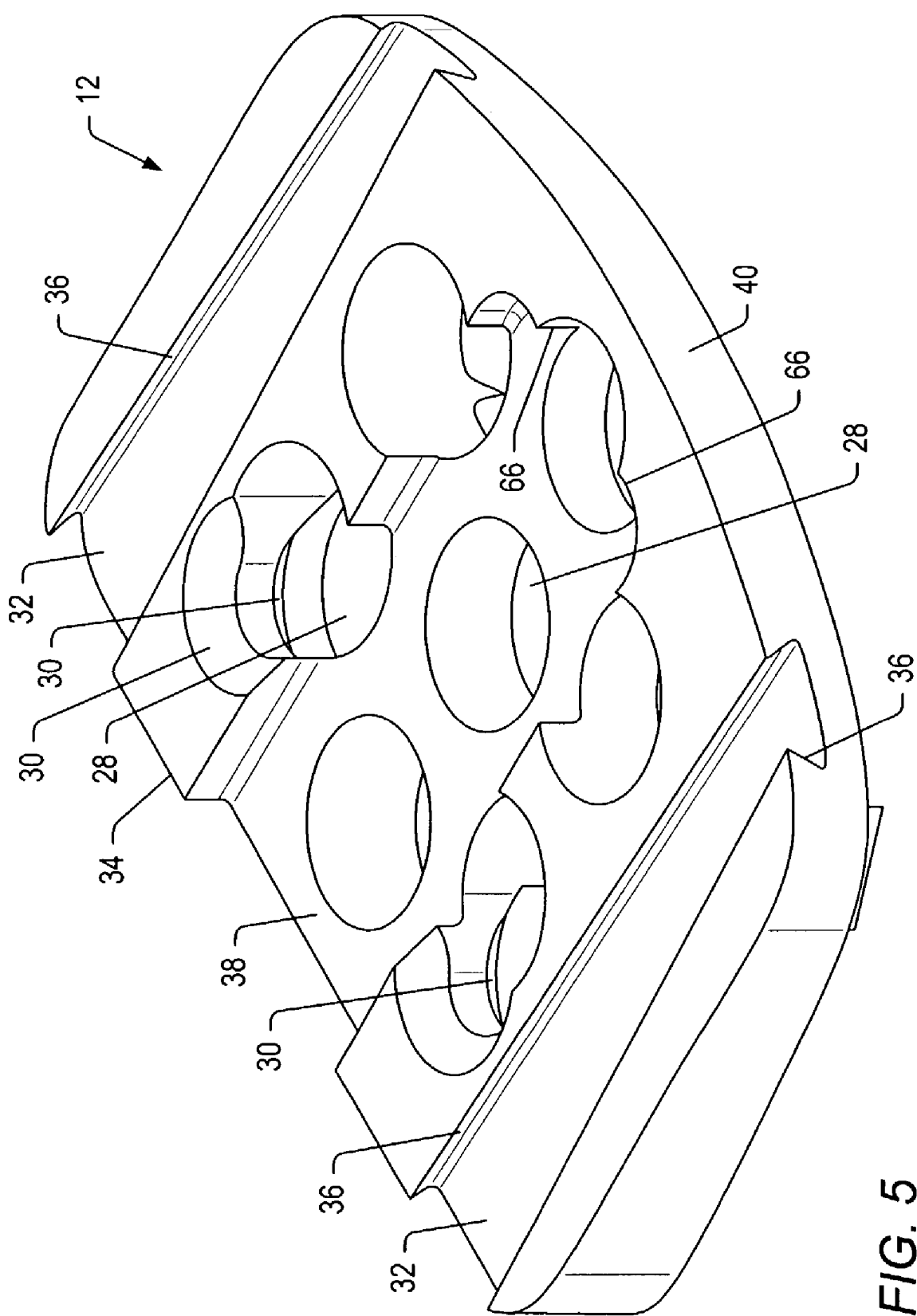
FIG. 5 shows a perspective view of an embodiment of an engaging plate that emphasizes an inner surface the engaging plate.
Figure 6:
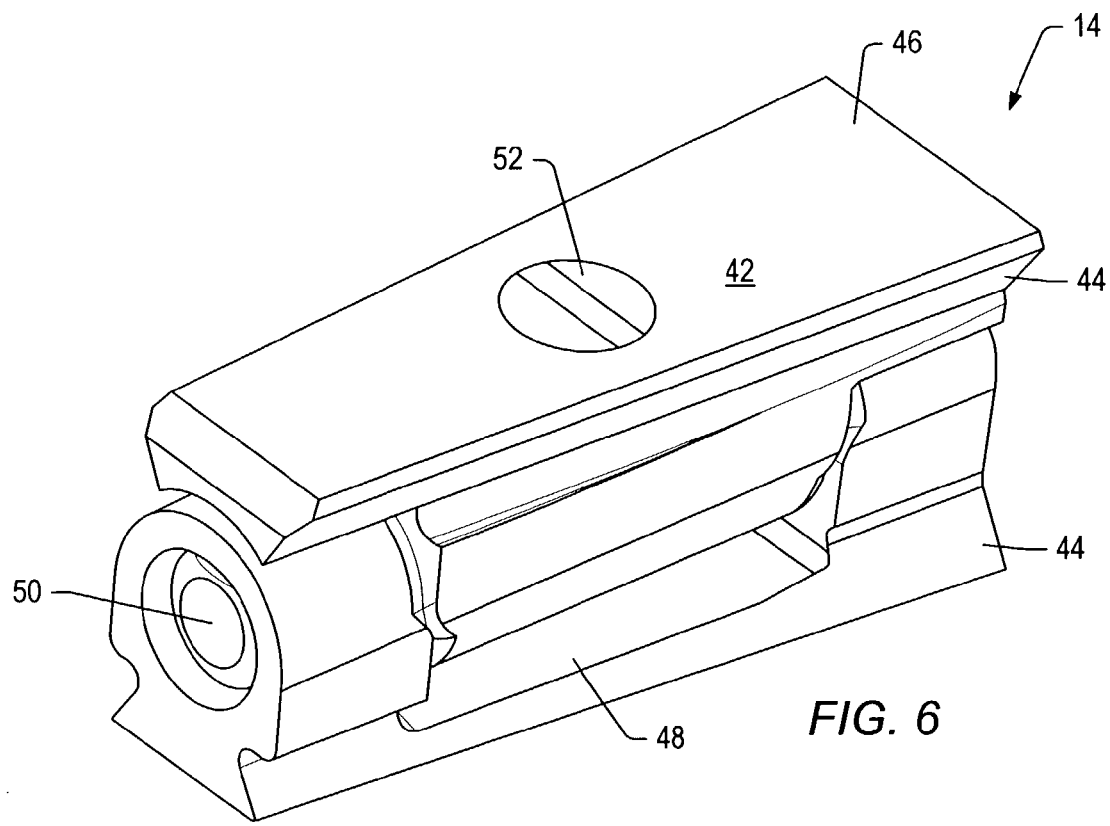
FIG. 6 shows a perspective view of an embodiment of a connector.
Figure 7:
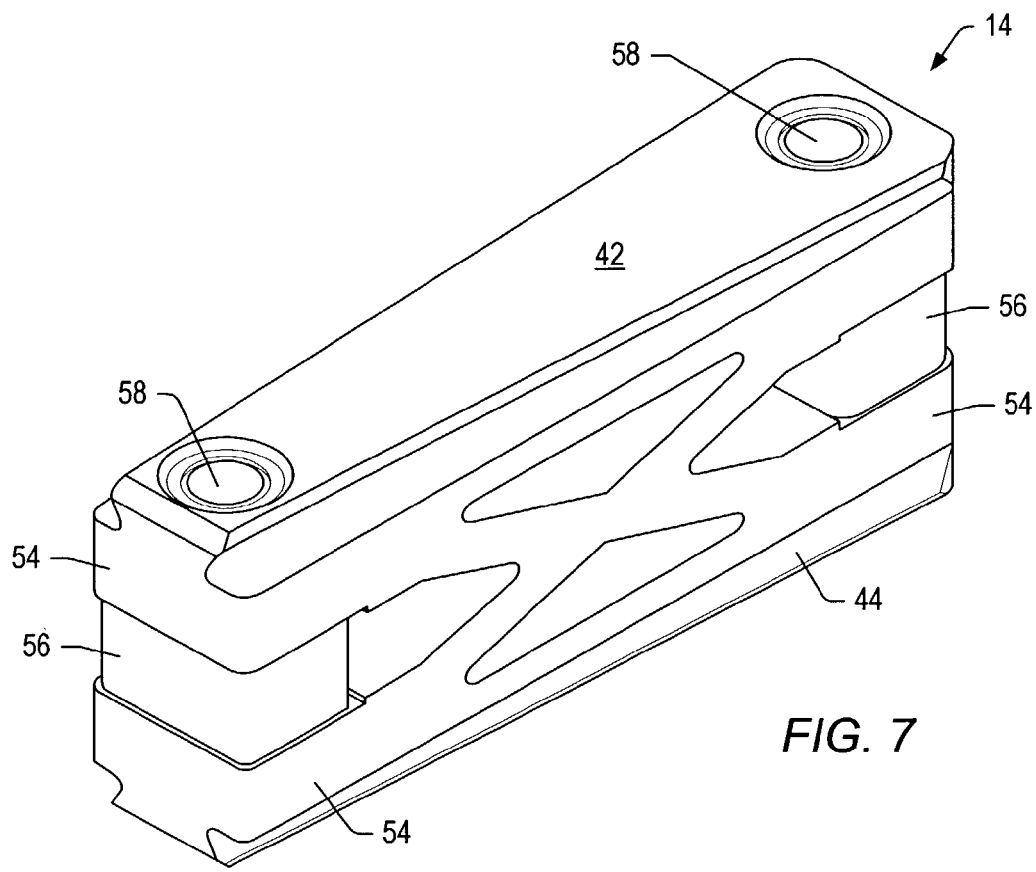
FIG. 7 shows a perspective view of an embodiment of a connector.

FIG. 5 shows an embodiment of implant member 12 emphasizing inner surfaces of the implant member. FIG. 6 and FIG. 7 show embodiments of connectors 14. Implant members and connectors may be made of any biocompatible material, including, but not limited to, titanium, titanium alloy, stainless steel, ceramic material, bone, polymers, or combinations thereof. In an embodiment, implant members are formed of a titanium and aluminum alloy, such as Ti6Al4V-Eli. An instrumentation set for a spinal insertion procedure may include a number of different sizes of implant members. Pairs of implant members included in an instrumentation set may have.

An instrumentation set may include implant members. Implant members having different surface areas that will contact or be adjacent to bone when inserted into a patient may be provided in the instrumentation set. For example, an instrumentation set may include large, medium, and/or small size implant members. Surface areas of large implant members that will contact or be adjacent to bone when inserted into the patient are larger than similar surface areas of medium implant members, which are larger than similar surface areas of small implant members. A surgeon may determine which size of implant members to use prior to or during the implant insertion procedure. A pair of implant members of the same size may form a part of an implant that is formed in a patient.

Outer surface 22 of implant member 12 (shown in FIG. 1 and FIG. 2) may include a coating or outer layer, such as, but not limited to, a titanium plasma spray, bone morphogenic proteins, and/or hydroxyapatite. The coating may promote osseointegration. Osseointegration refers to a healing process that results in the formation of connecting bone that attaches an object to the bone. The object may be an implant or a portion of an implant.

In addition to, or instead of, coating outer surfaces 22, the outer surfaces may be roughened to promote osseointegration of the implant members to adjacent vertebrae. Outer surfaces 22 of implant member 12 may be roughened by any of several processing techniques, including, but not limited to, chemical etching, surface abrading, shot peening, using an electric discharge process, or embedding particles in the surface.

Outer surface 22 of implant member 12 may have a large surface area so that there is a large contact area between implant member 12 and an adjacent vertebra. The large contact area may minimize subsidence and/or deformation of the vertebrae that implant 10 contacts.

As shown in FIG. 1 and FIG. 2, implant member 12 may include a plurality of protrusions 24 on outer surface 22. Protrusions 24 of formed implant 10 may extend into adjacent vertebrae to securely fasten the implant to the adjacent vertebrae. In an embodiment, protrusions 24 are arranged in two radial rows each containing 6 protrusions. Other arrangements with fewer or more protrusions may also be used. Protrusions 24 may extend about 0.2 mm or more from outer surface 22 of implant member 12. In an embodiment, protrusions 24 extend approximately 1 mm from outer surface 22. Protrusions 24 may anchor the implant member to surfaces of vertebrae. Outer surface 22 of implant member 12 may include curvature. The curvature may allow outer surfaces 22 of implant members 12 to substantially conform to shapes of vertebral surfaces. For example, outer surface 22 of an implant member may conform to an anatomical dome of a vertebra.

Embodiments of implant members 12 may include sloped outer surfaces 22. The sloped outer surfaces may allow an anterior height of assembled implant 10 to differ from a posterior height of the implant. Several different pairs of implant members 12 having different sloped outer surfaces 22 may be included in an instrumentation set provided to a surgical team that will perform an implant insertion procedure on a patient. The availability of implant members 12 of differing slopes may allow a surgeon to form implant 10 that will provide proper lordotic alignment for the patient. In an embodiment of an instrumentation set, implant members 12 provided in the instrumentation set have slopes that range from about 0° to about 9° in approximately 3° increments. This allows a surgeon to form implant 10 with lordotic adjustment from about 0° (wherein each implant members has 0° of lordotic angle) to about 18° of lordotic adjustment (wherein each implant member has 9° of lordotic angle). In some embodiments, implant members with differing amounts of lordotic angle may be used to provide a desired amount of lordotic adjustment. For example, a lordotic adjustment of about 9° may be obtained by forming an implant using an implant member with 9° of lordotic angle and a second implant member having 0° of lordotic angle. Lordotic adjustment of 9° may also be obtained by forming an implant using an implant member with 6° of lordotic angle and an implant member having 3° of lordotic angle. In an alternate embodiment of implant 10, connector or connectors 14 may include a sloped surface to provide lordotic adjustment. In other embodiments, other ranges and increments of slopes of implant members and/or connectors may be provided.

Implant members may be color-coded and/or include indicia. The color-coding and/or indicia may indicate a size of a particular implant member. For example, an implant member may be stamped with the letter "M" to indicate that the implant member is a medium sized implant member. Similarly, an implant member may be color-coded and/or include indicia to indicate an amount of lordotic angle that the implant member has.

When implant 10 is positioned between adjacent vertebrae 18, as represented in FIG. 4, bone growth material 26 may be packed between two implant members 12 coupled by connector or connectors 14. Bone growth material 26 may be, but is not limited to, autograft bone (such as bone from the patient's iliac crest), allograft bone, synthetic bone growth material, or combinations thereof.

As depicted in FIG. 1, FIG. 2, and FIG. 5, implant member 12 may include a plurality of openings 28. Openings 28 in upper implant member 12' may vertically align with openings in lower implant member 12" of implant 10 when the implant is formed in a disc space. Bone may develop through openings 28 to fuse the vertebrae together. Bone graft may promote fusion of adjacent vertebrae. Some openings 28 may have recessed surfaces 30, as shown in FIG. 1.

FIG. 5 shows a perspective view of implant member 12 that emphasizes inner surfaces of the member. Each implant member 12 may include tapered slots 32. Slots 32 may be widest proximate anterior side 34 of implant member 12. Sidewalls 36 of slots 32 may be angled, or dovetailed, so that the slots are wider at their bases than at inside surfaces of implant members 12.

As depicted in FIG. 5, implant member 12 may also include recessed surface 38. Recessed surface 38 may begin at anterior side 34 of implant member 12 and stop before reaching posterior side 40 of the implant member. In an embodiment, the sidewalls of recessed surface 38 are substantially straight. In other embodiments, the sidewalls of recessed surface 38 may be dovetailed, or of any other appropriate shape for coupling implant member 12 to an insertion tool.

FIG. 6 and FIG. 7 show embodiments of connector 14. Connector 14 may be a strut. Connector 14 may have tapered end surfaces 42 and angled side portions 44. Tapered end surfaces 42 of connector 14 may be positioned in tapered slots of implant members. The taper of tapered end surface 42 may substantially correspond to the taper of implant member slots 32 (shown in FIG. 5), so that there is a large contact area between an implant member and a connector inserted into the implant member. The angle of sides 44 may correspond to the angle of tapered slot sides in an implant member. The tapered shape of the slots of the implant members and tapered end surfaces 42 of connectors 14 may only allow removal of the connectors from the implant member in a reverse manner to the insertion of the connectors into the slots. When it is desired to affix connectors to implant members, large forces may be applied to the connectors and the implant members to deform the tapered slots and/or connectors so that removal of the connectors is prevented.

A frictional connection may be formed between connector 14 and implant members across a large contact area when the connector is fully inserted into slots of the implant members. In another embodiment, connectors 14 may be attached to implant members by means other than frictional engagement. For example, an interference fit may be formed between a connector and implant members. Channels that hold the connectors within the implant members may include projections that fit within indentions in the connector to form an interference fit when the connector is fully inserted into the channel of the implant member. Alternately, the channels that hold connectors 14 within the implant members may include indentions that form an interference fit with projections extending from the connector when the connector is fully inserted into the channel of the implant members. An amount of force needed to insert connector 14 fully within the channel of the implant members may inhibit unintentional full insertion of the connector into the implant members. The interference fit may inhibit removal of connector 14 from the implant members when the connector is fully inserted into the implant members.

An embodiment of connector 14, such as the connector embodiment depicted in FIG. 6, may include first member 46, second member 48, and pin 50. Assembled connector 14 may be held together by setscrew 52. Assembled connector 14 may be positioned between implant members. Connectors 14 may be provided in an instrumentation set for a spinal insertion procedure in various sizes. For example, an instrumentation set may be provided with connectors for medium and large implant members. An instrumentation set may include connectors that form implants with separation distances between implant members ranging from about 8 mm to about 16 mm in approximately 2 mm increments. Other size ranges and/or size increments of connectors 14 may be provided.

Pin 50 may hold first member 46 to second member 48. Setscrew 52 may contact and apply force against pin 50. The force may inhibit removal of pin 50 from first member 46 and second member 48. First member 46 may be able to rotate relative to second member 48. The pin-type of connection in connectors 14 may allow connectors of different sizes to be inserted into implant members. The resulting implant may have different heights at medial and lateral ends of the formed implant. In other embodiments, implant members may be formed with different medial and lateral heights so that a resulting implant will have different heights at medial and lateral ends of the implant, while each connector used to form the implant has substantially the same height.

After formation of an implant in a patient, compressive forces may be applied to implant members of the implant. Compressive forces applied to the implant members may deflect pin 50 of connector 14 and allow the first implant member of the implant to move a small distance towards the second implant member of the implant. As such, some of the compressive force applied to the implant members may be transferred to bone growth material positioned between the implant members. Application of stress to the bone growth material may promote formation of bone that fuses together the vertebrae joined by the implant. Bone needs to undergo stress to maintain normal density. A bone's strength and health is directly related to its density. When bone is not stressed, or is shielded from stress, it may lose density and resorb into the body.

Application of compressive forces to an implant that exceed a force to which a spinal column is normally exposed may cause connector members 46, 48 and pin 50, shown in FIG. 6, to act as a single, solid member. The single, solid member may not allow the implant members to be compressed towards each other closer than a predetermined spacing. Excessive force applied to the vertebrae may cause bone fractures adjacent to the implant. A large contact surface between the implant and the vertebrae may promote dissipation of large forces over large vertebral areas so that bone fracturing is inhibited. Repetitive application of large forces to bone growth material may inhibit formation of connecting bone and promote formation of a fibrous mass. Limiting movement of implant members towards each other may inhibit application of excessive forces to bone growth material placed between the implant members.

FIG. 7 depicts an alternate connector embodiment. Connector 14 may include flexible member 54, limiters 56, and pins 58. Pins 58 may couple limiters 56 to flexible member 54. Pins 58 may be press-fit, threaded, welded, glued, or otherwise attached to flexible member 54. Compressive forces applied to implant members of a formed implant may compress flexible member 54, allowing some of the force to be shared by bone growth material located between the implant members. Limiters 56 are sized so as not to allow flexible member 54 of connector 14 to be compressed towards each other closer than a predetermined spacing.

Connectors 14 and limiters 56 of an implant may selectively control the amount of strain applied to bone growth material placed within the implant. For example, connectors 14 may limit the total strain on the bone growth material within the implant to less than about 0.5% of the strain applied to the implant members. Excessive strain on the bone growth material, for example, greater than about 1% of the strain applied to the implant members, may cause the bone growth material to form a fibrous mass instead of bone. Connectors 14 may be made of a relatively rigid material, such as medical grade titanium. Connectors 14 may shield the bone growth material and support a large portion (over 99%) of the strain applied to the implant members, while still allowing some strain to be applied to the bone growth material to promote formation of bone.

Portions of material may be removed in a desired pattern from a connector blank so that the connector formed from the blank will have desired flexibility characteristics. Ends of the blank may be formed so that the ends couple to implant members. FIG. 7 depicts an embodiment of connector 14 having an "X" style of pattern that allows for compression of flexible member 54. Other patterns may also be used. Openings in the pattern of the connectors may be sufficiently small to inhibit bone graft from passing through the openings when the connectors form part of an assembled implant. Flexible members 54 may be formed using a variety of methods including, but not limited to, milling, drilling, laser cutting, electron discharge machining, and/or masking and etching.

Connectors 14 and implant members may function together to inhibit fracture of adjacent vertebrae by distributing large forces applied to the vertebrae throughout a large contact area between the implant members and the vertebrae.

As depicted in FIG. 1 and FIG. 2, connectors 14 may establish a separation distance between outer surfaces 22 of implant members 12 when the connectors are inserted into the tapered slots 32 of the implant members. A plurality of connectors 14 that establish various separation distances between implant members 12 may be included in an instrumentation set provided to a surgical team that will perform an implant insertion procedure. The availability of several different connector sizes may allow formation of implant 10 in a patient that will establish a desired separation distance between adjacent vertebrae.

In an embodiment of an instrumentation set, connectors 14 may be provided that are capable of forming implants 10 having maximum separation distances between outer surfaces 22 ranging from about 8 mm to about 26 mm in approximately 2 mm increments. Inserting connectors 14 of proper size between implant members 12 may form appropriately sized implant 10. Connectors 14 may be color-coded and/or include numerical indicia that inform a user of the size of implant 10 that will be formed by the connectors. For example, connector 14 that forms implant 10 having a maximum separation of about 12 mm between outer surfaces 22 of implant members 12 may be blue and/or include an etched, printed, or stamped "12" on a portion of the connector. Similarly, connector 14 that forms implant 10 having a maximum separation of about 14 mm between outer surfaces 22 of implant members 12 may be green and/or include an etched, printed, or stamped "14" on a portion of the connector. Connector 14 may also include indicia that indicate the size of implant member 12 that the connector is to be used with. For example, connector 14 may include an etched, stamped, or printed "S", "M", or "L" on a portion of the connector to indicate a connector that is to be used with small, medium, or large implant members 12.

Figure 8:
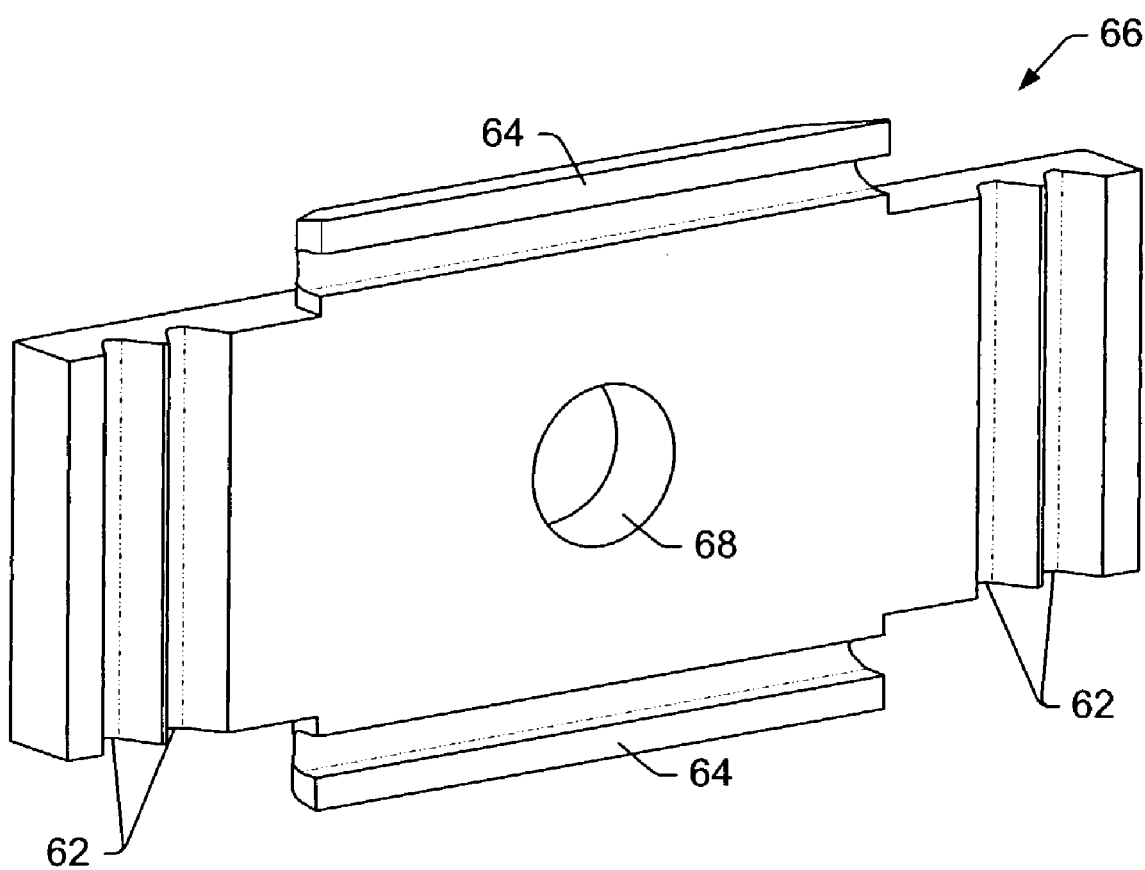
FIG. 8 shows a perspective view of an embodiment of a backing plate.

An optional backing plate may be positioned proximate the posterior side of an assembled implant. FIG. 8 depicts an embodiment of optional backing plate 60. Backing plate 60 may be made of a biocompatible polymer, such as, but not limited to, polyethylene, polypropylene, or polyvinyl chloride. Alternatively, backing plate 60 may be made of a bioabsorbable and/or biodegradable polymer, such as, but not limited to, a polyanhydride, an alpha polyester, and/or a polylactic acid-polyglycolic acid copolymer. Backing plate 60 may include indentions 62. Indentions 62 may allow a single size backing plate to be adapted to fit within implants of different sizes. A complete backing plate may fit within a large implant. The ends of backing plate 60 may be cut or otherwise separated at indentions 62 so that the backing plate fits within a smaller implant. An insertion depth of backing plate 60 in an assembled implant may be limited when tabs 64 contact end walls 66 of implant members 12 which define a posterior end of recessed surfaces 38. End walls 66 of implant member 12 are depicted in FIG. 5.

During an implant insertion procedure, a discectomy may be performed to remove a portion of intervertebral disc 20 to form disc space 16 between vertebrae 18, as shown in FIG. 3. An implant may be formed within disc space 16. A backing plate may be used when a remaining portion of disc 20 is herniated. Opening 68 in backing plate 60 (shown in FIG. 8) may be threaded or otherwise releasably affixed to an insertion rod. The insertion rod may allow insertion and positioning of backing plate 60 between the implant members of the implant from a position above an opening in a patient. The ability to insert and position backing plate 60 from above the opening in the patient may promote visibility and ease of insertion of the backing plate into an assembled implant. After insertion, the rod may be unthreaded or otherwise removed from backing plate 60. Backing plate 60 may inhibit migration of bone growth material from the implant. Backing plate 60 may not be necessary if the remaining portion of the disc after the discectomy is not herniated or otherwise breached.

FIGS. 9-55 show embodiments of instruments that may be used to form an implant in a patient during a fusion procedure. The instruments used during formation of the implant may include, but are not limited to, width and depth spacers 100, height spacers 200, separators 300, spreaders 400, locking pins 500, extender 600, mallet 650, forceps 700, depth gauges 800, slap hammer 900, and insertion guides 1000. Additionally, seater 1100 and retainer 1300 may be used to securely fasten connectors to implant members. Various parts of the instruments may be formed of metal, ceramics, polymers, or combinations thereof. The materials used to form the parts of the various instruments may have high heat resistance and chemical resistance to withstand sterilization procedures.

Instruments used during a fusion procedure may be provided in an instrumentation set. The instrumentation set may include components of an implant to be formed. The instrumentation set may also include other instruments such as, but not limited to, various types of rongeurs, various types of curettes, bone awls, and tamps.

Figure 9:
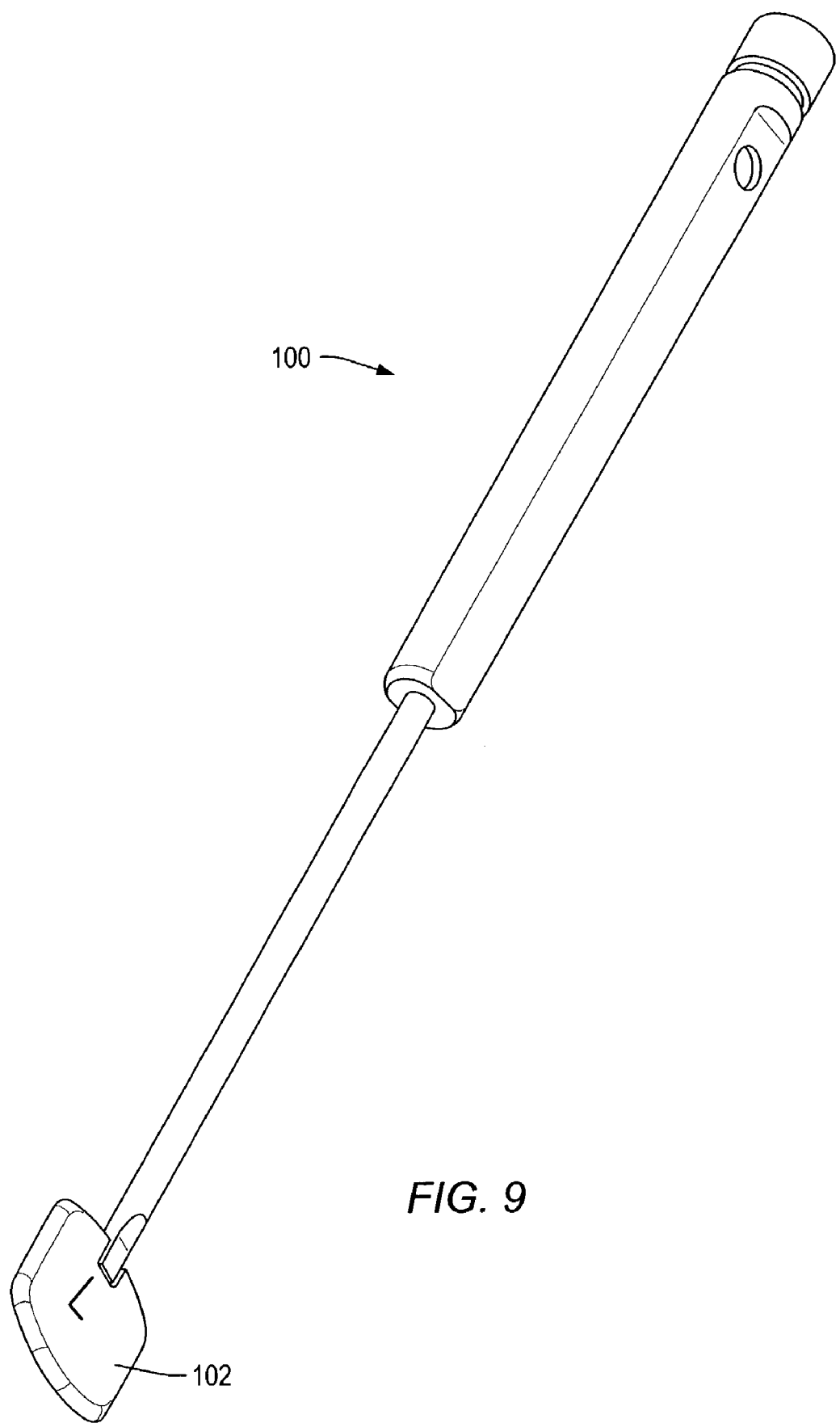
FIG. 9 shows a perspective view of an embodiment of a width and depth spacer.

FIG. 9 shows an embodiment of width and depth spacer 100. End 102 of width and depth spacer 100 may have a shape that substantially corresponds to a size of a front surface of an implant member. Sizes of width and depth spacers corresponding to sizes of implant members included in an instrumentation set may be provided in the instrumentation set. For example, if the instrumentation set includes medium and large implant members, the instrumentation set may include a first width and depth spacer with an end that corresponds to large implant members and a second width and depth spacer with an end that corresponds to medium implant members. An alternate embodiment of a width and depth spacer may have a first end that substantially corresponds to a first size of implant members and a second end that substantially corresponds to a second size of implant members. Outer surfaces of ends 102 may include indicia to indicate the relative size of the ends. The indicia may be printed, etched, or otherwise placed on the ends.

During formation of a disc space between adjacent vertebrae, portions of an intervertebral disc may be removed. Width and depth spacer 100, together with radiological images, may be used to determine the proper width and depth of an opening for a particular size of implant member. Similarly, width and depth spacers may be used during formation of an opening between bone segments that are to be fused together by an implant.

Figure 10:
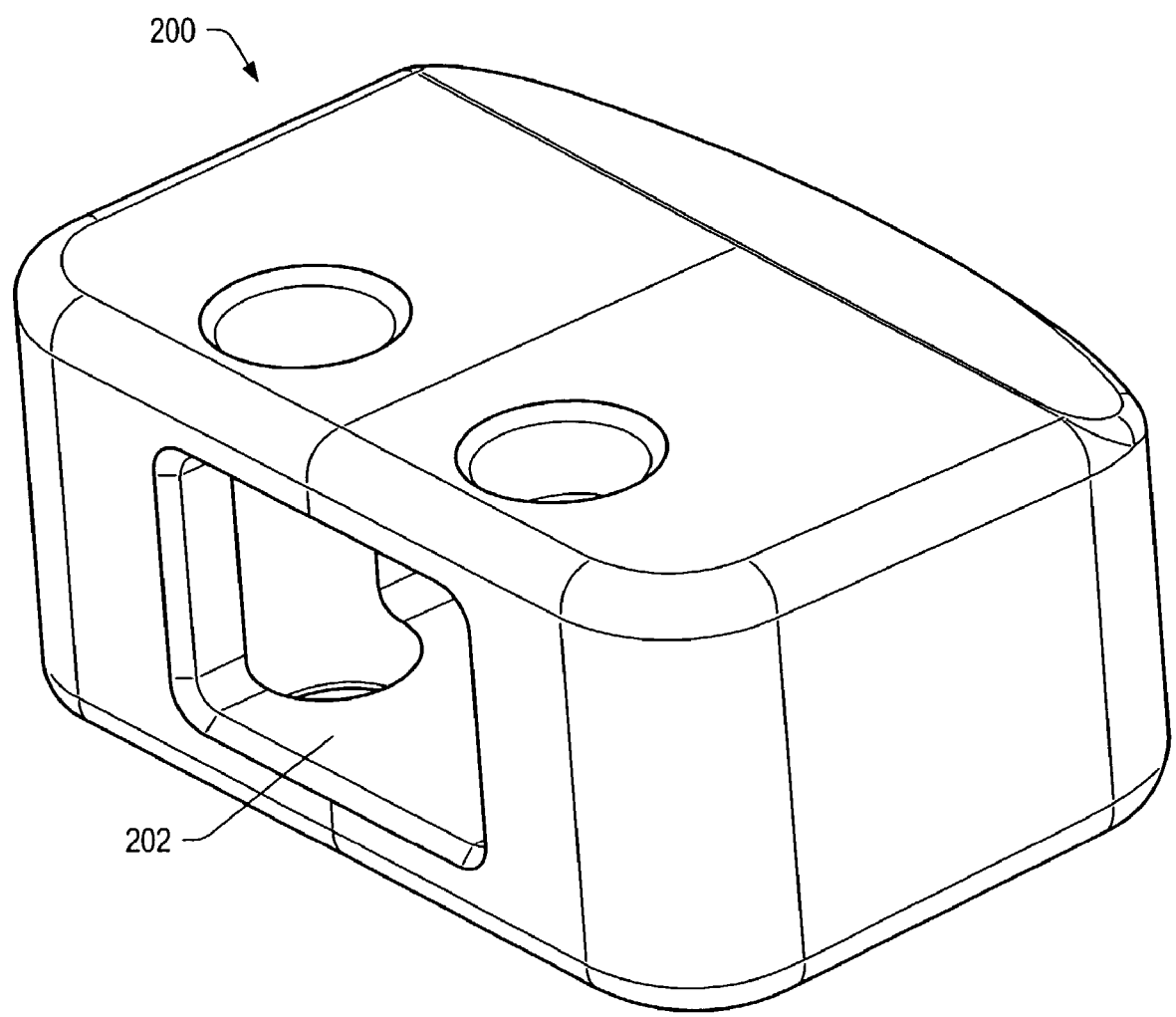
FIG. 10 shows a perspective view of an embodiment of a height spacer.

After formation of a disc space or an opening between bone segments, a height spacer may be used to determine the size of an implant to be formed. FIG. 10 depicts an embodiment of height spacer 200. A surgeon may attach height spacer 200 to a slap hammer. The surgeon may place an end of the slap hammer in attachment mount 202 and place the height spacer at a top of a prepared space formed by a discectomy. The surgeon may insert height spacer 200 with a force applied by impacting a slide of the slap hammer against a lower stop. If height spacer 200 fits easily within the disc space with one or two impacts from the slap hammer, or without any impacts from the slap hammer, the height spacer may be too small. A larger height spacer may be attached to the slap hammer and inserted into the prepared disc space. If height spacer 200 will not fit within the disc space with force applied from the slap hammer, the height spacer may be too large. A smaller height spacer may be attached to the slap hammer and inserted into the prepared disc space. If height spacer 200 fits within the disc space after three or four impacts from the slap hammer, the height spacer may correspond to a properly sized implant. After insertion of height spacer 200 within the disc space, the spacer may be removed from the disc space by impacting the slap hammer slide against an upper stop. During some insertion procedures, an extender (such as extender 600 depicted in FIG. 21) and a mallet may be used to insert height spacers into a disc space.

Figure 11:
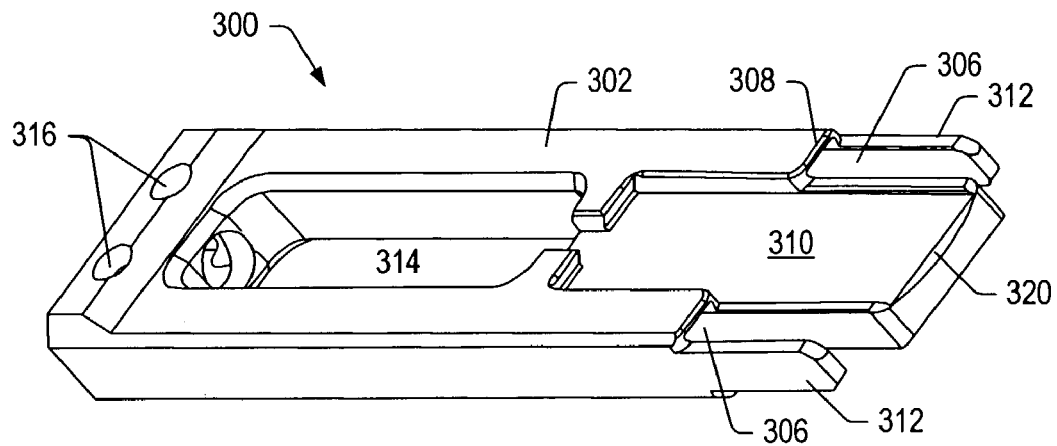
FIG. 11 shows a perspective view of an embodiment of a separator.
Figure 12:
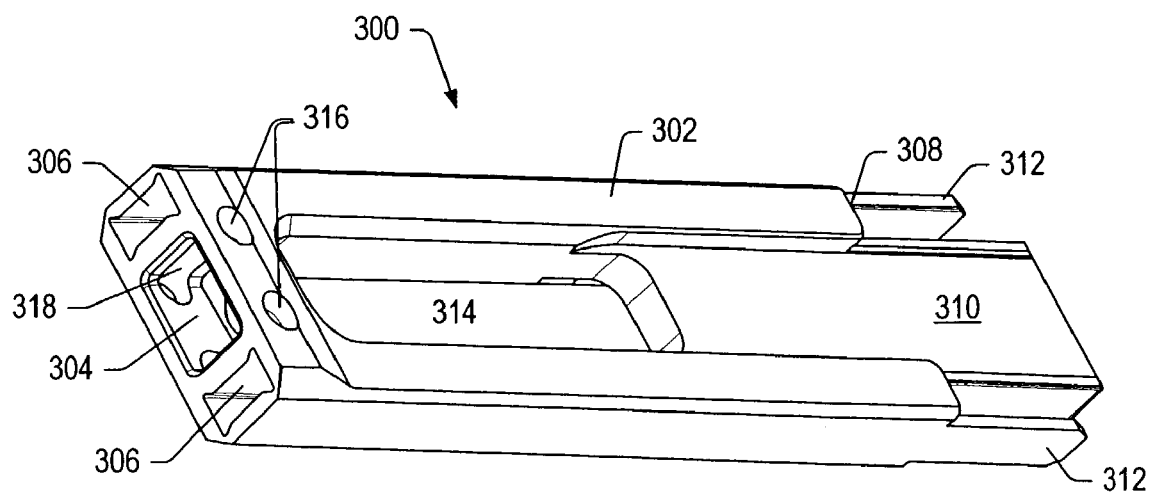
FIG. 12 shows a perspective view of an embodiment of a separator.

FIGS. 11 and 12 show perspective views of separator embodiments. Separator 300 may include body 302, attachment mount 304, passages 306, stop surfaces 308, tongue 310, and arms 312. Body 302 may include central opening 314 that reduces the weight of separator 300. Attachment mount 304 may allow separator 300 to be coupled to a drive device, such as a slap hammer. Holes 316 through an upper portion of separator 300 may define contact surfaces 318 that engage detents of an insertion/removal instrument, such as detents 902 of slap hammer 900 shown in FIG. 27. Passages 306 through body 302 may be sized to allow connectors and locking pins 500 (shown in FIG. 20) to pass through separator 300. Stop surfaces 308 may limit an insertion depth of separator 300 into a spreader. Tongue 310 and arms 312 of separator 300 may establish a separation distance between implant members that are coupled to a spreader, such as the embodiment of spreader 400 depicted in FIG. 14. Separation provided by separator 300 may allow the formation of an implant in a disc space without excess distraction of adjacent vertebrae. Tongue 310 may include spreader contact surfaces 320 that facilitate insertion of separator 300 into the spreader. Surfaces 320 may be chamfered, rounded, or otherwise machined to facilitate insertion of separator 300 into the spreader. Arms 312 may inhibit rotational motion of separator 300 with respect to the spreader during an implant insertion procedure.

The separator may establish a separation distance between a pair of implant members coupled to a spreader. A connector or connectors may couple the implant members together after the separator establishes a proper separation distance. The separator may include grooves or other types of guides that direct the connector or connectors to proper positions between the implant members. Some separator embodiments may not include connector passages through the separator to guide the connectors to proper positions between the implant members. In some embodiments, the connector or connectors may be inserted between the implant members without interaction with the separator. For example, a connector may be attached to forceps. A connector may be properly positioned between the implant members before being released from the forceps.

A spreader may be used to position implant members between adjacent bone structure, such as vertebrae, and aid in establishing proper distraction. A separator may be inserted into a spreader to establish a desired separation distance between vertebrae or bone segments.

Figure 13:
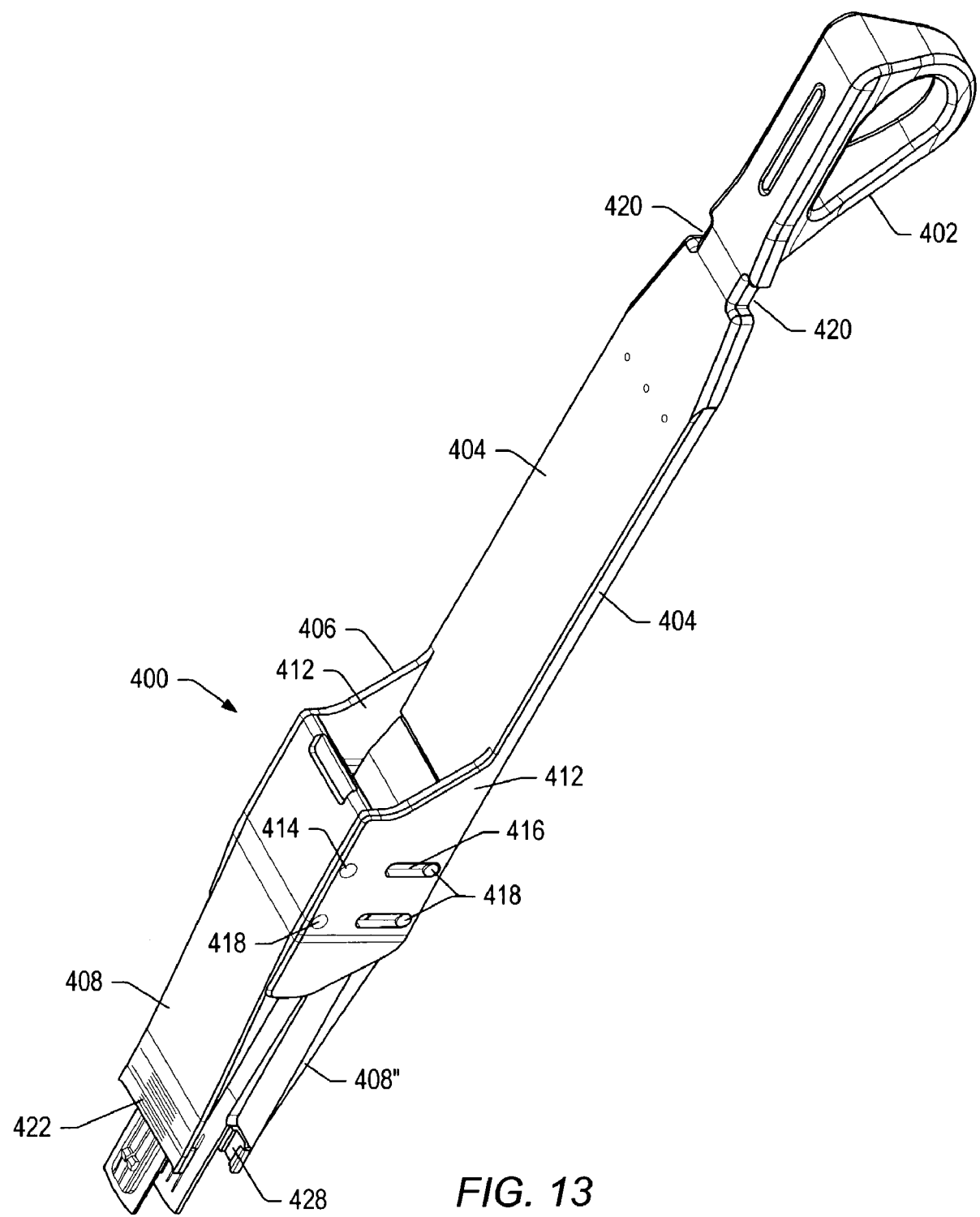
FIG. 13 shows a perspective view of an embodiment of a spreader with plate holders in a spread apart position.
Figure 14:
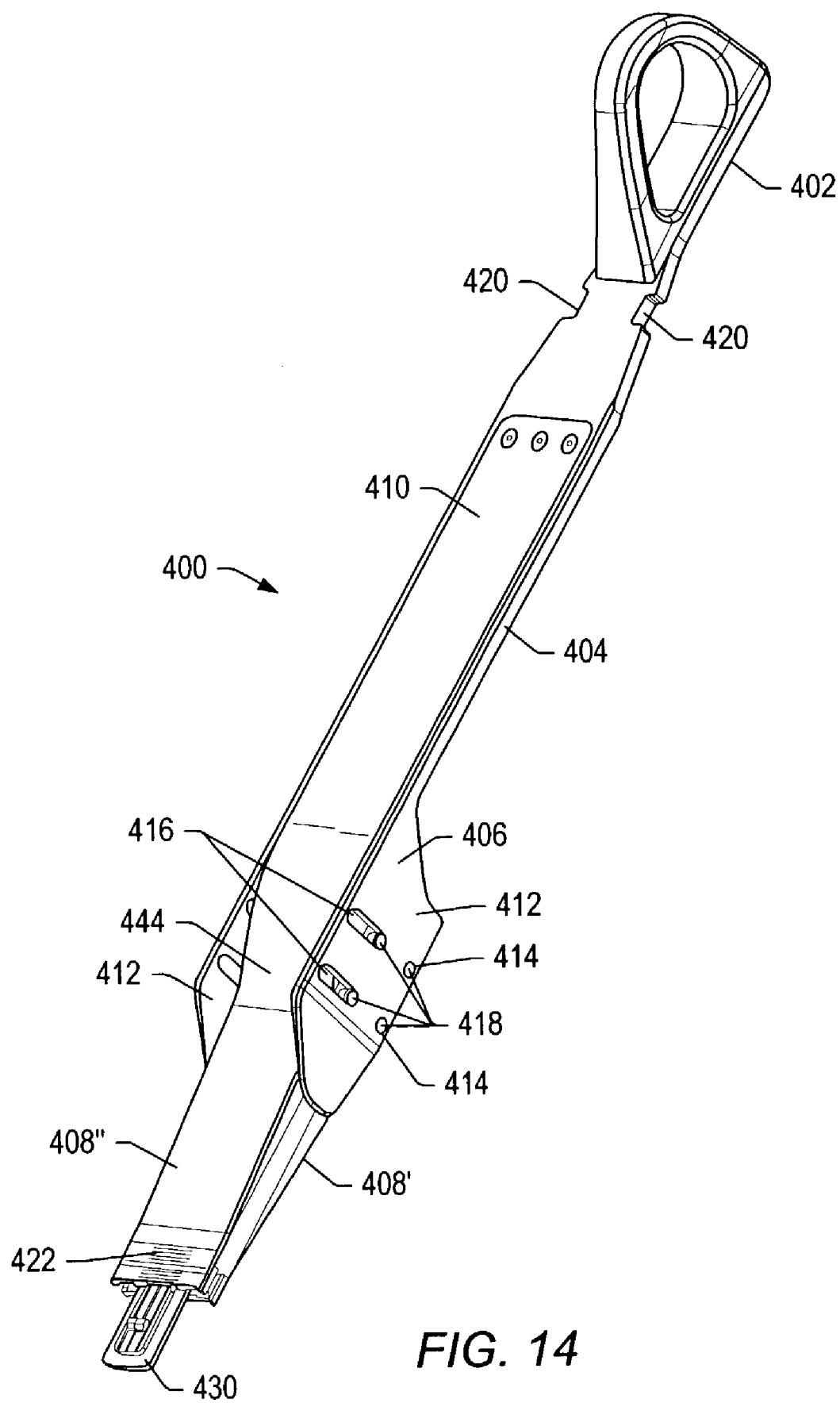
FIG. 14 shows a perspective view of an embodiment of a spreader with plate holders in an initial position.

FIG. 13 shows a perspective view of an embodiment of spreader 400. Spreader 400 may include may include handle 402, extension portion 404, body 406, and member holders 408. As shown in FIG. 14, spreader 400 may also include spring member 410. FIG. 13 shows a spreader embodiment with member holders 408 in a spread apart position, as if a separator was positioned between the member holders. FIG. 14 shows a spreader embodiment with member holders 408 in an initial position prior to insertion of a separator between the member holders.

Handle 402 may be an easily graspable member that allows member holders 408 to be positioned at desired locations within a disc space. Extension portion 404 may provide a spreader with sufficient length so that handle 402 extends out of a patient when member holders are positioned between vertebrae or bone segments during a fusion procedure. Body 406 allows member holders to move laterally relative to each other.

In some embodiments, such as the embodiments depicted in FIG. 13 and FIG. 14, handle 402 may be an integral part of body 406 of spreader 400, and member holders 408 may be attached to the body. "Integral part" refers to parts that are formed from one piece of material, or from separate pieces that are attached together to inhibit axial and rotational movement of the separate pieces relative to each other.

Figure 15:
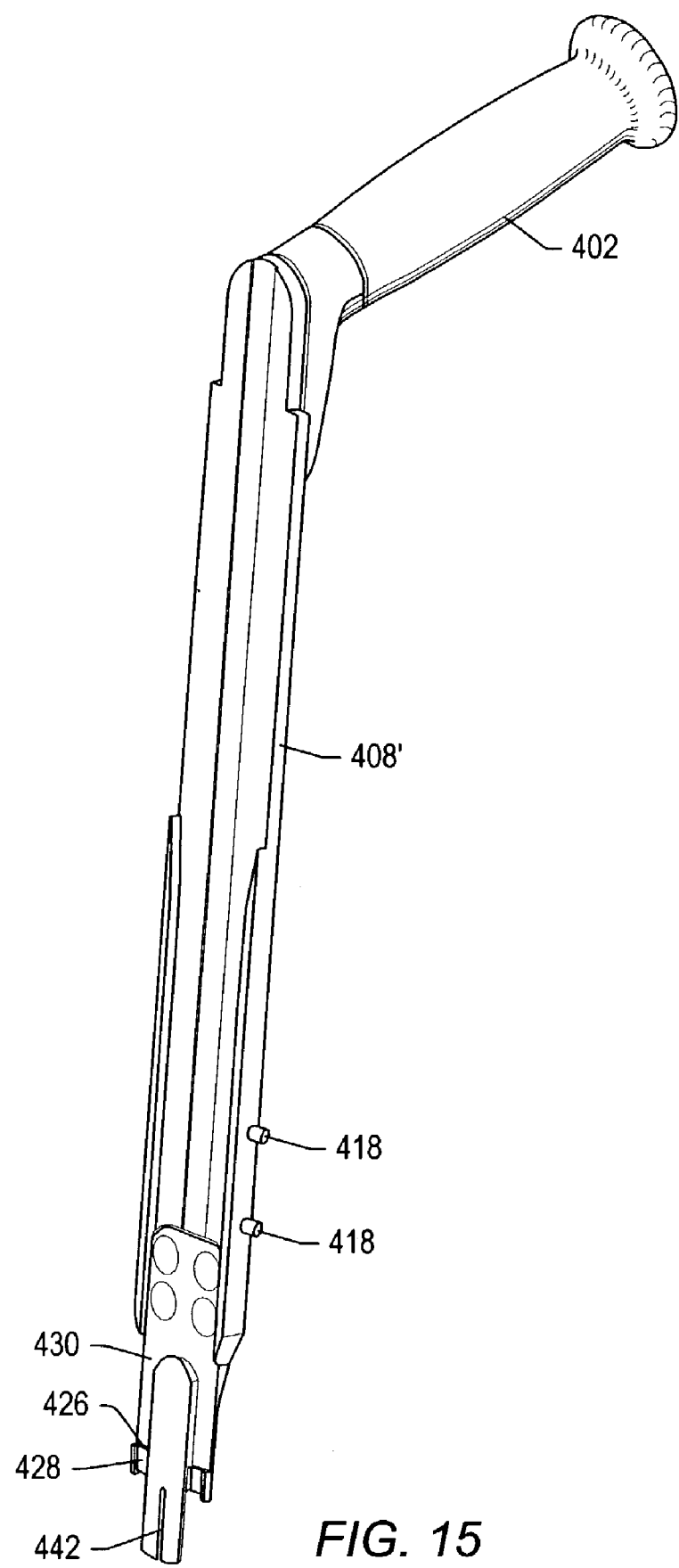
FIG. 15 shows a perspective view of an embodiment of an integral handle and plate holder combination.
Figure 16:
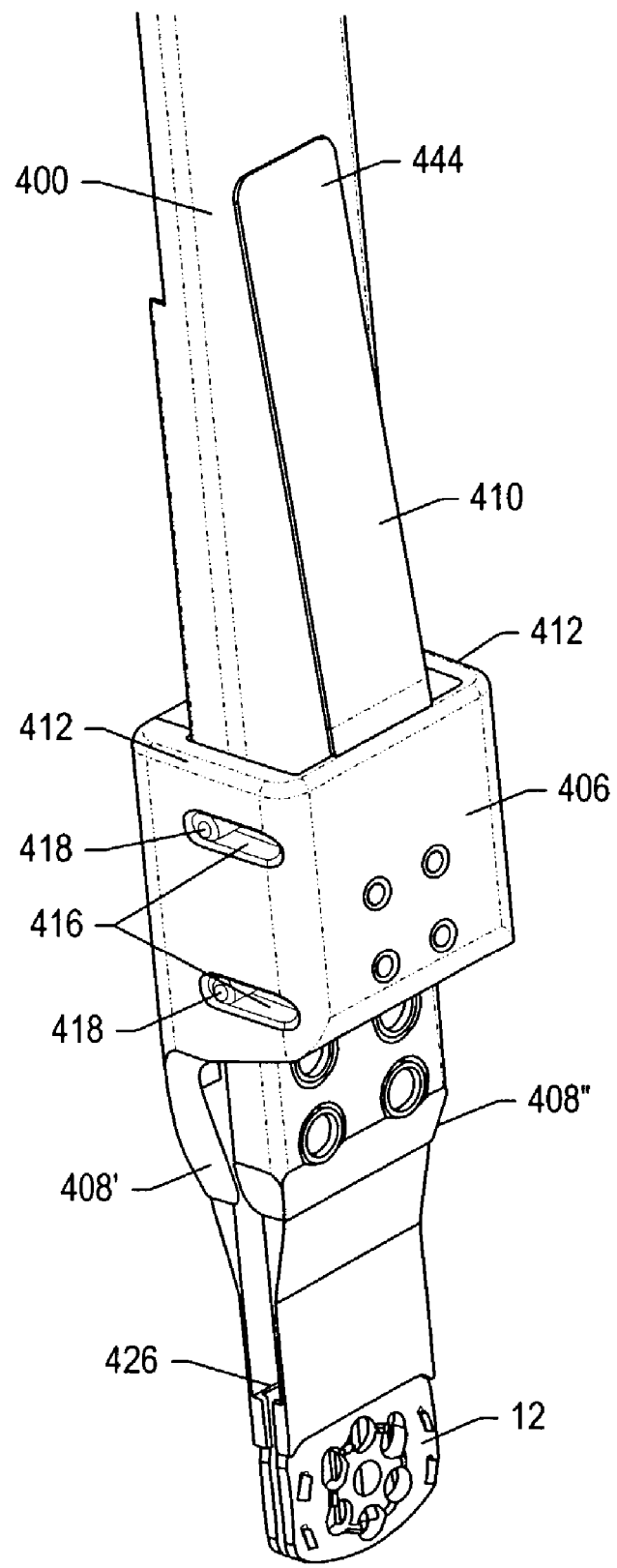
FIG. 16 shows a perspective view of a portion of an embodiment of a spreader with engaging plates coupled to the spreader.

In an alternate embodiment, handle 402 may be an integral part of extension member 404 and member holder 408', as depicted in FIG. 15. Body 406 of spreader 400 may be coupled to second member holder 408", as depicted in FIG. 16. First member holder 408' may be an integral part of body 406.

As shown in FIG. 13 and FIG. 14, body 406 of spreader 400 may include a pair of channel members 412. Sets of holes 414 and slots 416 may be formed in channel members 412. Holes 414 may allow first member holder 408' to be integrally attached to body 406 of spreader 400. First member holder 408' may be attached by pins 418 between channel members 412 so that the first member holder is an integral part of body 406. Pins 418 may be press-fit through holes 414 of body 406 into first member holder 408'. Slots 416 allow second member holder 408" to be attached by pins 418 between channel members 412. Pins 418 may be press-fit through slots 416 of body 406 into second member holder 408". Slots 416 allow second member holder 408" to move relative to body 406 and first member holder 408' when the second member holder is attached to the body. Slots 416 may allow second member holder 408" to move laterally towards or away from first member holder 408'. Axial movement of first member holder 408' and second member holder 408" towards a distal or proximal end of spreader 400 is inhibited.

As shown in the spreader embodiment depicted in FIG. 16, pins 418 may be press-fit through slots 416 in body 406 into member holder 408'. Pins 418 may attach second member holder 408" to body 406 so that the second member holder is able to move laterally relative to first member holder 408'.

A separation distance between inner surfaces of channel members 412 (depicted in FIG. 13, FIG. 14, and FIG. 16) may be slightly larger than a width of a separator, such as separator 300 depicted in FIG. 11. The separation distance between channel members 412 may inhibit lateral and rotational movement of a separator positioned within spreader 400. The separation distance between channel members 412 may also promote proper alignment of connector passages 306 of separator 300 with tapered slots in implant members that are coupled to member holders 408 of spreader 400.

Spreader 400 may include depth indicators 420, as depicted in FIG. 13 and FIG. 14. Depth indicators 420 may be, but are not limited to, slots, shoulders, extensions, depressions, and/or indicia in handle 402 and/or extension portion 404 of spreader 400. In alternate embodiments, depth indicators may be positioned at other locations of spreader 400. Depth indicators 420 may be used in association with a depth gauge, such as depth gauge 800 depicted in FIG. 26, to indicate when a connector is inserted to a desired depth within implant members.

Some spreader embodiments may include indicia 422 located near a distal end of spreader 400. Indicia 422 may be etched, printed, adhered, or otherwise placed on spreader 400. FIG. 13 and FIG. 14 depict indicia 422 on member holders 408. Indicia 422 may be a scale that indicates insertion depth of implant members attached to implant holders 408 between vertebrae or bone segments in a length unit (e.g., millimeters).

Figure 17:
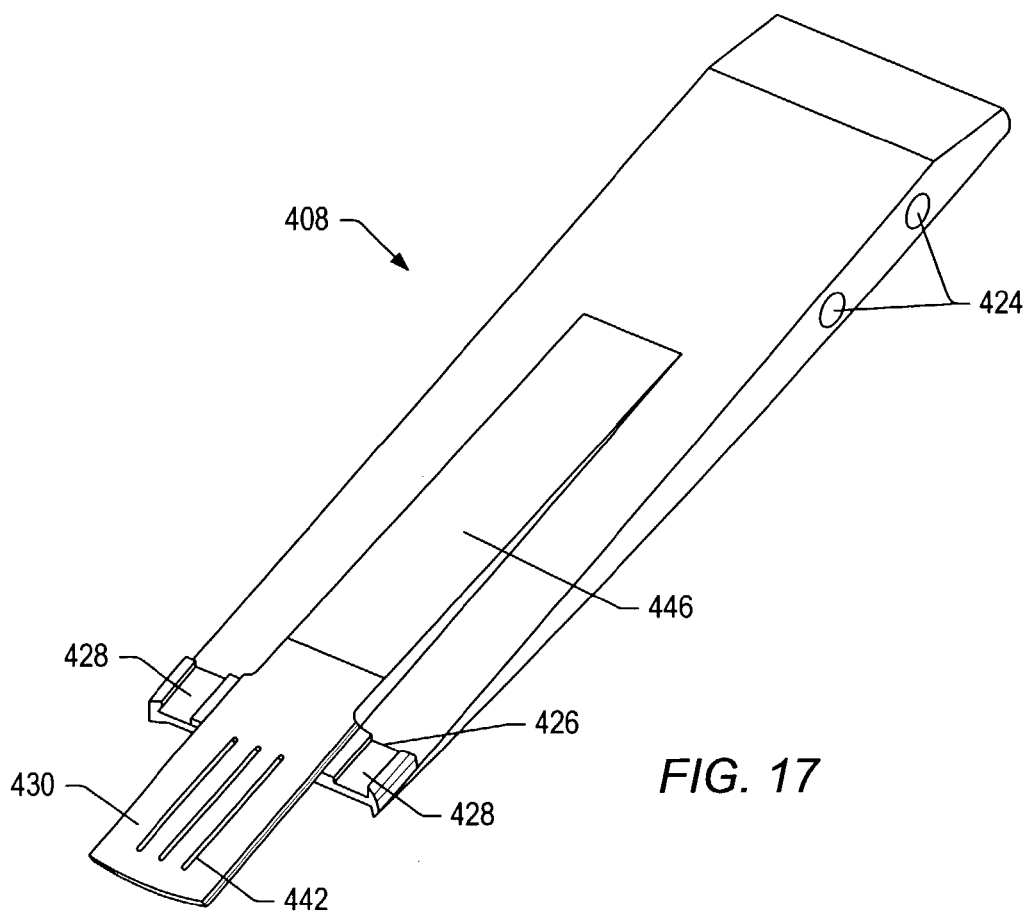
FIG. 17 shows a perspective view of an embodiment of an inner surface of a member holder.
Figure 18:
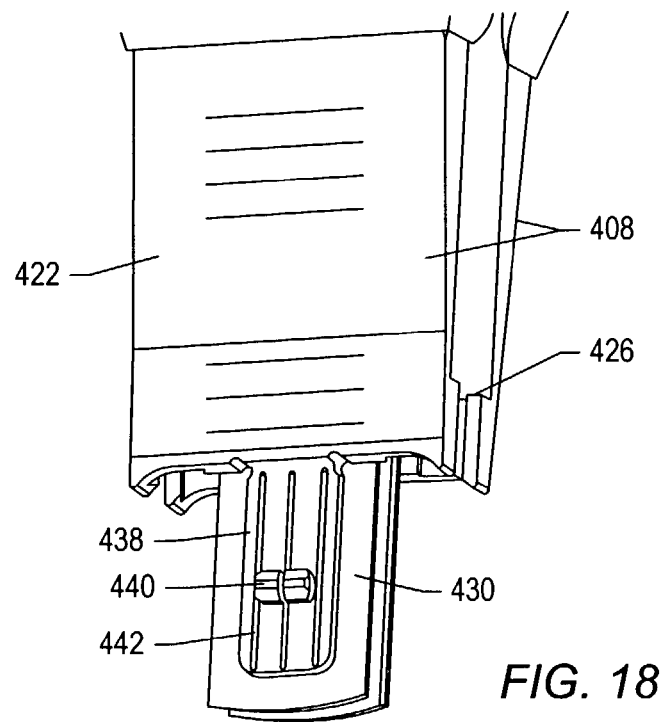
FIG. 18 shows a perspective view of a portion of an embodiment of a spreader that emphasizes a front view of a member holder.
Figure 19:
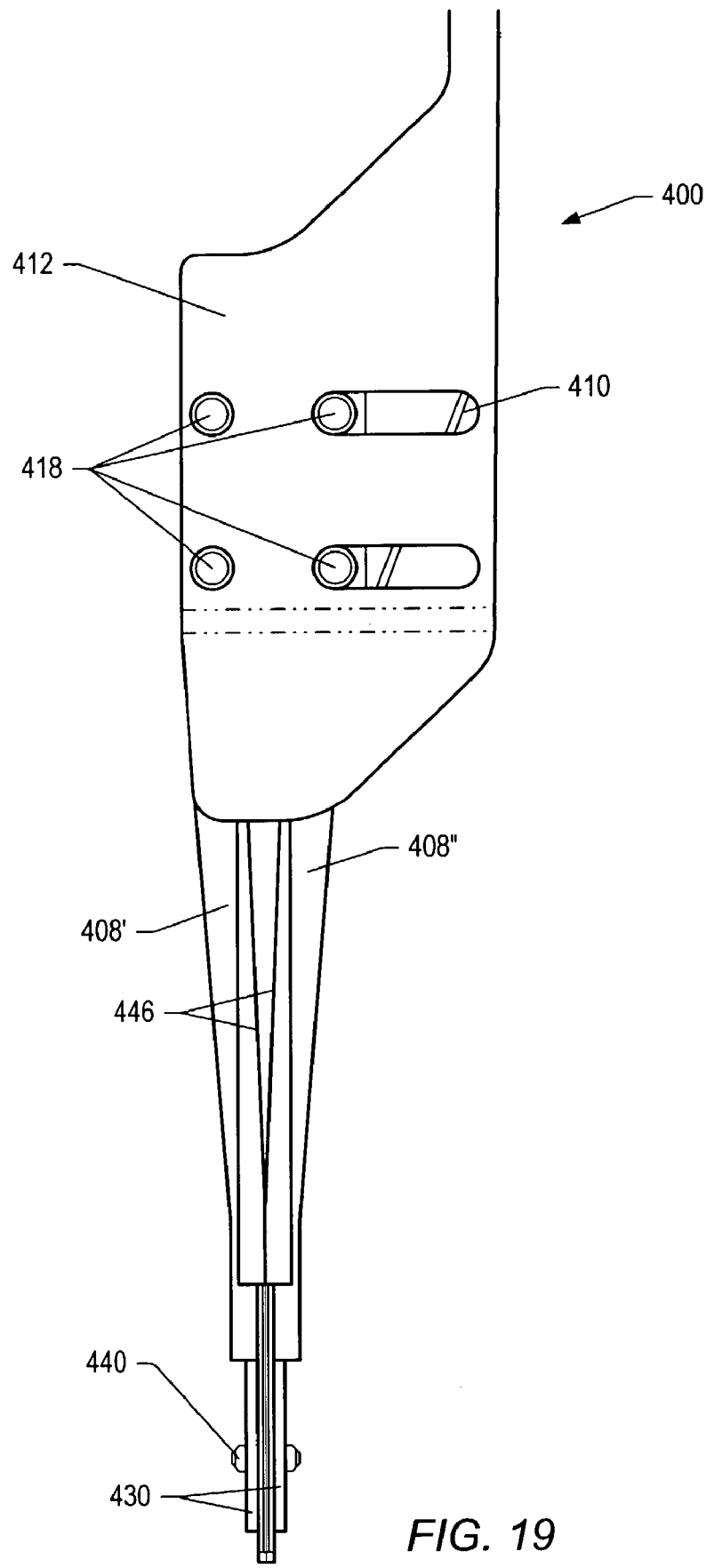
FIG. 19 shows a side view of a portion of an embodiment of a spreader.

FIG. 17 depicts a perspective view that emphasizes inner surfaces of an embodiment of member holder 408. Member holder 408 may include openings 424, shoulders 426, connector guide slots 428, and member mounts 430. FIG. 18 shows a perspective view of a portion of an embodiment of member holder 408 that emphasizes an outer surface of the holder. FIG. 19 shows a side view of a portion of an embodiment of spreader 400.

Openings 424 (shown in FIG. 17) may be sized slightly smaller than ends of pins 418 (shown in FIG. 13). Pins 418 may be press-fit into openings 424 to join member holder 408 to body 406 of spreader 400.

Shoulders 426 of member holder 408 may limit insertion depth of a separator into a spreader. Stop surface 308 of separator 300 (depicted in FIG. 12) may contact shoulders 426 of member holders 408 when the separator is inserted into the spreader.

Connector guide slot 428 (shown in FIG. 17) may have a shape complementary to the shape of a portion of an implant connector, such as connector 14 depicted in FIG. 7. When a separator is fully inserted into a spreader, the ends of connector passages through the separator may abut and align with connector guide slots 428 in member holders 408. A connector inserted into the connector passage of the separator may pass through the separator, through connector guide slots 428 of member holders 408, and into tapered slots of implant members that are coupled to the member holders.

Separator depth indicia 422 on member holders 408 of a spreader, for example, the spreader shown in FIG. 18, may be hidden from view when a separator is initially positioned between member holders of the spreader. Separator depth indicia 422 may become visible when the separator is fully inserted in the spreader. The visibility of separator depth indicia 422 will indicate to a surgeon that the separator is fully inserted into the spreader. Separator depth indicia 422 may be edges of the member holders, indentions, etchings, coloring, and/or other types of markings. For example, in FIG. 17, surface 434 may be silver and surface 436 may be gold. When a separator is placed between the member holders of an assembled spreader, the surgeon will initially only see gold surface 436. When the surgeon inserts the spreader to a proper depth, a portion of silver surface 434 will be visible and will indicate to the surgeon that the separator is inserted to a proper depth in the spreader.

As depicted in FIG. 18, mount 430 of member holder 408 may include raised surface 438, engagers 440, and slots 442. Raised surface 438 may be complementary to recess 38 of implant member 12 so that motion of the implant member is inhibited relative to the member holder when the implant member is coupled to the member holder. An embodiment of implant member 12 with recess 38 is depicted in FIG. 5. Engagers 440 may fit within opening 28 in implant member 12. Opening 28 may be a central opening within implant member 12. Slots 442 may allow portions of mount 430 to deflect so that engagers 440 may be press-fit onto implant member 12. A plurality of slots 442 that do not extend to an end of member holder 408 may inhibit change in the spring properties of member holders 408 adjacent engagers 440 that may be caused by dropping or rough handling of spreader 400. In an alternate member holder embodiment, such as member holder 408 depicted in FIG. 15, mount 430 may include single slot 442 in communication with an end of the member holder. Single slot 442 may be compressed to allow an opening of an implant member to be press fit onto an engager of the member holder.

When implant members are press-fit onto member holders 408, tapered slots of the implant members may abut and align with connector guide slots 428 of the member holders, as depicted in FIG. 17. A connector may be able to pass through connector guide slots 428 into the tapered slots of the implant members to connect the implant members together.

Spreader 400 may include spring member 410. As depicted in FIG. 14, spring member 410 may be rigidly attached to extension portion 404. Spring member end 444 may contact second member holder 408". Spring member 410 may apply a force to second member holder 408" through end 444. The force may push second member holder 408" towards first member holder 408'. Without a separator positioned between member holders 408, the spring member may place the member holders in an initial position, as depicted in FIG. 14. When spreader 400 is in the initial position, there may be substantially no separation distance between mounts 430 of member holders 408. Inserting a separator between member holders 408 may move second member holder 408" away from the initial position.

FIG. 19 depicts a side view of a portion of a spreader embodiment. Member holders 408 are shown in an initial position. Member holders 408 may include sloped surfaces 446. Sloped surfaces 446 may establish a separation distance between member holders 408 when spring member 410 forces member holder 408" to the initial position. The separation distance allows a separator to be inserted between member holders 408. Spreader contact surfaces, such as spreader contact surfaces 320 of separator 300 depicted in FIG. 11, may contact sloped surfaces 446 of spreader 400.

Sloped surfaces 446 may allow a separator to gradually increase a separation distance between the implant members coupled to member holders 408 as the separator is inserted between the member holders. Sloped surfaces 446 may allow a large component of force applied to the separator to be transferred to member holders 408 in a direction substantially normal to the insertion direction. The force applied to member holders 408 may increase the separation distance between the member holders so that implant members coupled to the member holders establish a desired separation distance between vertebrae or bone segments.

Figure 20:
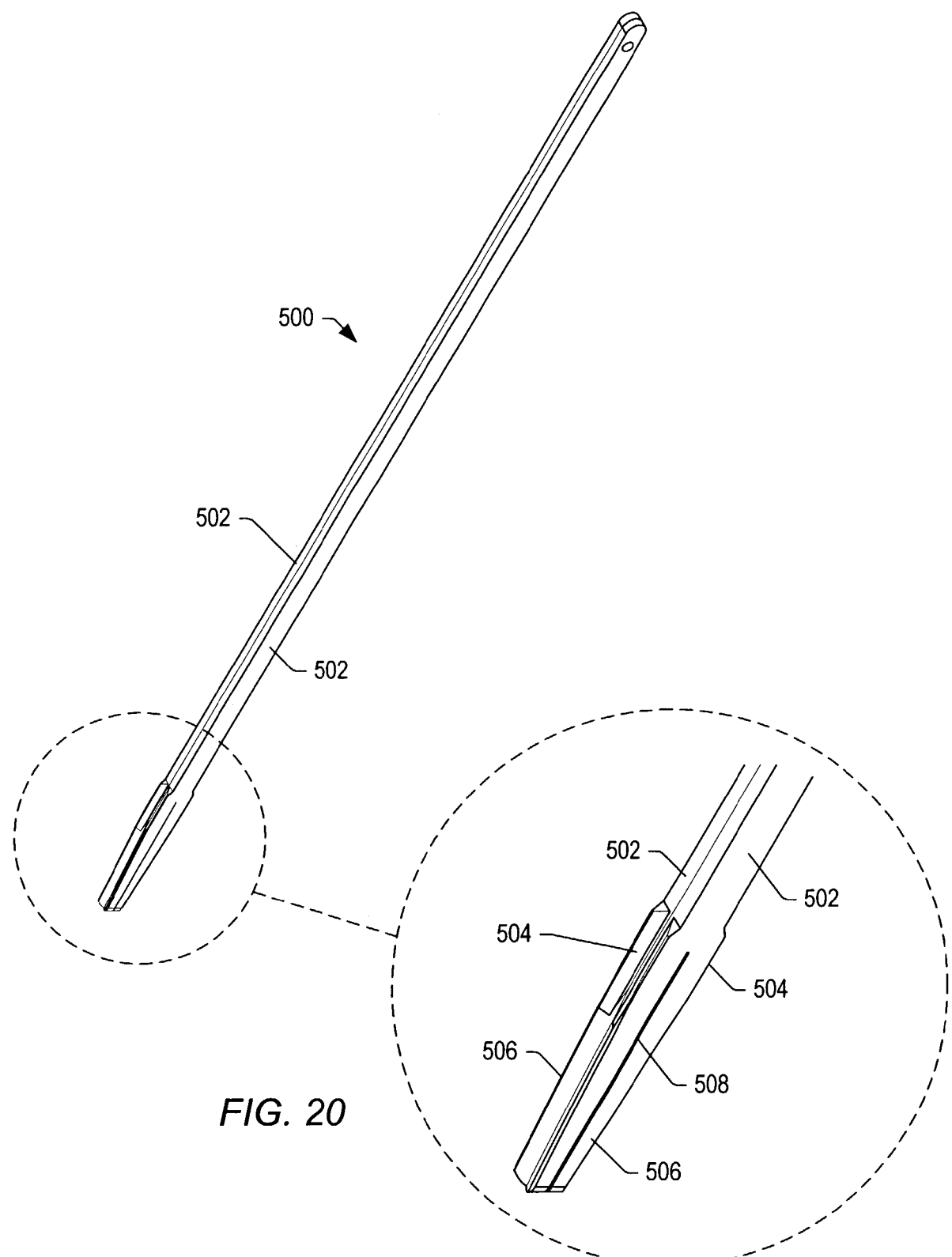
FIG. 20 shows a perspective view of an embodiment of a locking pin with a detail of a tip of the locking pin.

FIG. 20 shows a perspective view of an embodiment of locking pin 500. Locking pins 500 may secure implant members to a spreader. Locking pins 500 may also serve as guides for insertion of a separator between member holders of the spreader. Locking pin 500 may include legs 502 that are joined together at a top end of the locking pin. Legs 502 of locking pin 500 may be inserted through connector guide slots of spreader member holders and into tapered slots of a pair of implant members that are coupled to the spreader. Connector guide slots 428 of spreader 400 are depicted in FIG. 13. Tapered slots 32 of implant member 12 are depicted in FIG. 5.

End portions of each leg 502 may include wide portions 504, tapered portions 506, and compression slot 508. Wide portions 504 may be sized to engage walls of connector guide slots of a spreader. Wide portions 504 may slide into or out of the connector guide slots in directions parallel to a longitudinal axis of the guide slots. Dovetail connections between wide portions 504 and the guide slots may inhibit removal of the wide portions from the guide slots in directions that are not parallel to the longitudinal axis of the guide slots.

Tapers of tapered portions 506 of locking pins 500 may substantially correspond to the taper of implant member tapered slots. Tapered portions 506 may form a dovetail connection with implant member tapered slots that allows removal of the tapered portions from the tapered slots only in a direction opposite to an insertion direction. Insertion of tapered portions 506 into the tapered slots of implant members may reduce a separation distance between portions of locking pin 500 that define compression slot 508. Reduction of the separation distance generates a force applied by locking pin legs 502 to the implant members. The force secures locking pin legs 502 to the implant members.

When locking pin 500 is inserted into a spreader and into implant members coupled to the spreader, some of wide portions 504 of each leg 502 may be positioned in a tapered slot of an implant member and some of wide portions 504 of each leg may be positioned in a connector guide slot of the spreader. When implant members are press-fit on member holders, tapered slots of the implant members may align and abut with connector guide slots of the spreader. Locking pins 500 may maintain the abutted and aligned positions of the implant members relative to the member holders of the spreader.

Locking pins 500 may secure implant members to a spreader prior to insertion of the spreader into a patient. The connections between the implant members, spreader, and locking pins may be visually checked prior to insertion of the spreader into the patient. A physical check of the connections between the implant members, spreader, and locking pins 500 may be performed by inserting the locking pins and then turning the spreader upside down. Force applied to the implant members by locking pins 500 due to reduction of compression slot 508 should be sufficient to hold the locking pins in position even when the spreader is turned upside down. Locking pins may be removed from the spreader and implant members by grasping the locking pins and pulling the locking pins in a direction opposite to an insertion direction.

A spreader may be positioned between vertebrae or bone segments after locking pins 500 are positioned to securely couple implant members to the spreader. A separator may then be inserted into the spreader to allow the implant members to distract the vertebrae or bone segments to a desired separation distance. An extender may be attached to the separator to facilitate placement and insertion of the separator into the spreader.

Figure 21:
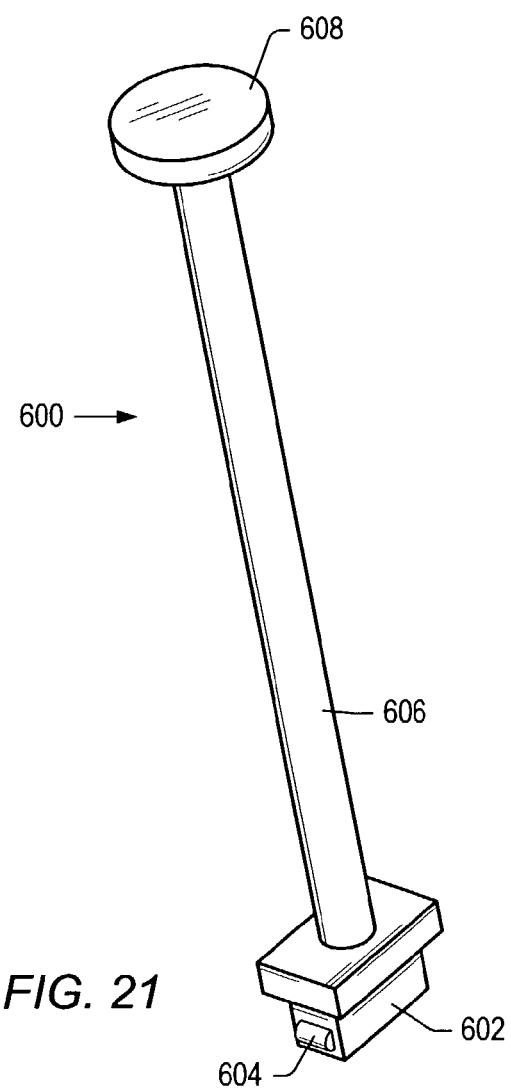
FIG. 21 shows a perspective view of an embodiment of an extender.
Figure 22:
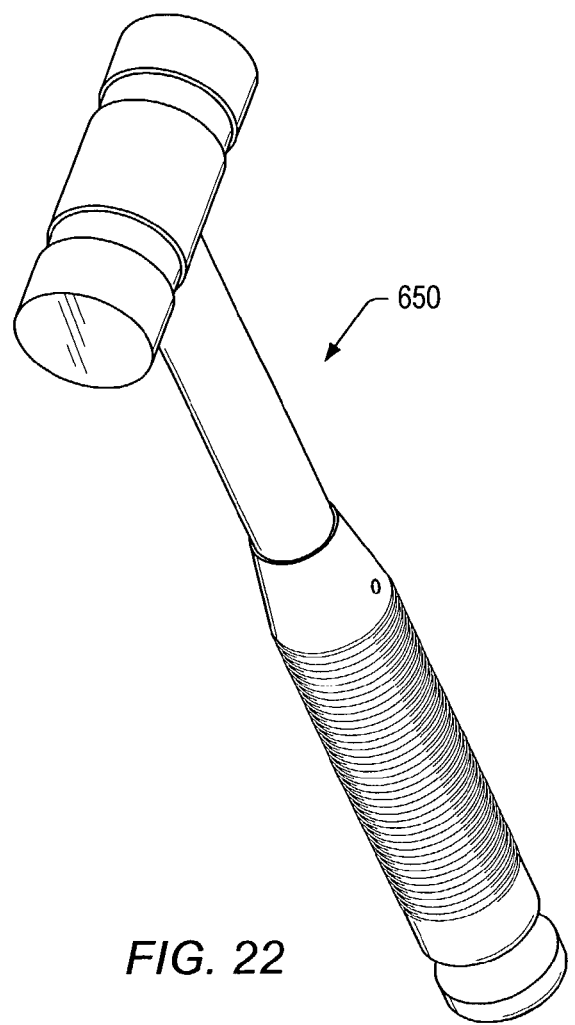
FIG. 22 shows a perspective view of an embodiment of a mallet.

An extender embodiment is depicted in FIG. 21. Extender 600 may be coupled to a separator, such as separator 300 depicted in FIG. 12. Extender 600 may include end 602, detents 604, shaft 606, and impact surface 608. A portion of end 602 may fit in attachment mount 304 of separator 300. Detents 604 may engage separator surface 318. Internal springs may extend detents 604 with enough force so that the detents support the weight of the separator, but without enough force to make removing extender 600 from the separator difficult. A portion of end 602 may overlap a portion of a top surface of the separator so that impact force applied by a mallet or other instrument to impact surface 608 will drive the separator into the spreader. FIG. 22 depicts an embodiment of mallet 650 that may be used to insert instruments. Shaft 606 may provide extender 600 with enough length to allow a separator that is attached to the extender to be manipulated from above an opening in a patient. Manipulating the separator from above the opening may allow for good visibility of positioning and placement of the separator.

Extender 600 may allow a separator to be positioned so that locking pins are positioned through passages of the separator and so that the spreader contact surfaces of the separator contact sloped surfaces of the spreader. An impact instrument, such as a mallet, may apply force to impact surface 608 that drives the separator into the spreader until the stop surface of the separator contacts shoulders of the member holders. After the separator is inserted into the spreader, extender 600 may be removed from the separator by holding the separator in position and pulling the extender upwards. During some procedures, a slap hammer or other device may be used to insert the separator into the spreader. When the separator is driven into the spreader, implant members connected to the spreader are separated a desired separation distance. Driving the separator into the spreader may drive protrusions of the implant members into adjacent bone.

Figure 23:
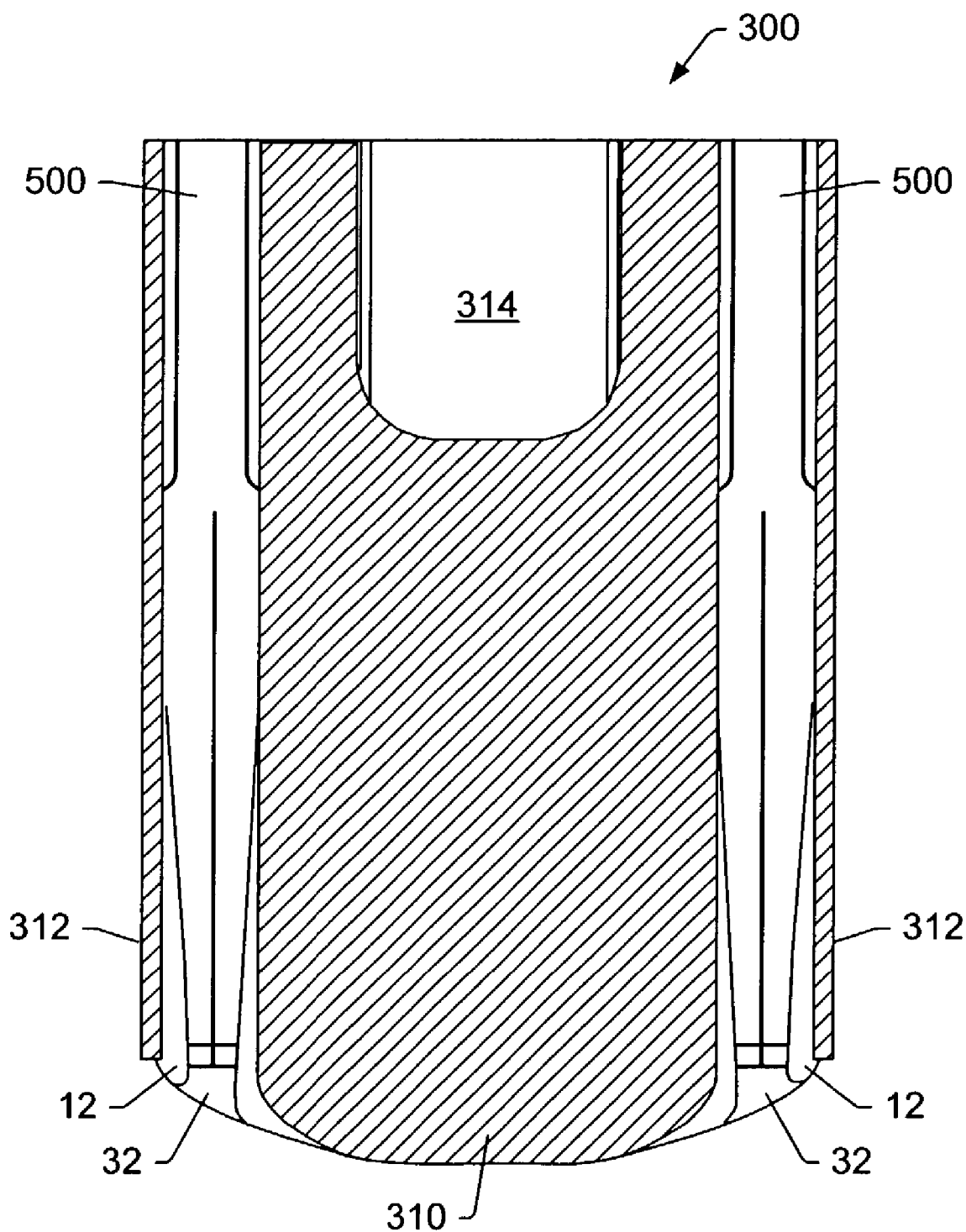
FIG. 23 shows a partial view of an embodiment of a spreader, separator, implant member, and locking pin combination, wherein the depicted portion of the separator is shown in cross section.

FIG. 23 depicts a representation of locking pins 500 positioned in tapered slots 32 of implant member 12 that is press-fit onto a spreader. Locking pins 500 extend through separator 300. Tongue 310, arms 312, and central opening 314 of separator 300 are shown in cross section.

After separator 300 is fully inserted into a spreader, locking pins 500 may be removed from the separator by grasping the locking pins and pulling the locking pins in a direction opposite to an insertion direction.

Figure 24:
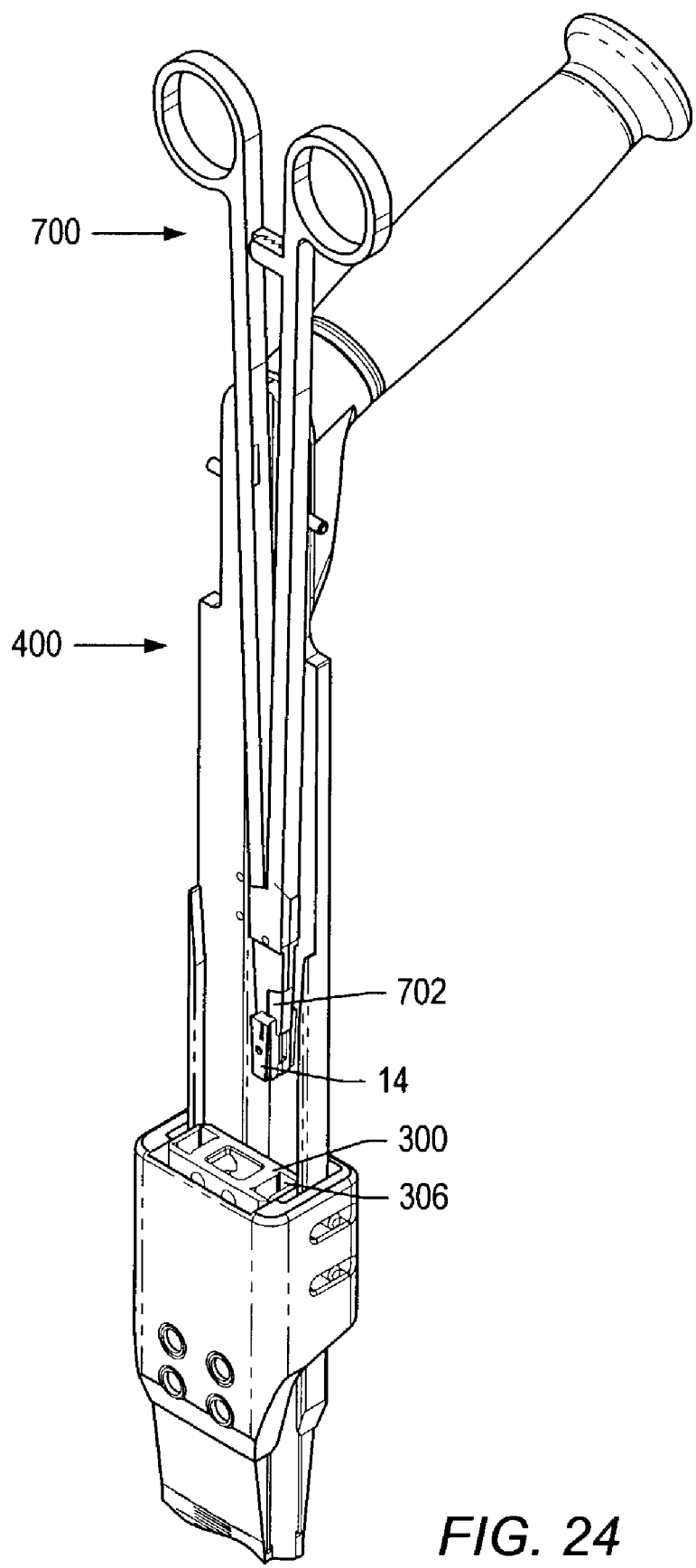
FIG. 24 shows a partial perspective view of an embodiment of a spreader and separator combination prior to release of a connector into a connector passage of the separator.

Connectors may be inserted through connector passages 306 of separator 300 (shown in FIG. 12), through guide slots 428 of spreader 400 (shown in FIG. 13), and into tapered slots of implant members press-fit onto the spreader. FIG. 24 depicts a partial representation of separator 300 inserted into spreader 400 with connector 14 positioned to be released into connector passage 306 of the separator. Connector 14 may be attached to forceps 700 and dropped into connector passages 306 of separator 300. Grasping ends 702 of forceps 700 may accept a wide end of connector 14, but not a narrow end of the connector. When forceps 700 are fully closed, a narrow end of connector 14 may not be held by ends 702 of the forceps. The ability to grasp the wide end of connector 14 with the forceps, but not the narrow end, may ensure that connectors are in a proper orientation before being released into connector passages 306 of separator 300.

Figure 25:
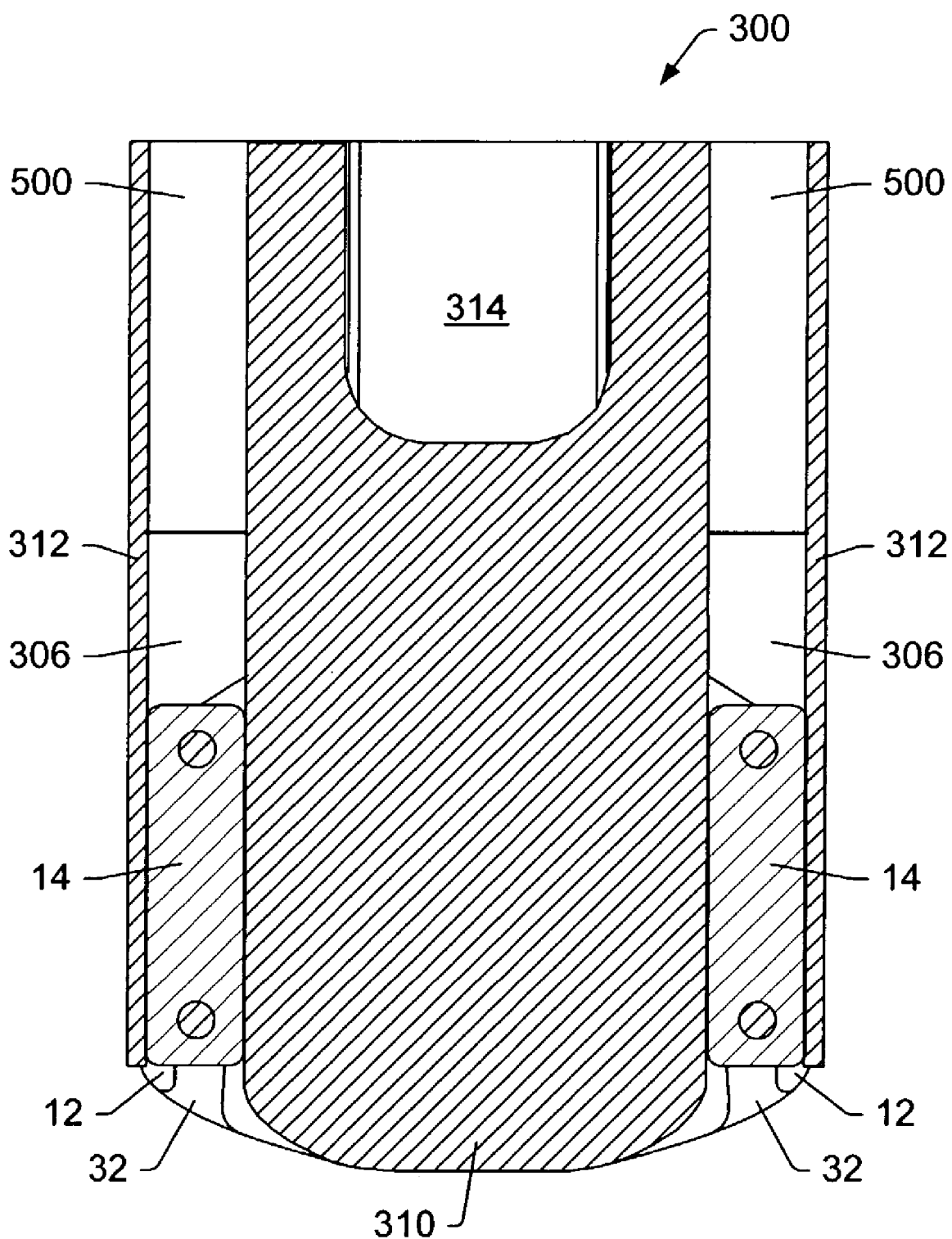
FIG. 25 shows a partial view of an embodiment of a spreader, separator, implant member, and connector combination, wherein the depicted portions of the connectors and separator are shown in cross section.

FIG. 25 depicts a representation of connectors 14 positioned in tapered slots 32 of implant members 12 that are press-fit onto a spreader. After insertion of connectors 14 into tapered slots 32 of implant members, a depth gauge may be used to drive the connectors to a desired depth within the tapered slots of implant members. Connector passages 306, tongue 310, arms 312, and central opening 314 of separator 300 are shown in cross section.

Figure 26:
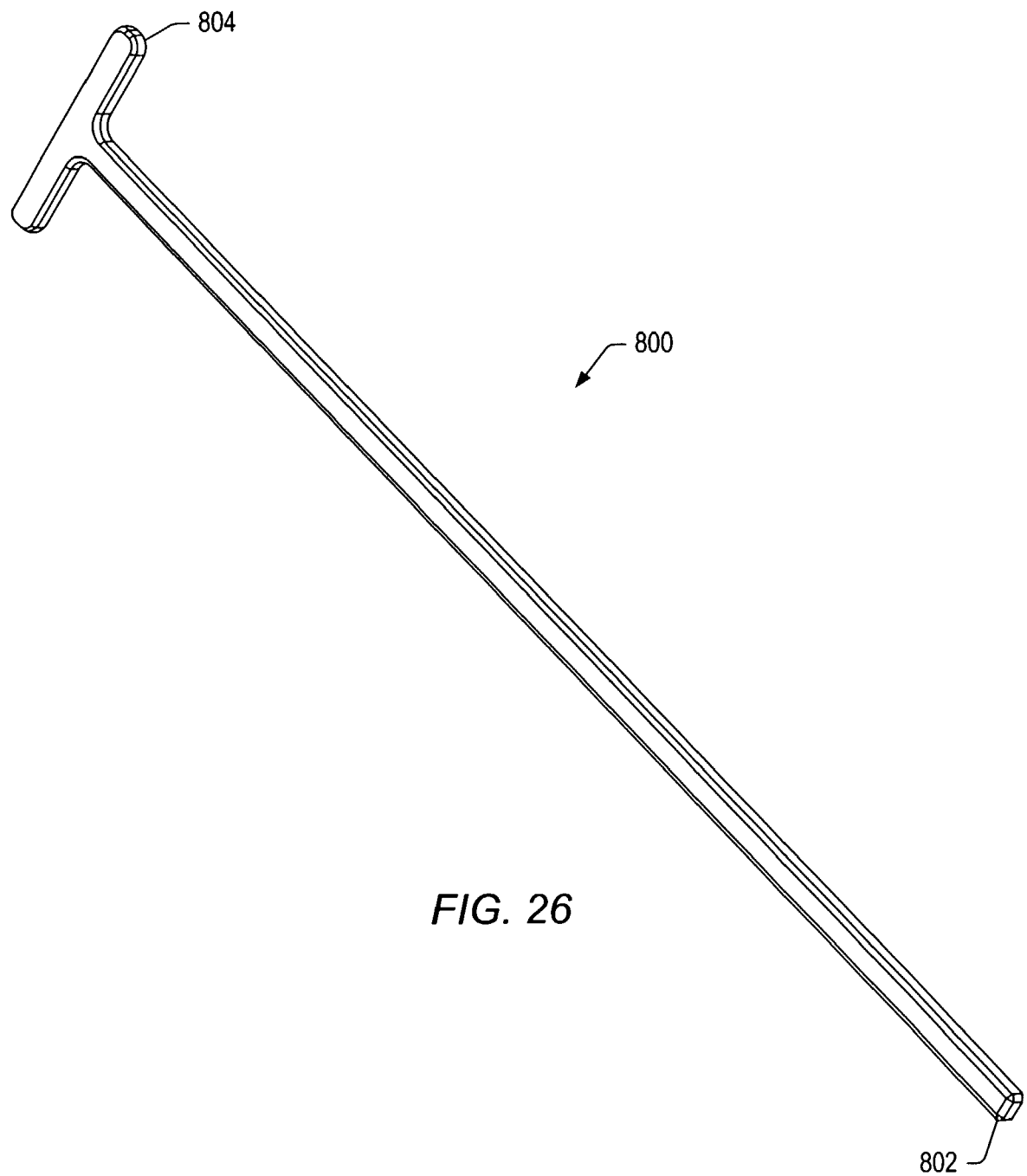
FIG. 26 shows a perspective view of an embodiment of a depth gauge.

FIG. 26 depicts an embodiment of depth gauge 800 that may be used to drive connectors to proper depths within tapered slots of implant members. End 802 may be placed through connector passages of a separator to contact connectors positioned between implant members. Depth gauge 800 may be driven downwards until handle 804 interacts with a depth indicator of a spreader, such as depth indicator 420 of spreader 400 depicted in FIG. 13. Depth gauge 800 may be used on each connector to ensure that the connectors are inserted to the proper depth. Hand pressure against handle 804 should be sufficient to drive a connector to the proper depth between implant members. If needed, an impact instrument may be tapped against handle 804 to insert a connector to the proper depth.

After insertion of the connectors, a separator may be removed from a spreader. A slap hammer may be attached to an attachment mount of the separator. The slap hammer may be used to remove the separator from the spreader.

Figure 27:
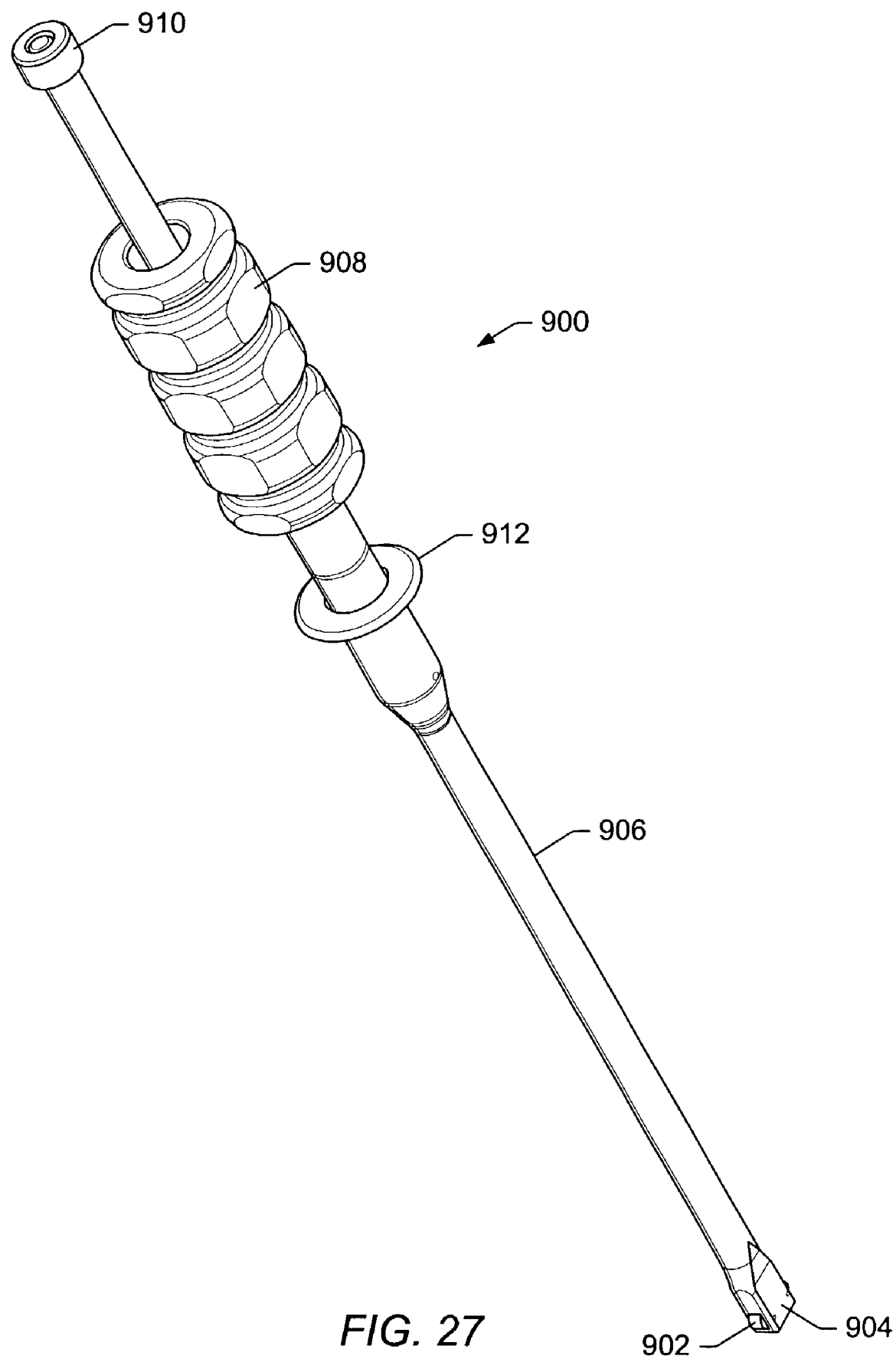
FIG. 27 shows a perspective view of an embodiment of a slap hammer.

FIG. 27 depicts an embodiment of slap hammer 900 that may be used to remove a separator from a spreader. Slap hammer 900 may include detents 902, insertion portion 904, shaft 906, slide 908, upper stop 910, and activator 912. Insertion portion 904 may fit within an attachment mount of a separator, such as attachment mount 304 of separator 300 depicted in FIG. 12. Activator 912 may be pulled towards slide 908 to allow detents 902 to move inward within insertion portion 904 so that the insertion portion may be placed in the attachment mount of the separator. After placement of insertion portion 904 in the separator attachment mount, activator 912 may be released to extend detents 902 out of insertion portion 904 and affix slap hammer 900 to the separator. Slide 908 may be grasped and repeatedly impacted against upper stop 910 to remove the separator from the spreader. In addition to removing a separator from a spreader, slap hammer 900 may be used to insert a separator into a spreader. In some embodiments, slap hammer 900 may be used to position, insert, and/or remove other instruments that have attachment mounts that are complementary to insertion portion 904 of the slap hammer.

Figure 28:
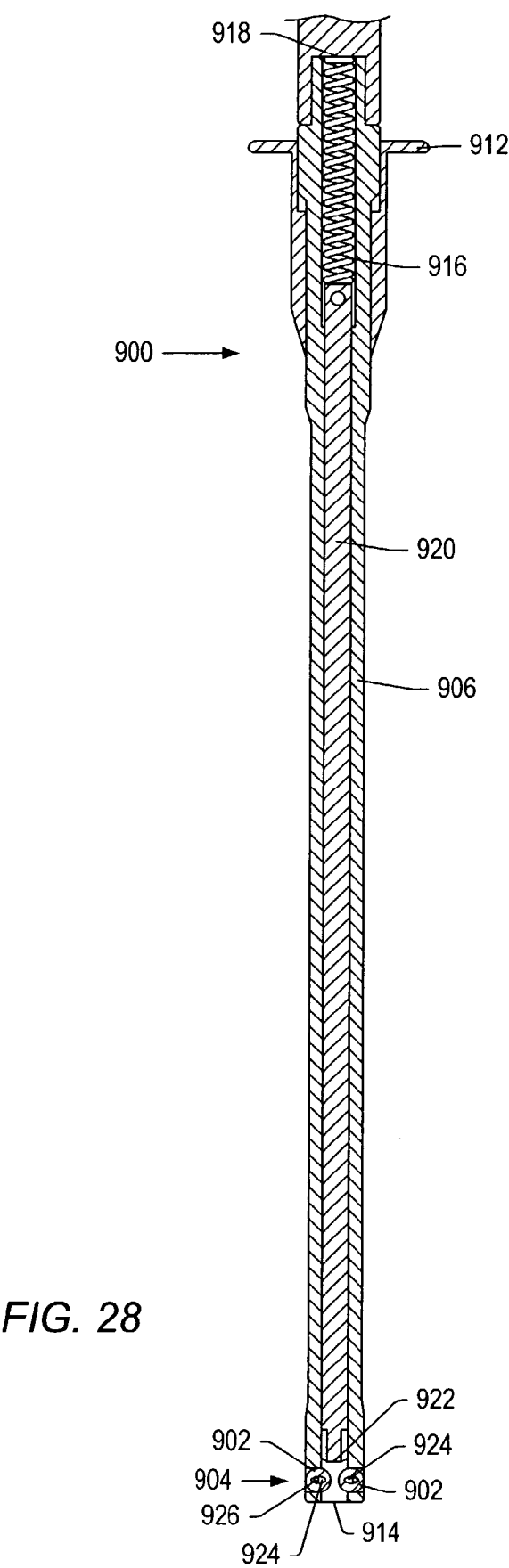
FIG. 28 shows a cross-sectional representation of a portion of a slap hammer.

FIG. 28 depicts a cross-sectional representation of a slap hammer embodiment that has cylindrical detents 902. Cylindrical detents may provide a large contact surface for engaging an instrument attached to the slap hammer. In other embodiments, detents may be spherical, hemispherical, or have other shapes. Slap hammer 900 is depicted in a position where activator 912 is pulled away from end 914 of the slap hammer so that spring 916 is compressed against spring stop 918 of shaft 906. Rod 920 is drawn up in shaft 906 so that end 922 of the rod does not engage detents 902. Detent slots 924 may be placed over pins 926. Slots 924 allow detents 902 to move into or out of insertion portion 904. When activator 912 is pulled up, as depicted in FIG. 28, detents 902 are free to move within insertion portion 904, and slap hammer 900 may be placed in or be removed from an attachment mount of an instrument. When activator 912 is released, spring 916 will uncompress and force rod 920 towards end 914 of slap hammer 900. Rod 920 may contact detents 902 and force the detents to extend outside of insertion portion 904. When activator 912 is released so that spring 916 extends rod 920 such that the rod is adjacent to detents 902, the rod will inhibit movement of the detents relative to insertion portion 904.

After removal of a separator from a spreader, the spreader may be disengaged from implant members. Twisting the spreader relative to the implant members may release the press-fit connection between the implant members and the spreader. The spreader may then be removed from the patient. Implant members that are joined together by connectors may be left in a disc space between vertebrae or within an opening between bone segments. A connector seater may subsequently be used to affix the connectors to the implant members.

Figure 29:
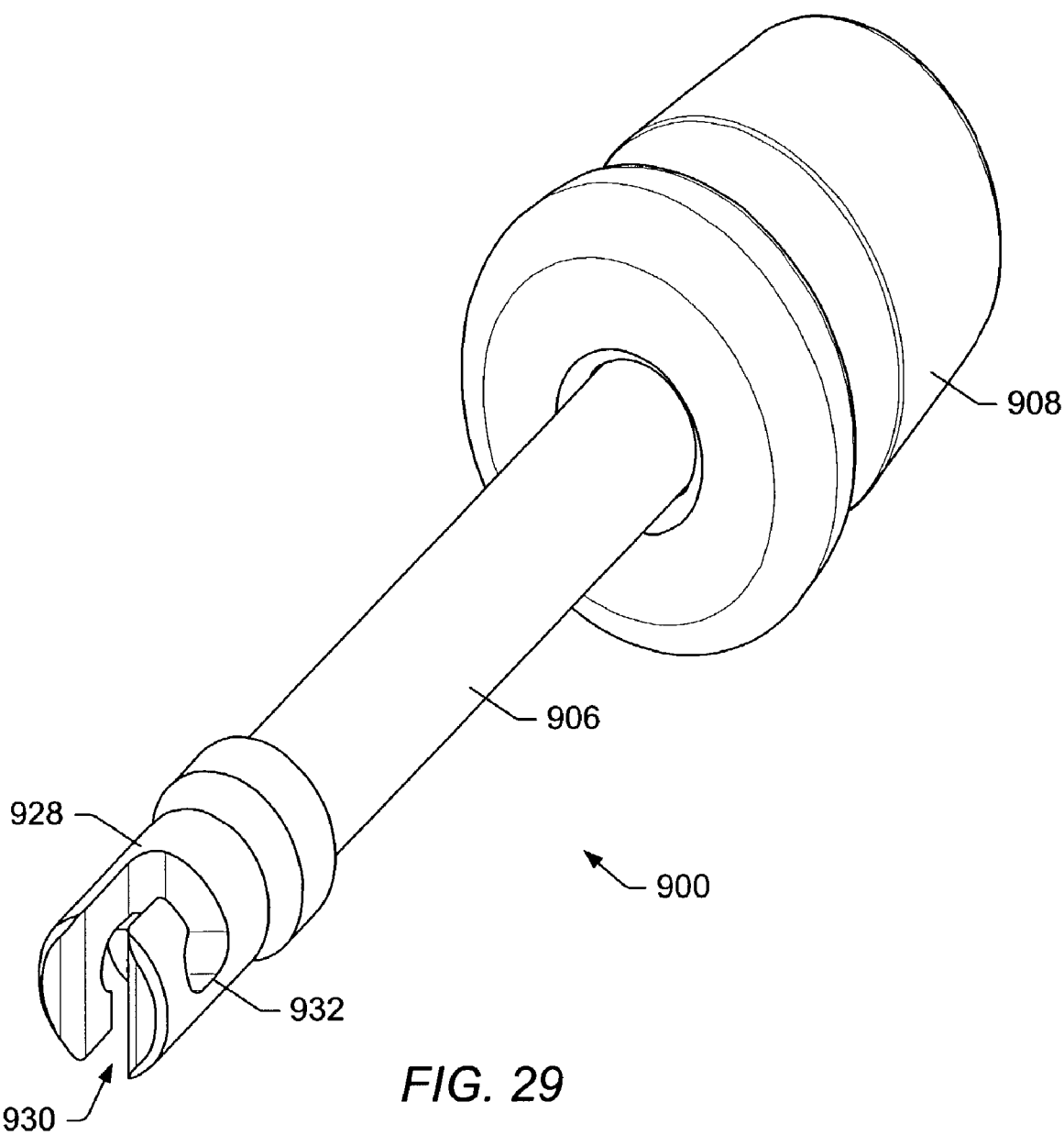
FIG. 29 shows a perspective view of a portion of a slap hammer embodiment.

FIG. 29 depicts a perspective view of a portion of an embodiment of slap hammer 900. Slap hammer 900 may include end connector 928. End connector 928 may include slot 930 and holder 932. A rod in a spreader, or other instrument that is to be used with slap hammer 900, may fit in slot 930. Slap hammer 900 may be rotated about 90° to place the bar in holder 932. Slide 908 may be grasped and repeatedly impacted against an upper stop 910 during use of slap hammer 900.

Figure 30:
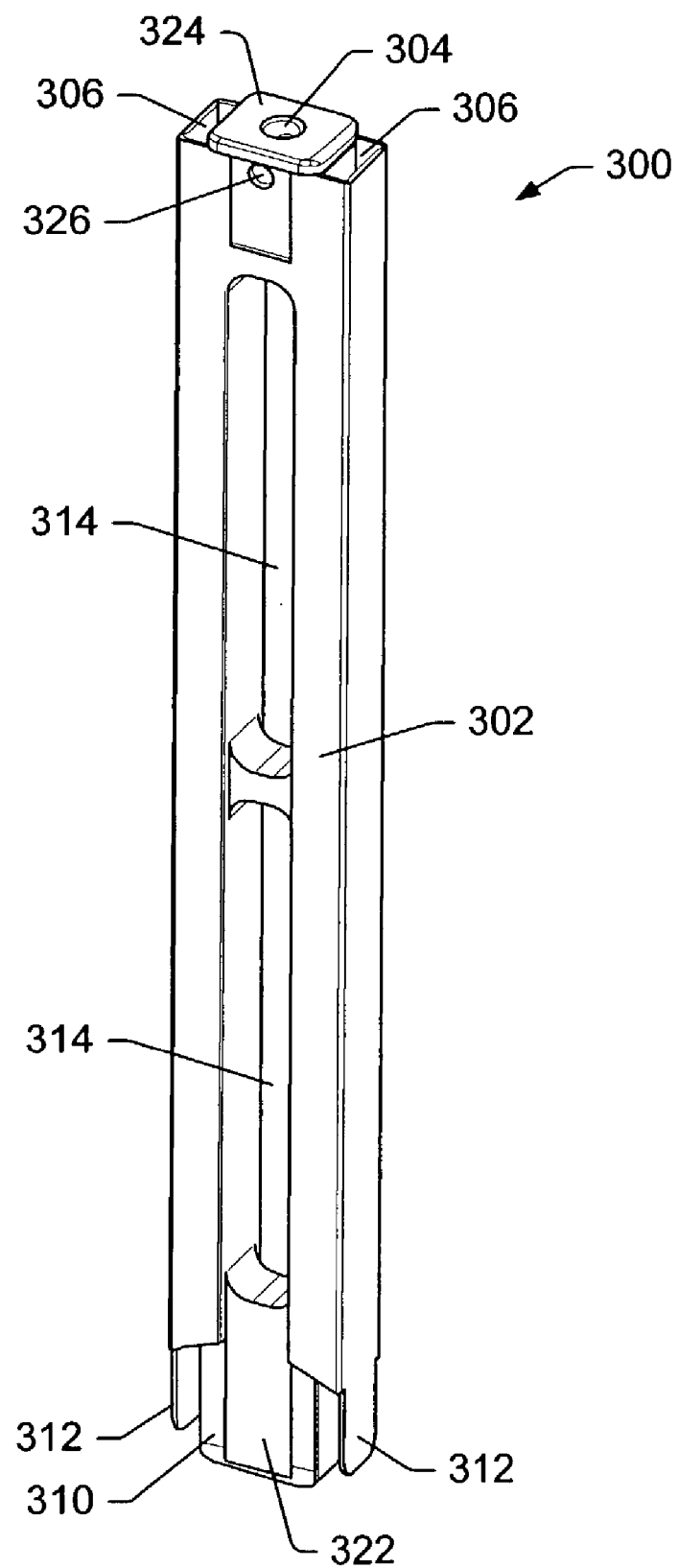
FIG. 30 shows a perspective view of an embodiment of a separator.
Figure 31:
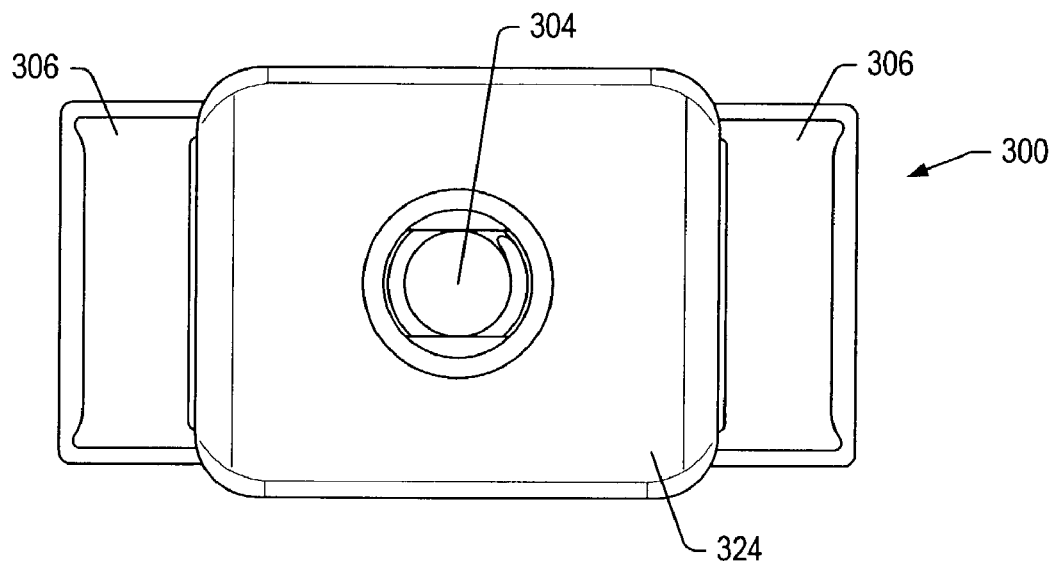
FIG. 31 shows a plan view of an embodiment of a separator.

FIG. 30 and FIG. 31 show various views of embodiments of separators 300. Separator 300 with body 302 may include tongue 310, arms 312, central openings 314, and groove 322 for aligning separator 300 with a spreader, such as spreader 400 depicted in FIG. 36. Groove 322 may guide separator 300 between implant members attached to member holders of spreader 400 during a spinal fusion procedure. Separator 300 may include impact surface 324. Separator 300 may include indention 326 for coupling to spreader retention mechanisms. Indention 326 may be configured to accept a portion of a spreader retention mechanism to inhibit movement of separator 300 when the separator is inserted into spreader 400. Indention 326 may be an opening through separator 300. The opening may intersect attachment mount 304. Detents of an impact instrument, such as a slap hammer, may engage a surface that defines the opening to couple the impact instrument to separator 300.

During a fusion procedure, a mallet (such as mallet 650 depicted in FIG. 22) or other impact instrument may be used to insert a separator into a spreader positioned between vertebrae or bone segments that are to be fused together. Impact surface 324 of separator 300 may be impacted to drive the separator into a spreader, such as spreader 400 depicted in FIG. 36. A slap hammer may be used to remove separator 300 and other insertion instruments from a patient. The slap hammer may be connected to attachment mount 304 prior to use.

As depicted in FIG. 31, connector passage 306 may have a shape that substantially corresponds to a shape of a connector. A properly sized connector may slide through connector passage 306. A wide end of a connector (e.g., connector 14 shown in FIG. 7) may be color-coded and/or include indicia that inform a user which end of the connector is the wide end. During insertion of connector 14 into connector passage 306 of separator 300 (shown in FIG. 30 and FIG. 31), the color-code or indicia may inform a user if the connector is oriented in the proper direction. For example, the wide end of a connector may be stamped with a "W". If the "W" is visible prior to the connector being released into passage 306, the user will know that the connector is being inserted in the proper orientation. In some embodiments, a narrow end of connector 14 may be color-coded and/or include indicia that informs a user that the connector is about to be inserted improperly. For example, the narrow end of a connector may be color-coded red. If the red color is visible prior to the connector being released into passage 306, the user will know not to release the connector into the passage.

Connector passages 306 through a separator may be adapted to accommodate a specific size of connector. For example, passage 306 may be sized to allow a connector that will form an implant with about a 12 mm separation distance between outer surfaces of implant members to pass through the separator. An instrumentation set for an implant fusion procedure may include a separator for each implant member size included in the instrumentation set. The separators may have connector passages 306 of different sizes to allow for formation of implants having different heights. For example, an instrumentation set may include separators for forming implants ranging in size from about 8 mm implants to about 24 mm implants in approximately 2 mm increments. Connectors for each size of separator may also be supplied with the instrumentation set.

Figure 32:
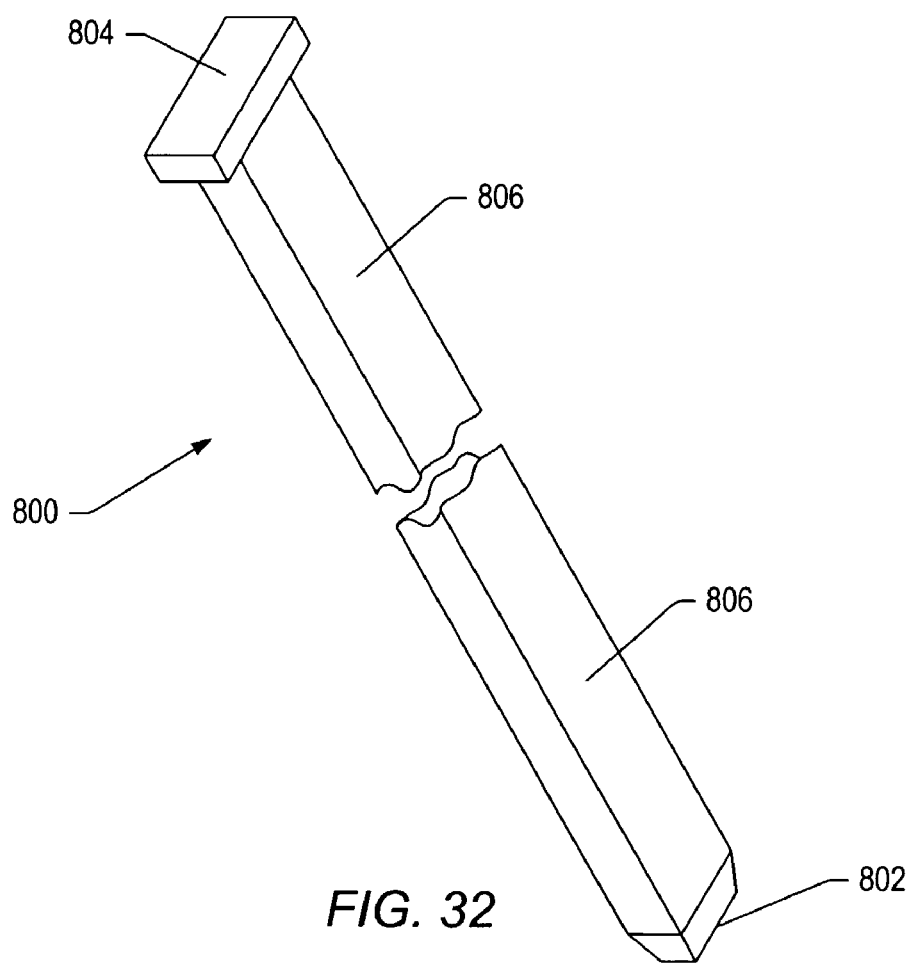
FIG. 32 shows a perspective view of an embodiment of a depth gauge.

FIG. 32 depicts an embodiment of depth gauge 800 that may be used with separator 300 depicted in FIG. 30. Depth gauge 800 may include shaft 806 that fits within connector passages 306 of separator 300. Depth gauge handle 804 may be larger than connector passages 306. Depth gauge handle 804 may engage shoulders of a spreader that the separator is inserted into. Connectors may be inserted into connector passages of the separator when the separator is positioned between member holders and implant members coupled to the member holders. Depth gauges 800 may be placed in the connector passages to push the connectors to proper depths within tapered slots in the implant members. The depth gauges may be pushed and/or impacted into the separator until depth gauge handles 804 contact the spreader and/or separator. After insertion, the spreader, separator, and depth gauges may be removed as a unit from the implant members by a slap hammer or other removal instrument.

Figure 33:
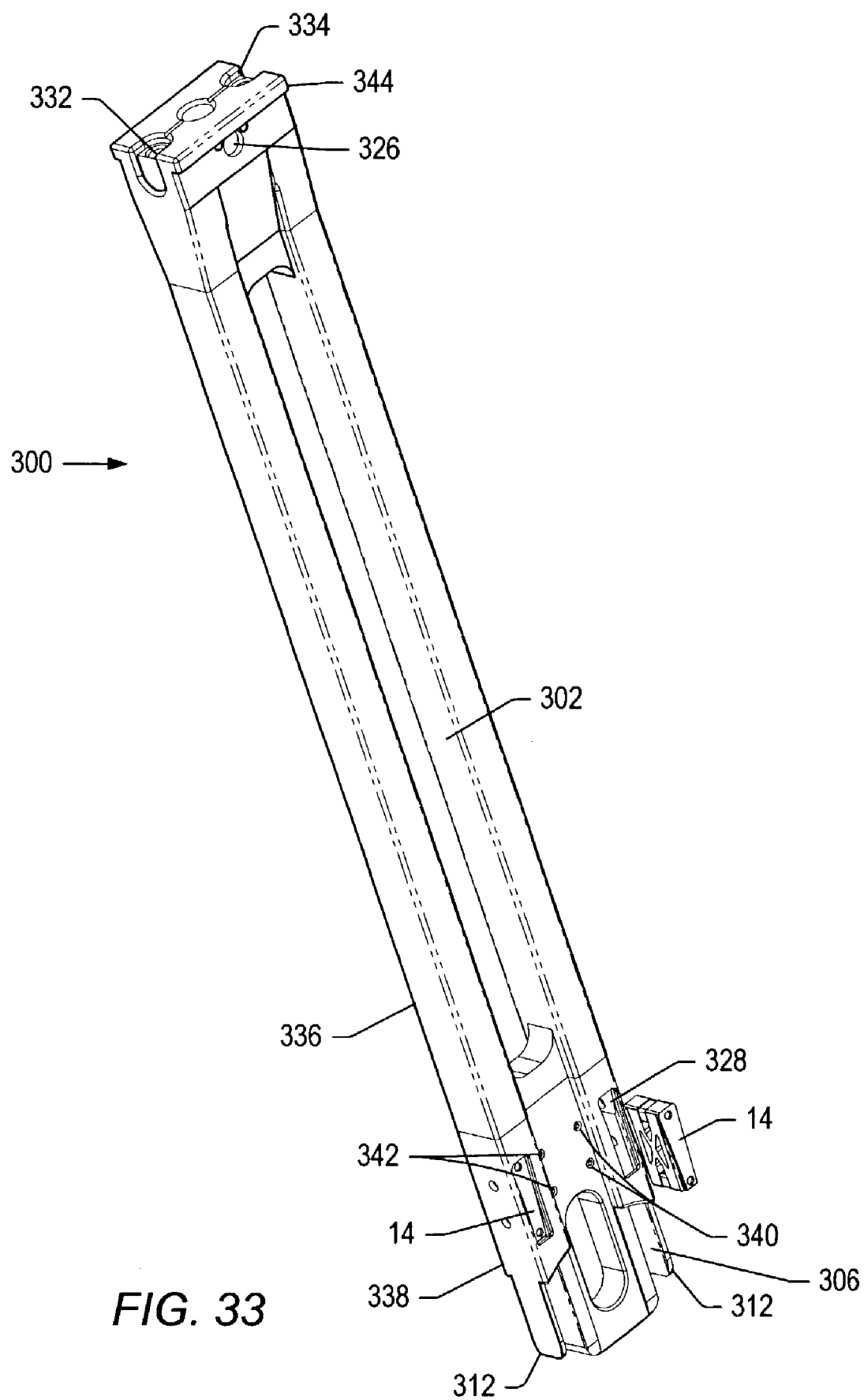
FIG. 33 shows a perspective view of an embodiment of a separator with a connector inserted into one side opening and a second connector positioned above a second side opening.

FIG. 33 depicts another embodiment of separator 300. Body 302 of the separator may have side openings 328 into passages 306 proximate distal ends of arms 312. Assembled connectors 14 may be inserted, or preloaded, into side openings 328 prior to inserting separator 300 into spreader 400 (e.g., the spreader depicted in FIG. 14). Side openings 328 may have shapes that only allow for insertion of connectors 14 when narrow ends of the connectors are facing a distal end of separator 300 and wide ends of the connectors are facing a proximal end of the separator. The shape of side openings 328 may prevent backward insertion of connectors 14 into separator 300. A pair of spring loaded detents positioned and sealed in detent openings 330 on sides of each side opening 328 may inhibit undesired release of connectors 14 from the side openings.

Separator 300 may include depth gauge passages 332 through the separator from a proximal end of the separator to side openings 328. Below side openings 328, separator 300 may have connector passages 306 sized to allow connectors to pass from the separator to implant members. Depth gauges may be inserted into depth gauge passages 332. When the depth gauges are inserted into passages 332, the depth gauges may push connectors 14 positioned in side openings 328 past detents in the side openings so that the connectors are pushed into connector passages 306. Connectors 14 may pass from connector passages 306 into tapered slots of implant members during formation of an implant.

Figure 34:
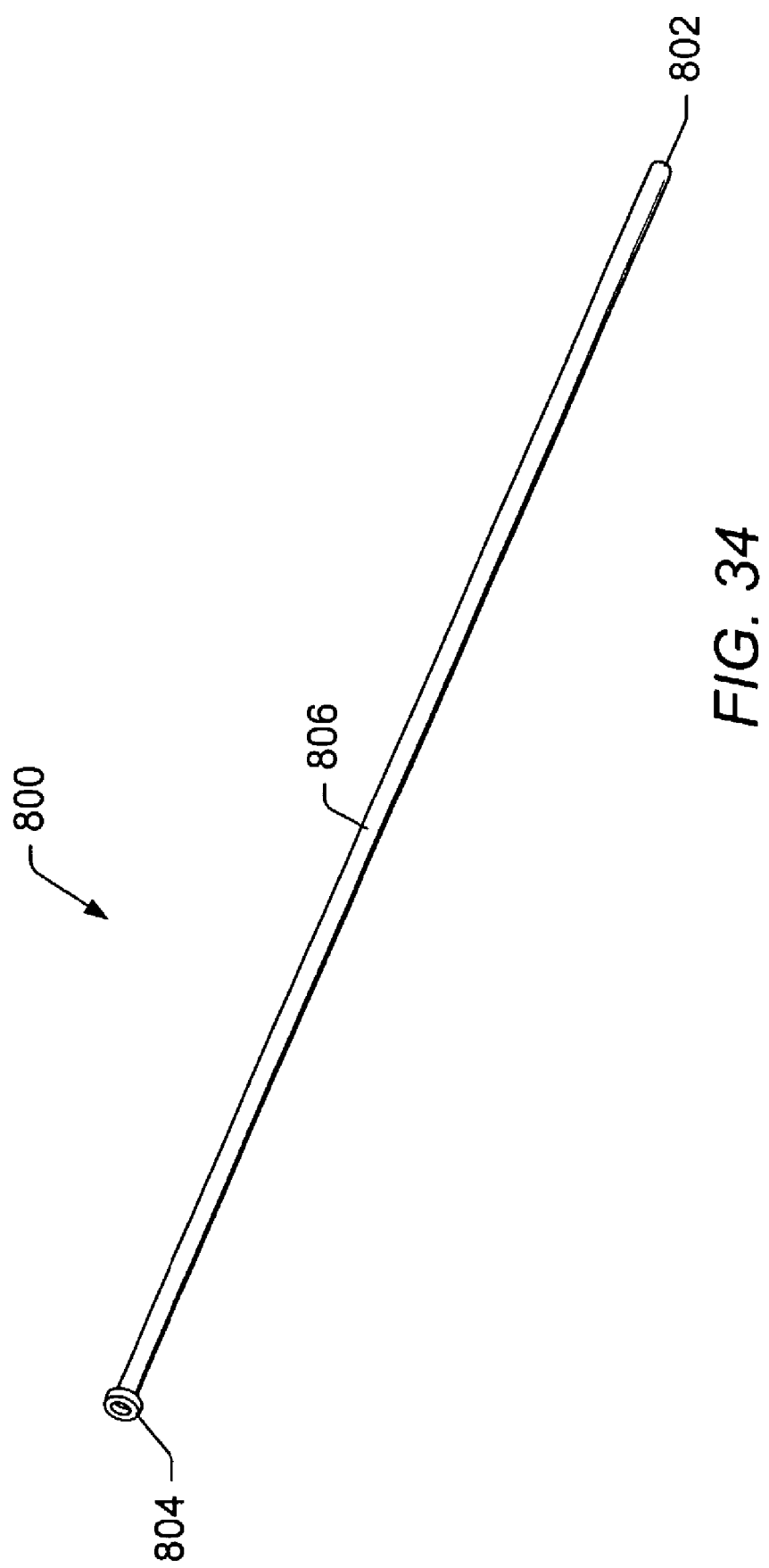
FIG. 34 depicts a perspective view of an embodiment of a depth gauge.

FIG. 34 depicts an embodiment of depth gauge 800 that may be used with the separator embodiment depicted in FIG. 33. Depth gauge 800 may include shaft 806. In an embodiment, shaft 806 may be a cylindrical shaft. In other embodiments, the shaft may have a different geometrical shape. Passages 332 in separator 300 may be sized and shaped to allow shaft 806 to pass through the passage so that end 802 contacts a connector positioned in side opening 328. In an embodiment, passage 332 may be a cylindrical passage. Forming a cylindrical passage may be easier and less expensive than forming a passage having a different geometric shape.

End 802 of depth gauge 800 may dislodge a connector from a side opening so that the connector passes into a connector passage of the separator. Depth gauge 800 may have sufficient length so that end 802 pushes the connector to a desired depth in implant members coupled to a spreader when the depth gauge is fully inserted into the separator. Depth gauge handle 804 may fit within a recess if fully inserted into the separator. Recess 334 for depth gauge handle 804 is shown in FIG. 33. If needed, a mallet or other impact surface may be used against a top surface of handle 804 to drive the depth gauge into the separator.

In a separator embodiment, such as separator 300 depicted in FIG. 33, first member 336 of the separator may be a separate piece from second member 338. Second member 338 may be releasably attached to first member 336. Detents 340 in first member 336 may interact with openings 342 in second member 338 to join the first member to the second member. Simultaneously depressing detents 340 may allow first member 336 to be separated from second member 338. Other fastening systems may be used to join a first member to a second member. A single first member 336 may be provided in an instrumentation set for a spinal fusion procedure. Various second members 338 for each size of connector provided in the instrumentation set may be provided in the instrumentation set. Having first member 336 separable from second member 338 may allow for reduction of weight of an instrumentation set and may increase available space within an enclosure that houses the contents of the instrumentation set.

Separator body 302 may include ridge 344. Ridge 344 may be a stop surface that limits insertion depth of separator 300 into a spreader.

Figure 35:
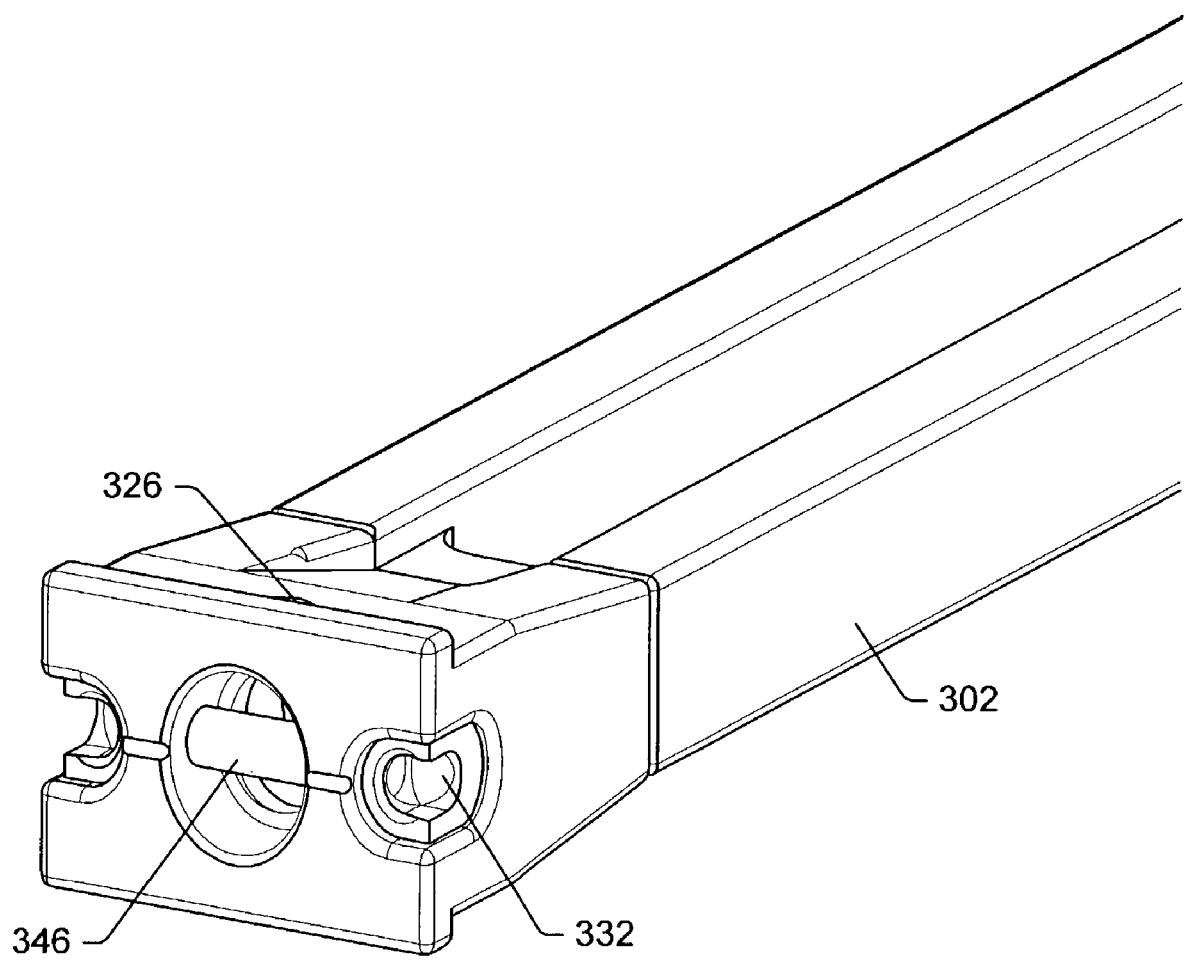
FIG. 35 depicts a perspective view of a portion of an embodiment of a separator that may be used with the slap hammer embodiment depicted in FIG. 29.

FIG. 35 depicts a portion of an embodiment of separator 300 that may be removed from a patient using the slap hammer embodiment depicted in FIG. 29. Separator 300 may include bar 346. Bar 346 may be press fit, threaded, welded, or otherwise attached to body 302 of separator 300. During removal of separator from a patient, bar 346 may fit within a slot of the slap hammer. When the slap hammer is rotated about 90°, bar 346 may fit within a holder of the slap hammer.

Figure 36:
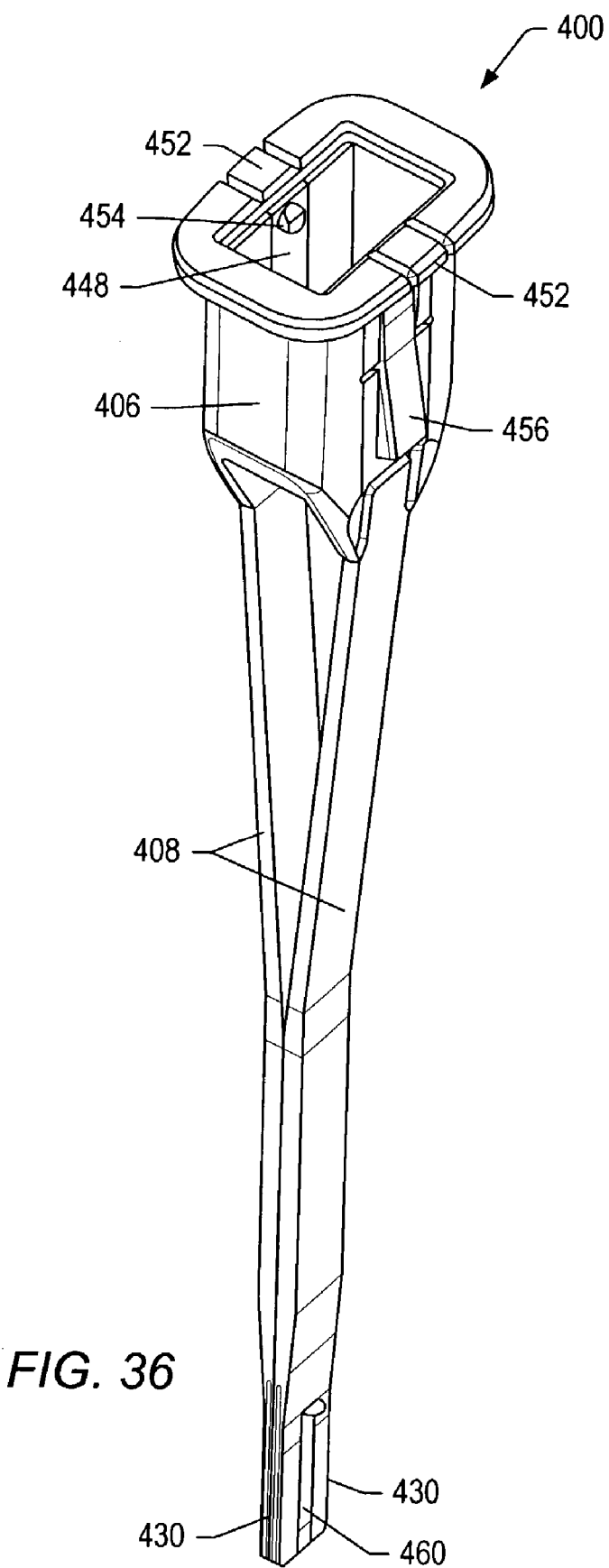
FIG. 36 shows a perspective view of an embodiment of a spreader.

FIG. 36 depicts an embodiment of spreader 400 in an initial position. Member holders 408 of spreader 400 may be sized so that widths of the member holders are smaller than widths of grooves in a separator (e.g., grooves 322 in separator 300 depicted in FIG. 30). The separator may slide down member holders 408 when the separator is inserted into spreader 400. Spreader body 406 may include opening 448 for the insertion of the separator. Member holders 408 may be positioned opposite each other on opposing sides of opening 448 to allow a separator to be positioned between member holders 408. When in the initial position, there may be substantially no separation distance between member mounts 430.

Body 406 may include shoulder 450 on sides of opening 448. Shoulder 450 may engage a separator ridge (e.g., ridge 344 of separator 300 depicted in FIG. 33). Body 406 may include retainers 452. In some embodiments, a spreader may only include one retainer. Retainer 452 may include engager 454. Each retainer 452 may be coupled to body 406 about a pivot axis by a spring. The spring may be a torsion spring. The spring may bias engager 454 towards opening 448. Engager 454 may be pushed outwards when a separator is inserted into spreader 400. The spring may force engager 454 towards the separator. Engager 454 may enter an opening in the separator (e.g., indention 326 in separator 300 depicted in FIG. 30) when the separator is fully inserted into spreader 400. When engager 454 is positioned in the opening of the separator, the separator and spreader 400 are linked together.

In an alternate embodiment, a retainer of a spreader may not include a spring member. An interference fit may be formed between a portion of the retainer and a portion of the spreader when the retainer is in a closed position such that the retainer holds an instrument within the spreader. The retainer may be rotatively coupled to the spreader about an axis. A rotational range of motion may be limited. In an embodiment, the rotational range of motion is limited to less than 45°. The retainer may be manually released and attached to a body of the spreader by contacting the retainer and rotating the retainer away or towards the spreader. The retainer may include a textured contact surface to facilitate rotating the retainer.

Retainer engagers 454 may include chamfered surfaces that promote rotation of retainers 452 away from a body of a separator when an instrument, such as a separator, is inserted into opening 448. The chamfered surfaces allow initial deflection of retainers 452 when the separator is inserted into spreader 400 so that a user does not have to manually pull the retainers outwards.

Retainer 452 may include contact surface 456. Pushing contact surface 456 may rotate retainer 452 about a pivot axis and allow engager 454 to be removed from an opening in a separator that is fully inserted into spreader 400. The separator may be removed from spreader 400 when contact surfaces 456 of retainers 452 are depressed and the separator is pulled away from the spreader.

Figure 37:
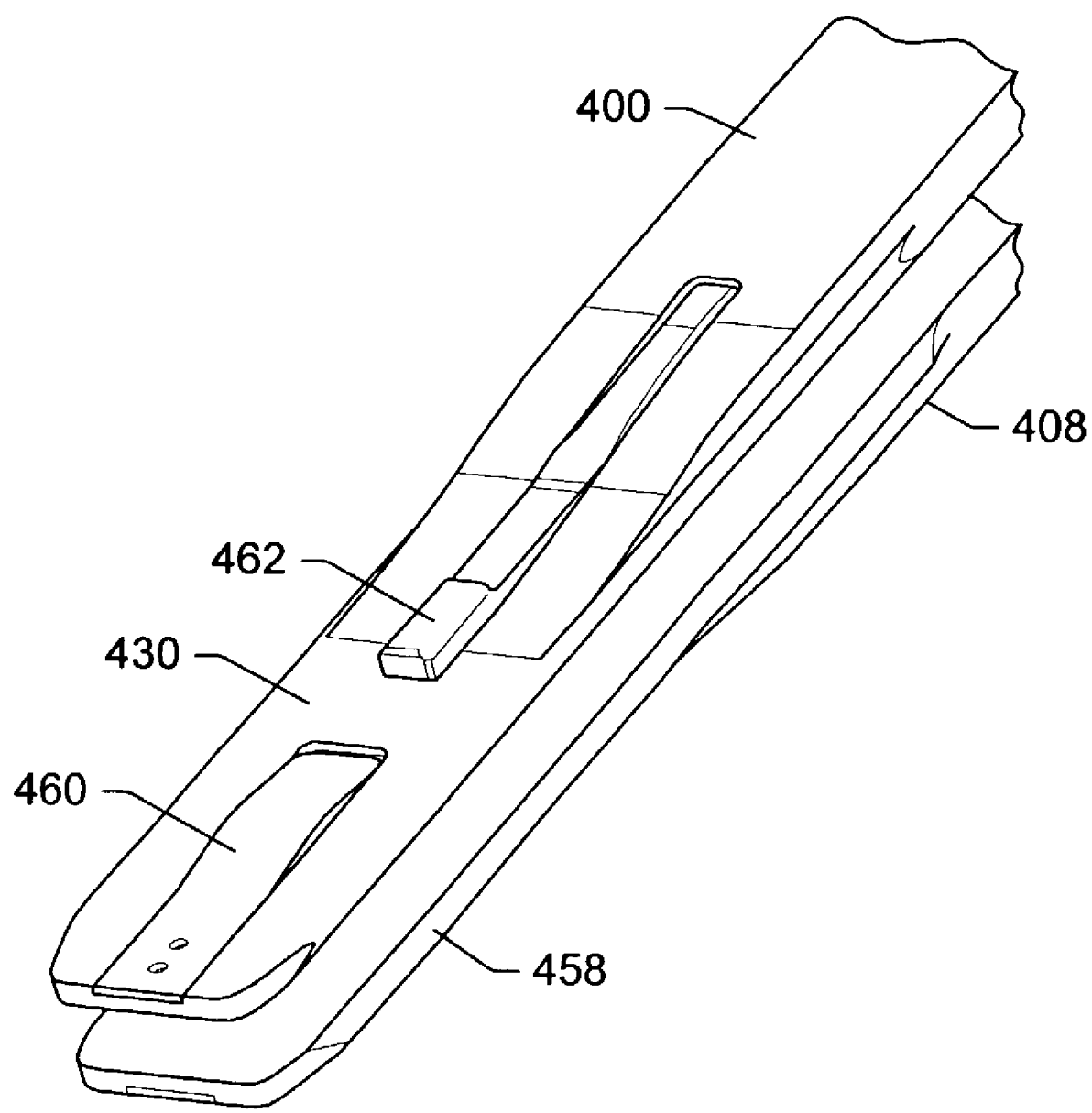
FIG. 37 shows a perspective view of a portion of an embodiment of a spreader emphasizing an outer surface of a member holder.

FIG. 37 depicts an embodiment of member mounts 430 of member holders 408. Member holders 408 may include sloped surfaces 458, spring members 460, and stops 462. Sloped surfaces 458 may form a dovetail connection with sloped surfaces of implant members (e.g., sloped surfaces 70 of implant member 12 depicted in FIG. 2). When an implant member is coupled to member holder 408, spring member 460 may provide a force against the implant member that holds the implant member to the member holder. Stop 462 may limit insertion of the implant onto member holder 408. In some spreader embodiments, spring member 460 and stop 462 may be integral members.

A distance between sloped surfaces of implant members, such as sloped surfaces 70 of implant members 12 depicted in FIG. 2, may vary depending on the size of the implant members. A spreader that has member holders that mate with sloped surfaces of implant members may be provided for each size of implant member included in the instrumentation set. For example, if the instrumentation set includes medium and large implant members, the instrumentation set will include a first spreader with member holders sized to accept the medium sized implant members and a second spreader with member holders sized to accept the large sized implant members.

To prepare a spreader for a fusion procedure, implant members may be inserted onto member holders of the spreader. A visual check may be performed to check that the implant members are fully inserted onto the member holders so that end surfaces of the implant members contact stops of the spreader. The implant members may be inserted into a disc space between vertebrae or into an opening between bone segments. In some embodiments, a disc space or an opening between bone segments is large enough to accept the implant members. In some embodiments, a disc space or an opening between bone segments may be too small to allow for insertion of implant members. If the disc space or opening is too small, an end cap may be placed on the spreader, and impact forces may be applied to the spreader to insert the implant members into the disc space or into the opening between bone segments. Insertion guides may be used to inhibit protrusions of the implant members from scarring surfaces of vertebrae or bone segments.

Figure 38:
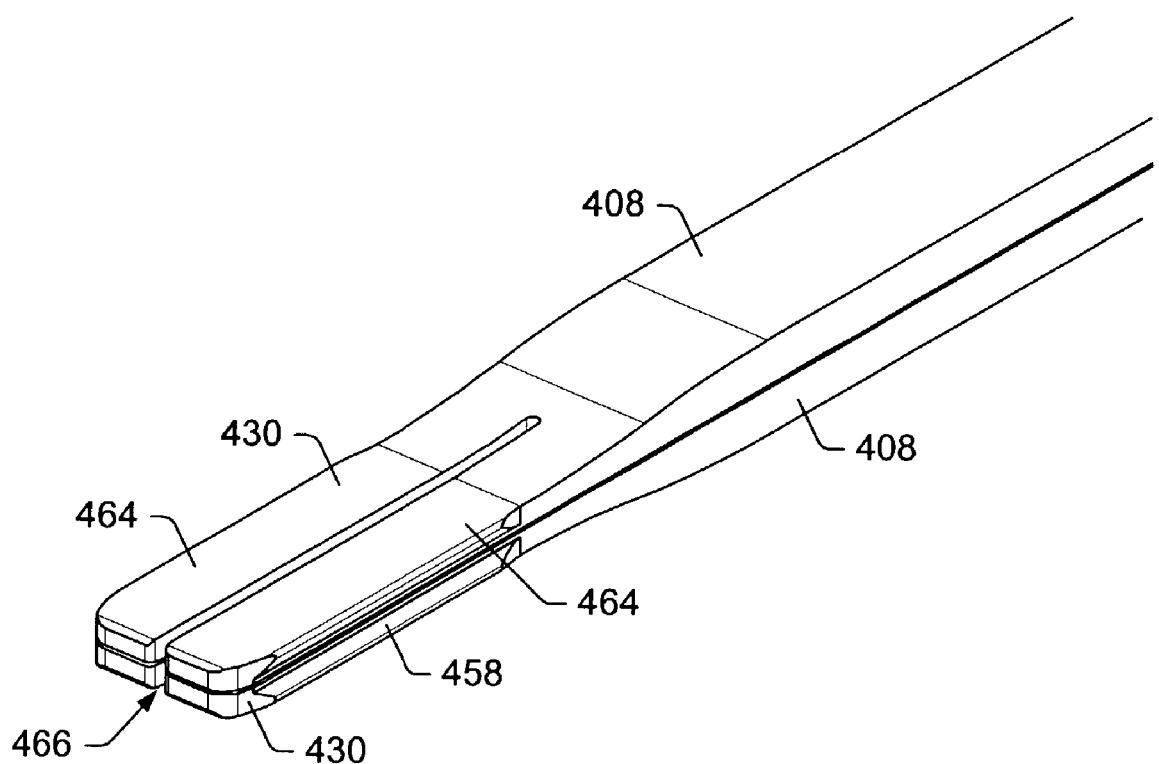
FIG. 38 shows a perspective view of a portion of an embodiment of a spreader that emphasizes a member holder.

FIG. 38 depicts an embodiment of member mounts 430 of member holders 408. Member holders may include sloped surfaces 458, arms 464, and slot 466. Sloped surfaces 458 may form a dovetail connection with sloped surfaces of implant members (e.g., sloped surfaces 70 of implant member 12 depicted in FIG. 2). Arms 464 may include a slight taper. The taper may limit an insertion depth of an implant member onto member mount 430. When an implant member is coupled to member holder 408, the taper of arms 464 may cause compression of slot 466. Compression of slot 466 may cause arms 464 to apply a force to the implant member that holds the implant member onto the member mounts 430.

Figure 39:
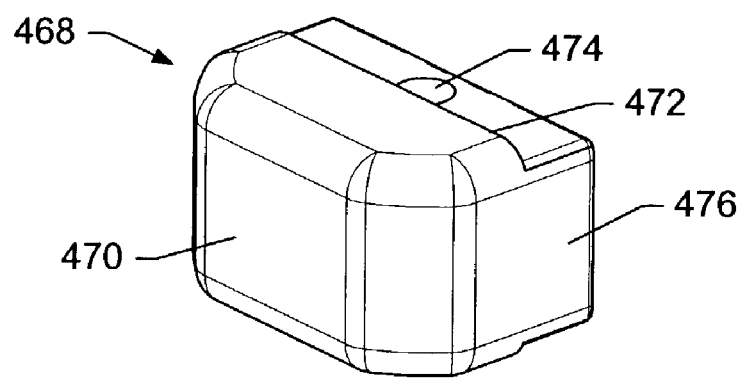
FIG. 39 shows a perspective view of an embodiment of an end cap for a spreader.

FIG. 39 depicts an embodiment of end cap 468 for a spreader. End cap 468 may be placed in an opening in a body of a spreader (e.g., opening 448 of spreader 400 depicted in FIG. 36). Impact end cap 468 may include upper surface 470, ridge 472, openings 474, and lower body 476. Lower body 476 of impact end cap 468 may be shaped and sized to fit within opening 448 of spreader 400 depicted in FIG. 36. Engagers 454 may extend into openings 474 when end cap 468 is inserted into the spreader. Ridges 472 of impact end cap 468 may contact shoulders 450 of spreader body to provide a large contact surface between end cap 468 and spreader 400.

Figure 40:
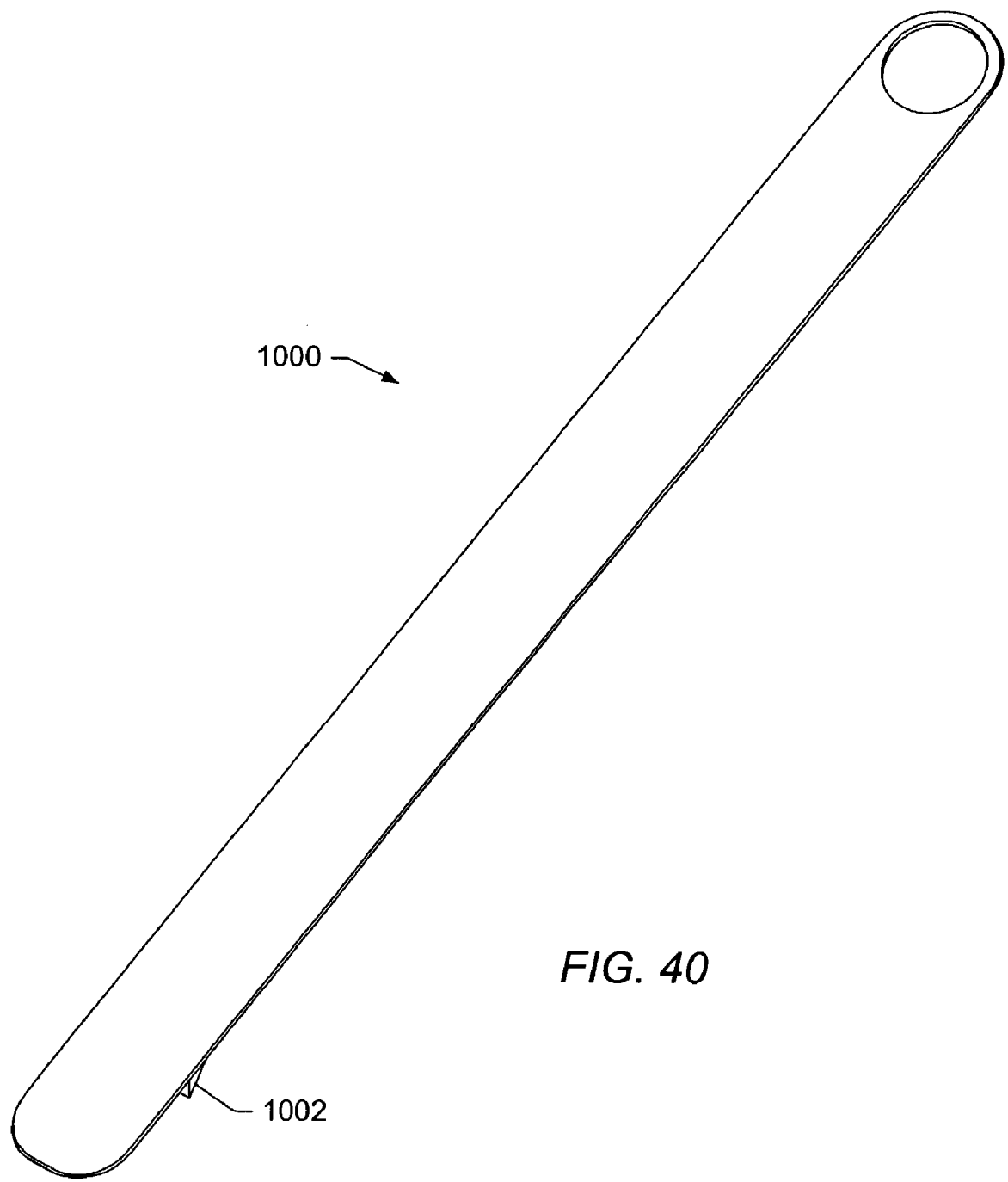
FIG. 40 shows a perspective view of an embodiment of an insertion guide.

If implant members attached to ends of member holders are too thick to allow for insertion into a prepared disc space, an insertion guide and an impaction instrument may be used to insert the implant members into the disc space. FIG. 40 depicts an embodiment of insertion guide 1000. Insertion guide 1000 may be inserted into a disc space or a space between bone segments until stop 1002 contacts bone. Stop 1002 may extend across a back surface of insertion guide 1000. In some embodiments, insertion guides may not include stops. Insertion guides 1000 may be made of thin metal strips. The metal may have a hardness equal to or greater than a hardness of protrusions extending from implant members so that the protrusions will not significantly score the insertion guides. In other embodiments, insertion guides may be made of polymer, or include a polymer coating, that is able to resist scoring from protrusions of implant members. In some embodiments, a single insertion guide may include two strips. The insertion guide may be positioned between vertebrae or bone structures. Implant members attached to a spreader may be inserted between the two strips of the insertion guide.

Figure 41:
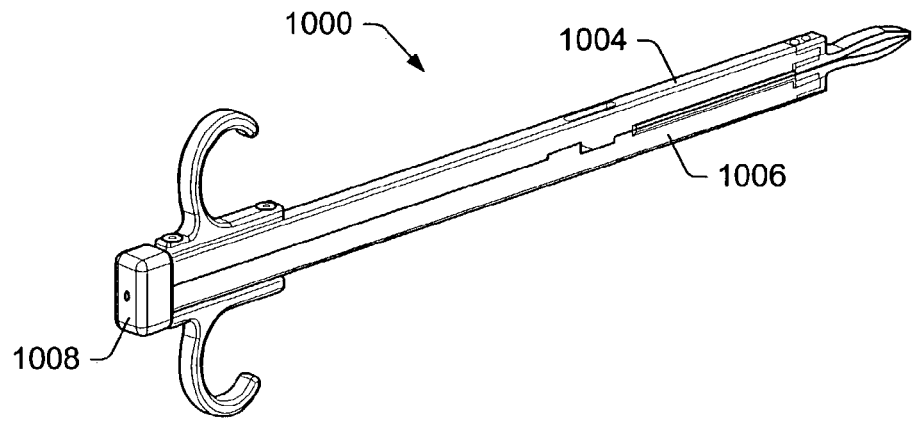
FIG. 41 shows a perspective view of an embodiment of an insertion guide.
Figure 42:
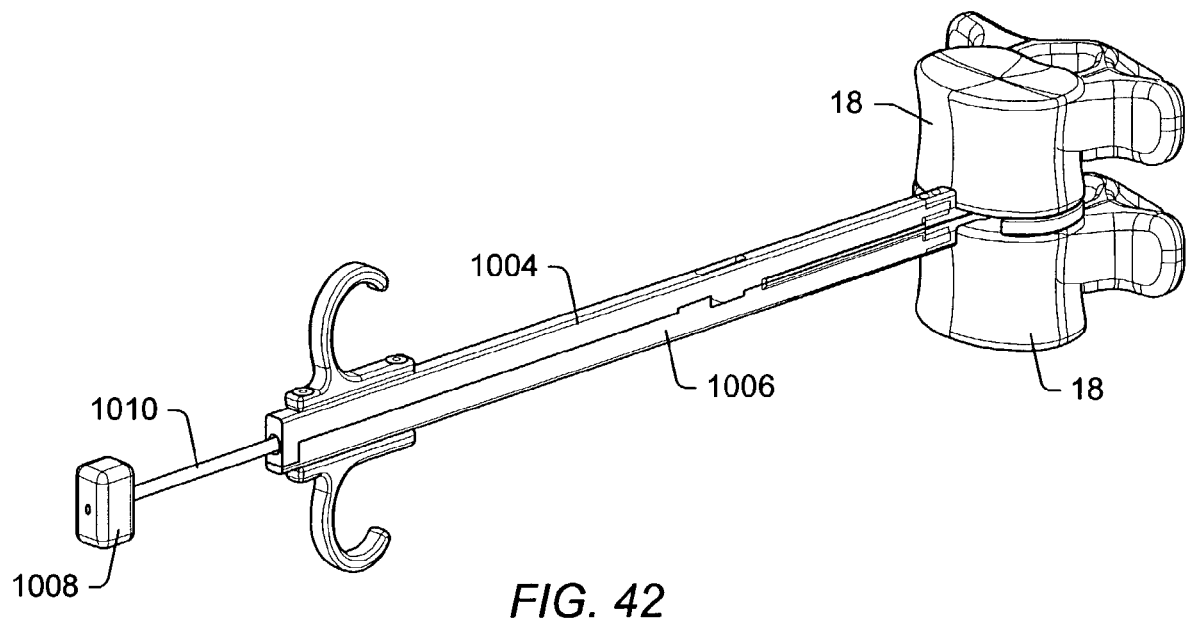
FIG. 42 shows a perspective view of an embodiment of an insertion guide inserted between vertebrae.

FIGS. 41-44 depict embodiments of insertion guide 1000. FIG. 41 depicts an embodiment of joined together insertion guide 1000. Insertion guide 1000 may include first arm 1004, second arm 1006, and cap 1008. End portions of first arm 1004 and second arm 1006 may be inserted in a disc space formed between vertebrae. Portions of first arm 1004 and second arm 1006 may extend into cap 1008. Cap 1008 may be separated from first arm 1004 and second arm 1006 to allow for separation of the first arm and the second arm. As shown in FIG. 42, cap 1008 may include shaft 1010. Cap 1008 and shaft 1010 may help keep first arm 1004 and second arm 1006 joined together before and during insertion of end portions of insertion guide 1000 into the disc space. After end portions are inserted into the disc space, cap 1008 and shaft 1010 may be removed from first arm 1004 and second arm 1006 to allow for separation of the first arm and the second arm.

Figure 43:
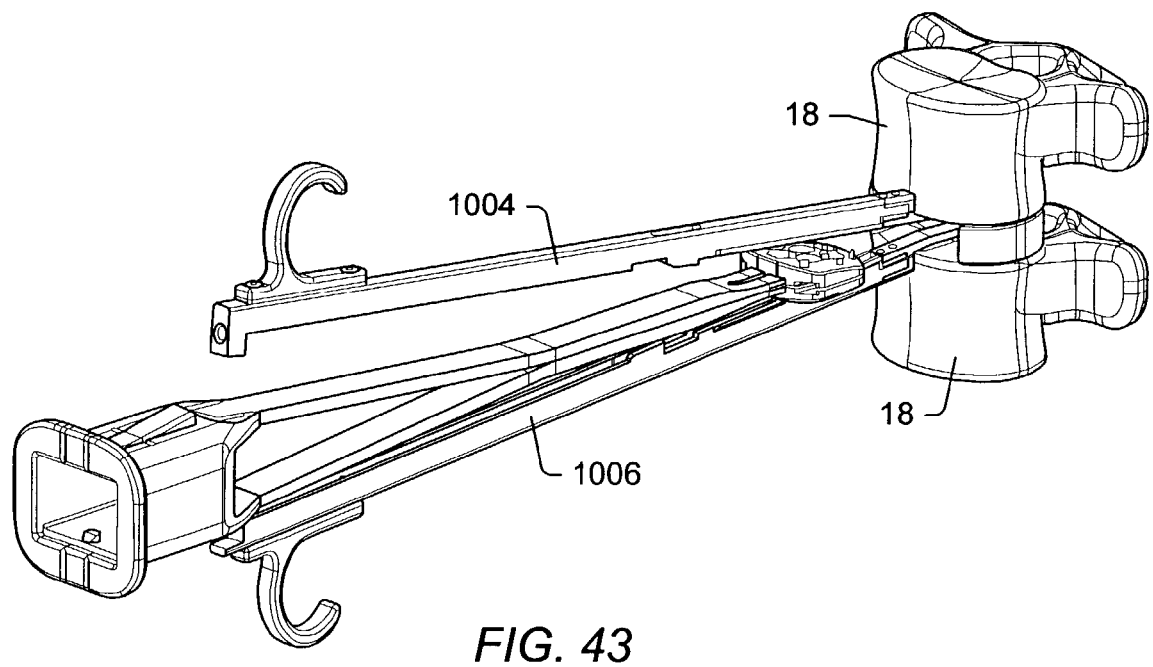
FIG. 43 shows a perspective view of an embodiment of a spreader with attached implant members positioned between arms of an insertion guide.
Figure 44:
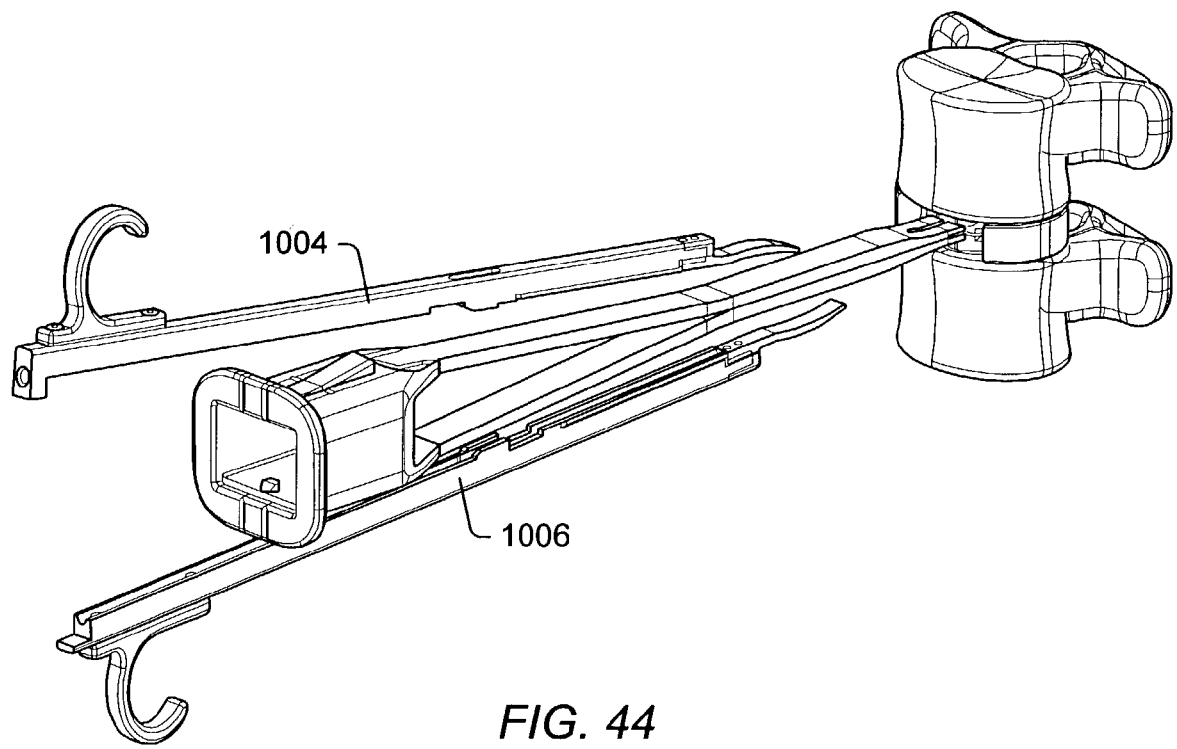
FIG. 44 shows a perspective view of an embodiment of a spreader with attached implant members after removal of arms of an insertion guide.

After placement of insertion guide 1000 and removal of cap 1008 and shaft 1010, a spreader with attached implant members may be inserted between first arm 1004 and second arm 1006. The implant members may be inserted into a disc space. FIG. 43 depicts a spreader with attached implant members positioned between first arm 1004 and second arm 1006. After insertion of implant members into the disc space, first arm 1004 and second arm 1006 may be removed. FIG. 44 depicts the spreader and implant members after removal of first arm 1004 and second arm 1006.

Figure 45:
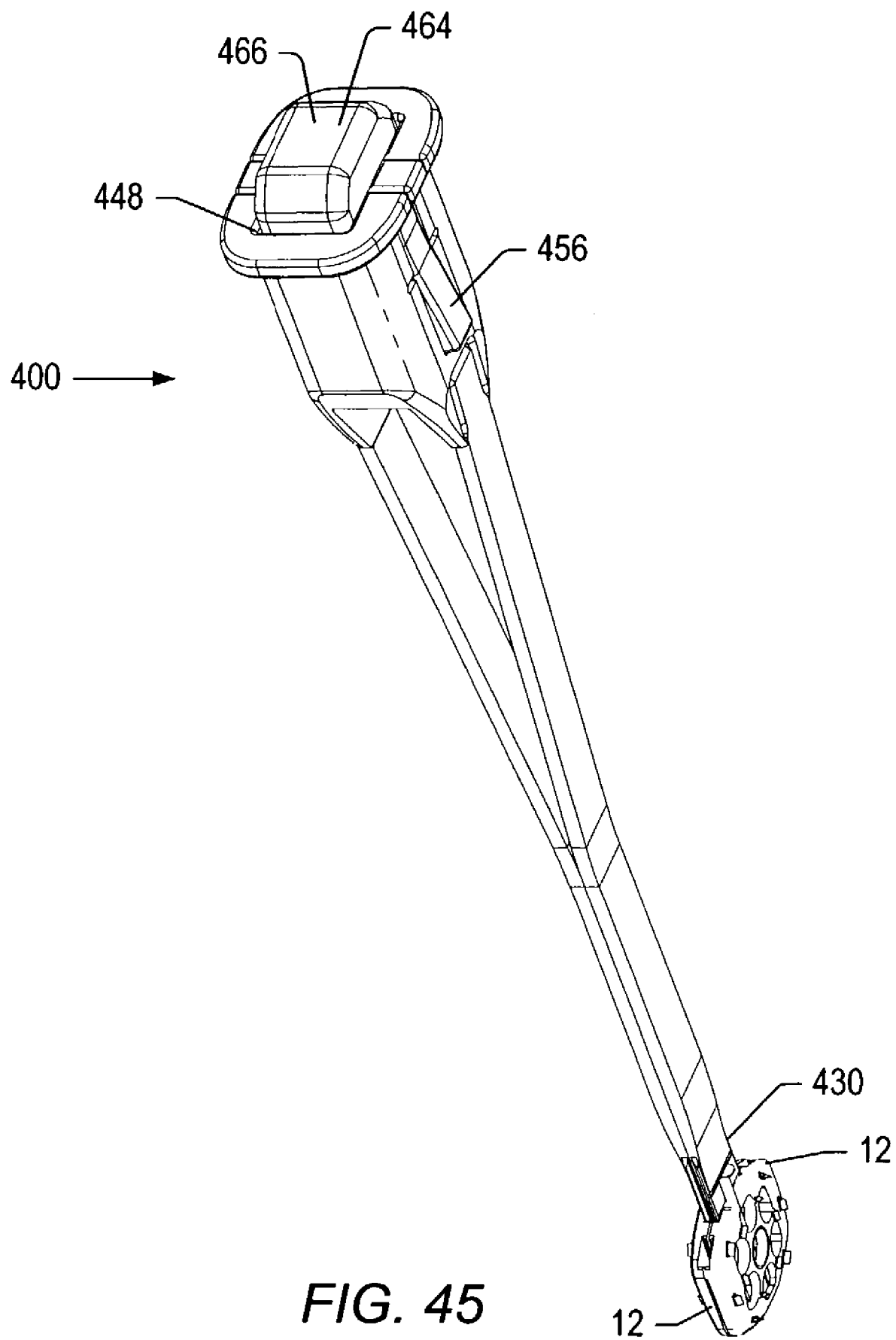
FIG. 45 shows a perspective view of an embodiment of a spreader with an end cap inserted into an opening of the spreader.

FIG. 45 depicts a spreader and end cap combination. After placement of the insertion guides on each side of a disc space or an opening between bone segments, implant members 12 coupled to spreader 400 may be positioned between the insertion guides. A mallet or other impact instrument may strike upper surface 470 of end cap 468 to drive spreader 400 into the disc space or between the bone segments. After implant members 12 are inserted to a desired depth, insertion guides may be removed, and impact end cap 468 may be released and removed from spreader 400.

After insertion of implant members that are connected to a spreader into a disc space or opening between bone segments, a separator may be inserted into the spreader. A separator, such as separator 300 depicted in FIG. 33, may be placed in an opening of a spreader, such as opening 448 in spreader 400 depicted in FIG. 36. An impact instrument may be used to force the separator between member holders 408 of spreader 400. Sloped surfaces of member holders 408 and chamfered end surfaces of the separator may allow a large portion of the force applied to the separator to separate implant members coupled to the spreader. The implant members may establish a desired separation distance between vertebrae or bone segments without over-distracting the vertebrae or bone segments. Protrusions of the implant members extend into adjacent bone to anchor the implant members to bone. When the separator is fully inserted into the spreader, engagers of the spreader may enter into openings of the separator to join the separator and the spreader together.

After insertion of the separator into the spreader, depth gauges may be inserted into the depth gauge passages of the separator. If needed, an impact instrument may be used to tap handles of the depth gauges to force the depth gauges into depth gauge recesses in the separator. Pushing the depth gauges into the separator may release connectors positioned in the spreader into connector passages. Placing depth gauge handles in the separator recesses positions the connectors in tapered slots in implant members connected to the spreader.

Figure 46:
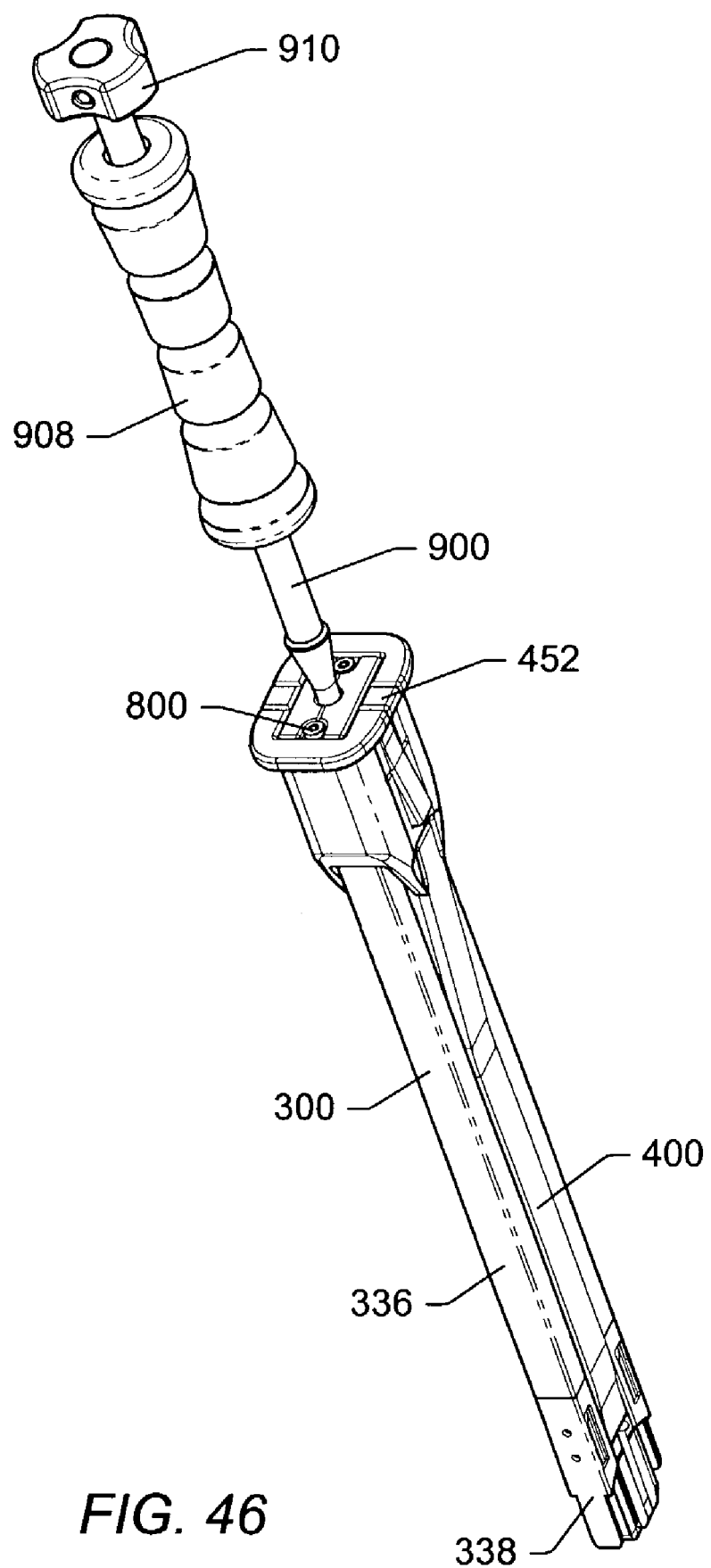
FIG. 46 shows a perspective view of an embodiment of a combination slap hammer, separator, spreader, and depth gauges.

After insertion of the depth gauges, a slap hammer may be attached to the separator. FIG. 46 depicts an embodiment of slap hammer 900 coupled to separator 300. In some embodiments, the slap hammer may include detents that connect to an engagement surface of the separator. In other embodiments, an attachment mount of the separator may be threaded, and an end of the slap hammer would include mating threading that allows the slap hammer to be joined to the separator.

After joining slap hammer 900 to separator 300, slide 908 may be impacted against upper stop 910. The impaction removes separator 300, spreader 400, and depth gauges 800 from implant members 12 that are secured to bone by protrusions of the implant members. Removing separator 300, spreader 400, and depth gauges 800 leaves implant members 12 and connectors in the disc space or in the space between bone segments. Separator 300, spreader 400, and depth gauges 800 may be separated from each other when convenient.

Implant members that are joined together by connectors may be left in a disc space between vertebrae or within an opening between bone segments after removal of separator 300, spreader 400, and depth gauges 800. A connector seater may subsequently be used to affix the connectors to the implant members.

A seater may be used to permanently affix connectors to implant members after an implant has been formed in a patient. Seater 1100 may apply force to the connectors and implant members to drive the connectors into tapered slots of implant members. Forces applied to the connectors and implant members may be sufficiently large to deform the slots and/or connectors so that the connectors cannot be removed from the implant members.

Figure 47:
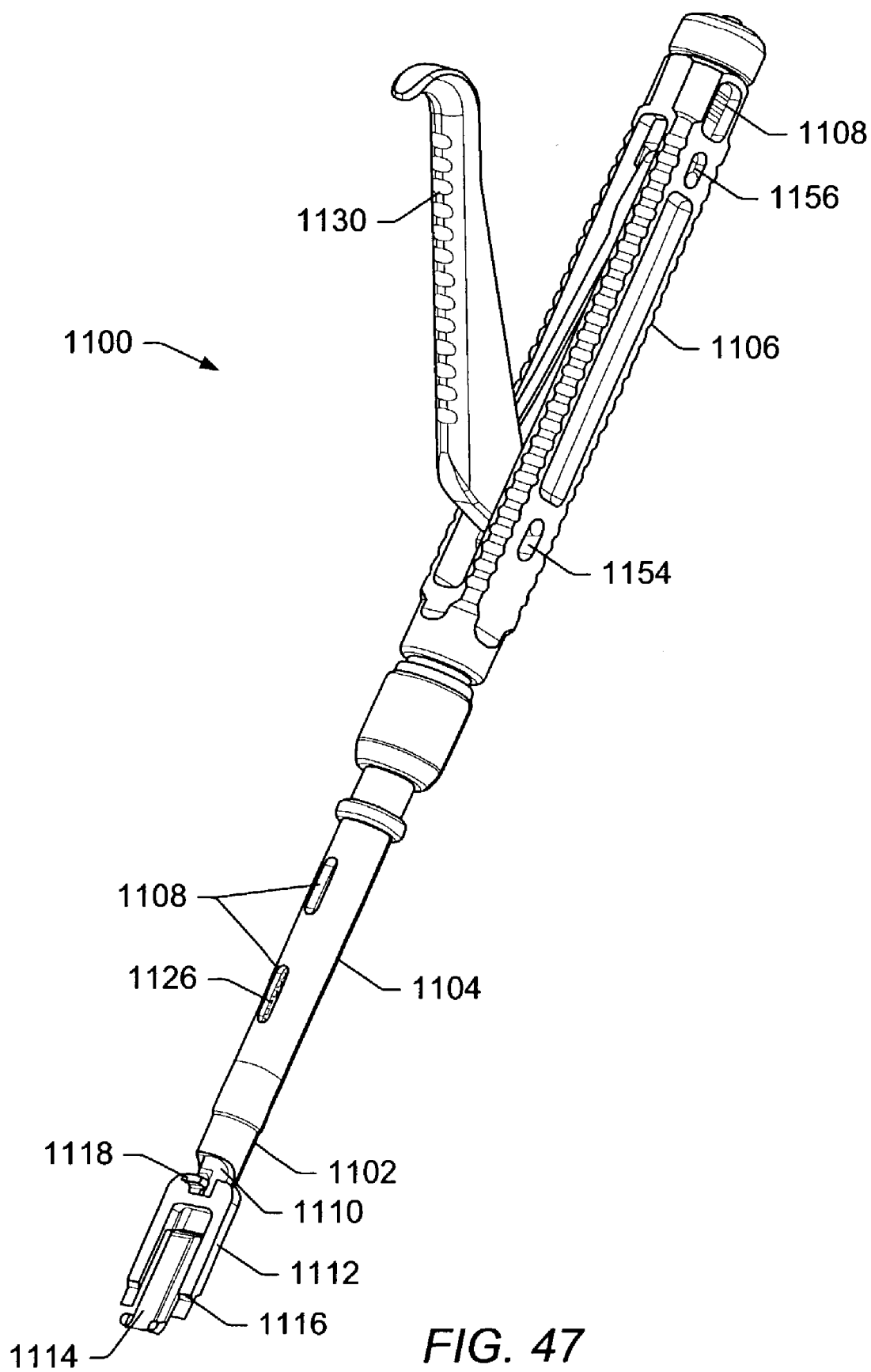
FIG. 47 shows a perspective view of an embodiment of a connector seater.

FIG. 47 depicts an embodiment of seater 1100. Seater 1100 may include attachment portion 1102, extender 1104, and activation mechanism 1106. Threaded connections, quick disconnect connections, or other types of connections may couple attachment portion 1102 to extender 1104, and the extender to activation mechanism 1106. In some embodiments, attachment portion 1102, extender 1104, and/or activation mechanism 1106 may be permanently coupled together by welds or sealant. In other embodiments, attachment portion 1102, extender 1104, and/or activation mechanism 1106 may be formed as a single inseparable unit. Seater 1100 may include openings 1108. Openings 1108 may allow steam and/or other disinfectants to enter into seater 1100 during a sterilization procedure.

Figure 48:
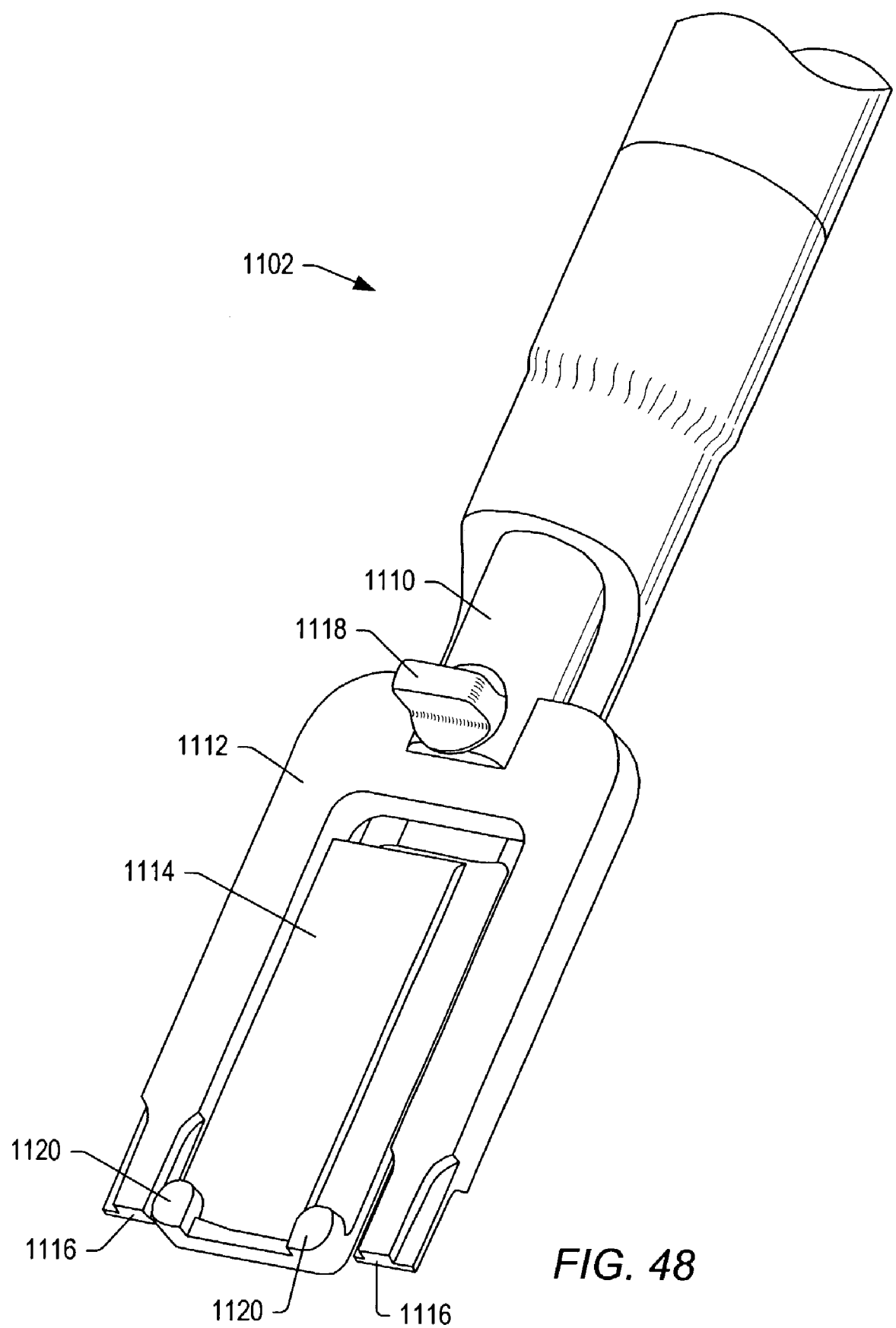
FIG. 48 shows a perspective view of a portion of an embodiment of a connector seater.

Attachment portion 1102 of a seater may include drive rod 1110, connector engager 1112, and member engager 1114, as shown in FIGS. 47 and 48. A spring in attachment portion 1102 may hold drive rod 1110 in an initial position. Engaging an activation mechanism of seater 1100 may extend drive rod 1110 to a second position. The spring may return drive rod 1110 to the initial position when activation mechanism 1106 is disengaged. Drive rod 1110 may be coupled to connector engager 1112. When member engager 1114 is coupled to an implant member, engaging activation mechanism 1106 of seater 1100 may extend drive rod 1110 and connector engager 1112 coupled to the drive rod relative to stationary member engager 1114. Ends 1116 of connector engager 1112 may be forced against connectors to drive the connectors into the tapered slots in the implant members.

Connector engager 1112 of seater 1100 may have ends 1116 that press against the connectors positioned within implant members. Connector engager 1112 may be sized to contact the connectors that are spaced a set distance apart in a specific size of implant member. Connector engager 1112 for each implant member size may be included in an instrumentation set that is provided to a surgical team that will perform an implant insertion procedure. For example, an instrumentation set may include a small, medium, and/or large connector engager 1112. Connector engager 1112 may be positioned within a slot in an end of drive rod 1110 of the seater. Fastener 1118 may attach connector engager 1112 to drive rod 1110. In an embodiment, fastener 1118 is a screw. In other embodiments, other types of fasteners 1118 may be used, or connector engager 1112 may be permanently attached to drive rod 1110 of attachment portion 1102 of a seater.

As shown in FIG. 48, member engager 1114 may include extensions 1120. Extensions 1120 may be placed within openings 28 in implant member 12 (depicted in FIG. 1). Extensions 1120 may be positioned against recessed surfaces 30 of implant member 12 to couple seater 1100 to the implant member.

Figure 49:
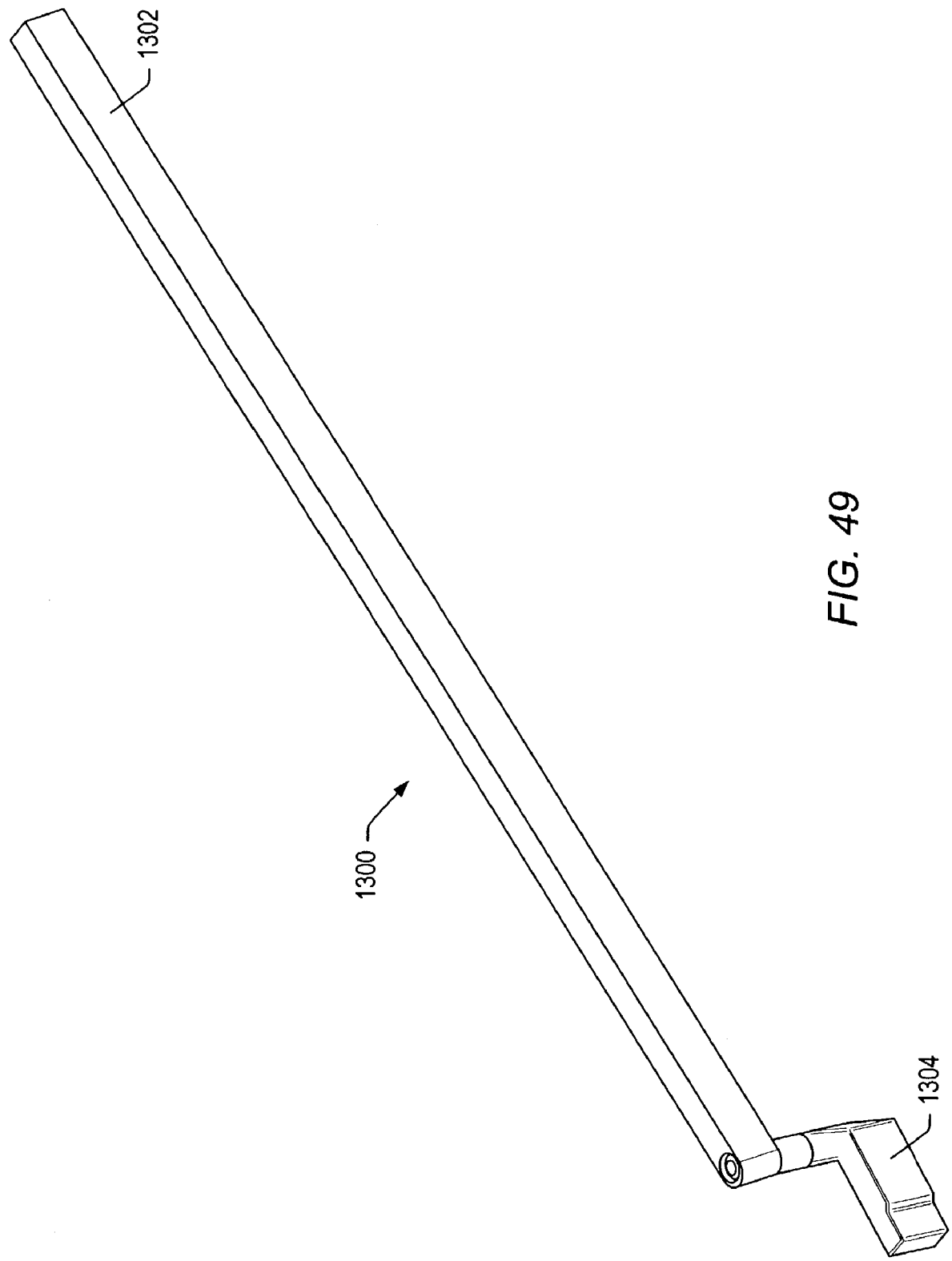
FIG. 49 shows a perspective view of an embodiment of a retainer.

A retainer may be used to inhibit unintentional removal of seater 1100 (shown in FIG. 47) from implant member 12 (shown in FIG. 1). FIG. 49 depicts an embodiment of retainer 1300. Retainer 1300 may include handle 1302 and spacer 1304. Handle 1302 may allow for easy positioning of spacer 1304. Spacer 1304 may be placed between a first implant member that is not coupled to a seater and a seater that is coupled to a second implant member. Spacer 1304 may inhibit disengagement of extensions 1120 of attachment portion 1102 of seater 1100 (shown in FIG. 48) from the second implant member during use of the seater.

Figure 50:
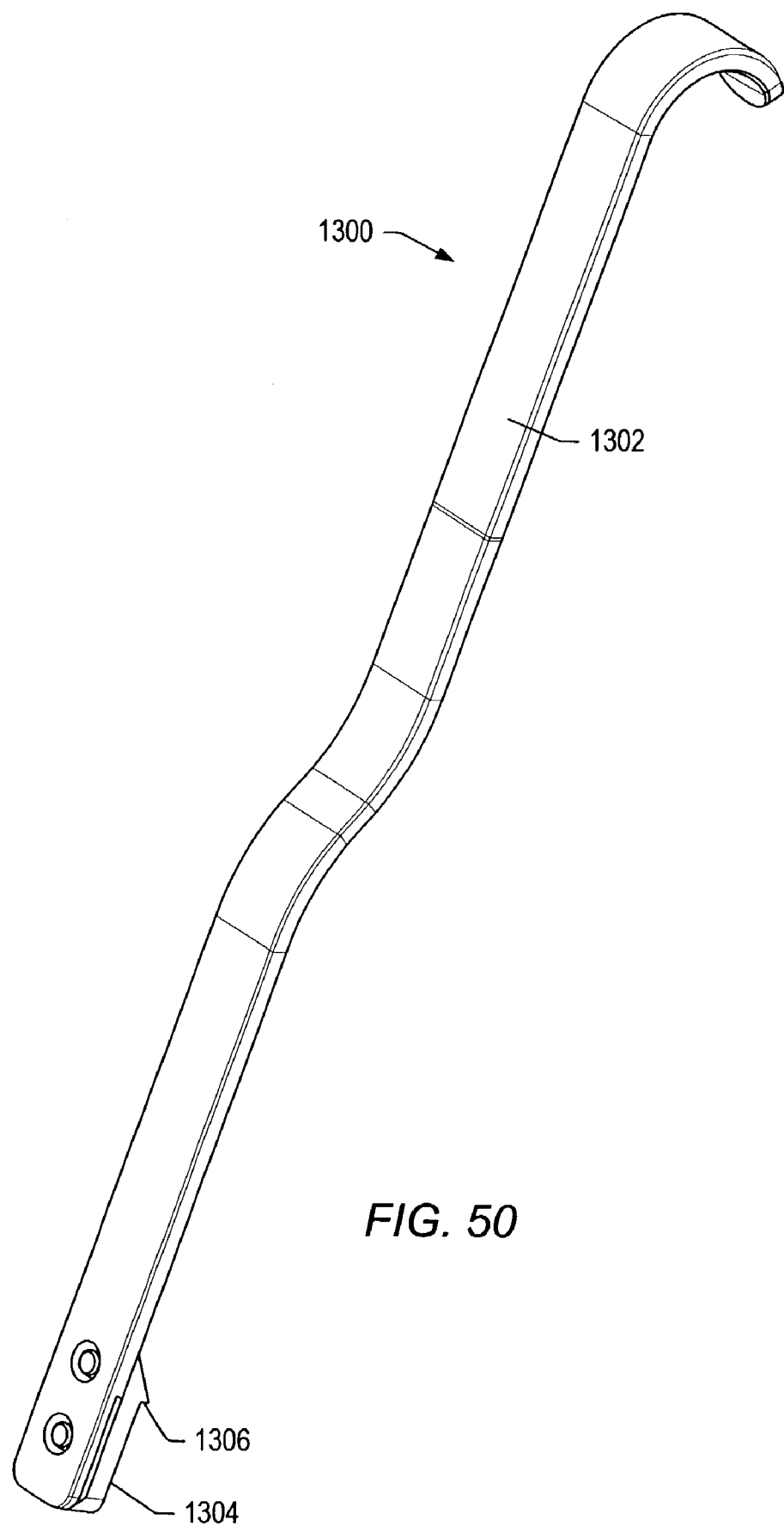
FIG. 50 shows a perspective view of an embodiment of a retainer.

Another embodiment of retainer 1300 with handle 1302 is shown in FIG. 50. Spacer 1304 may be placed between a seater coupled to an implant member and an implant member that is not coupled to the seater. Spacer 1304 may include stop surface 1306. Stop surface 1306 may limit an insertion depth of retainer 1300 between implant members. Spacer 1304 may inhibit disengagement of the attachment portion of the seater from an implant member during use of the seater.

Figure 51:
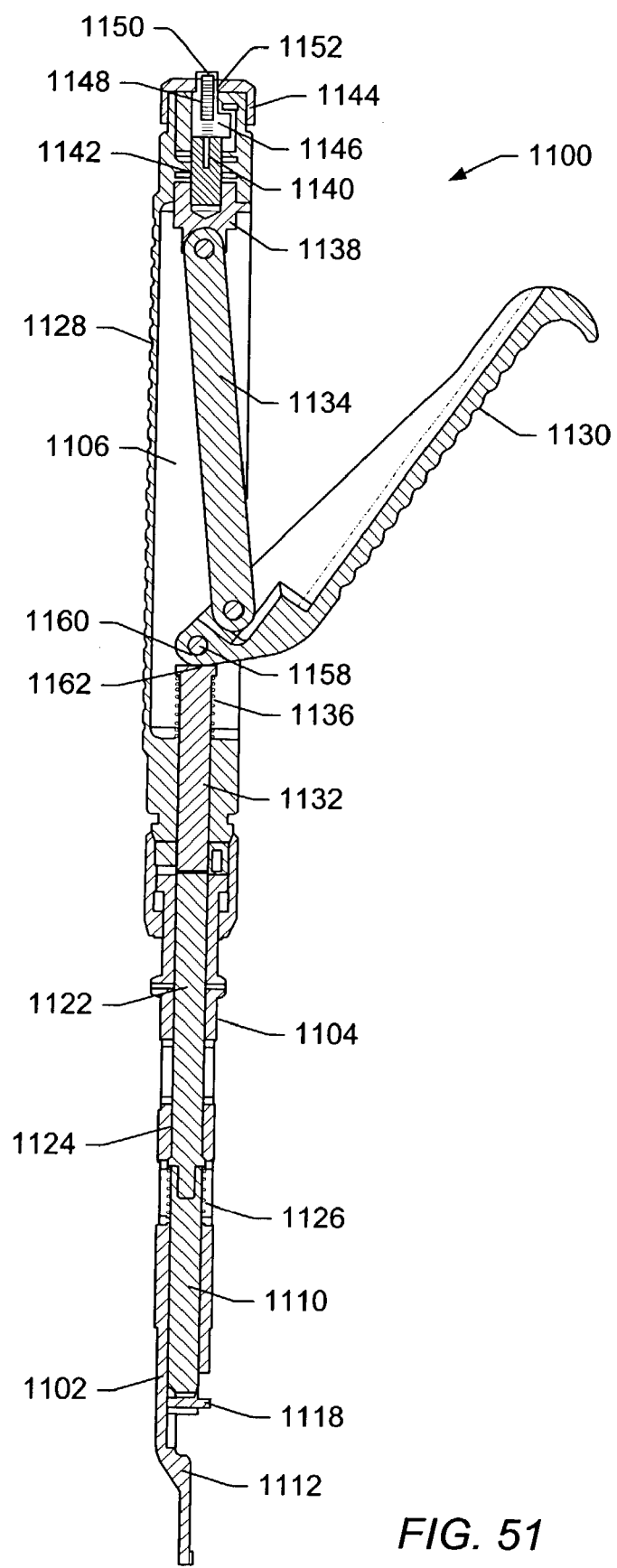
FIG. 51 shows a cross-sectional representation of an embodiment of a seater.

FIG. 51 depicts a cross-sectional representation of a seater embodiment. Extender 1104 of seater 1100 may include internal drive rod 1122 and outer body 1124. Spring 1126 within extender 1104 may force drive rod 1122 to an initial position. Engaging activation mechanism 1106 of seater 1100 may force drive rod 1122 towards attachment portion 1102 coupled to extender 1104. Extender 1104 may provide a length to seater 1100 that allows a surgeon to easily attach the seater to an implant member within a patient. The length of seater 1100 may allow the surgeon to activate the seater to couple connectors to the implant member from above an opening in the patient.

Figure 52:
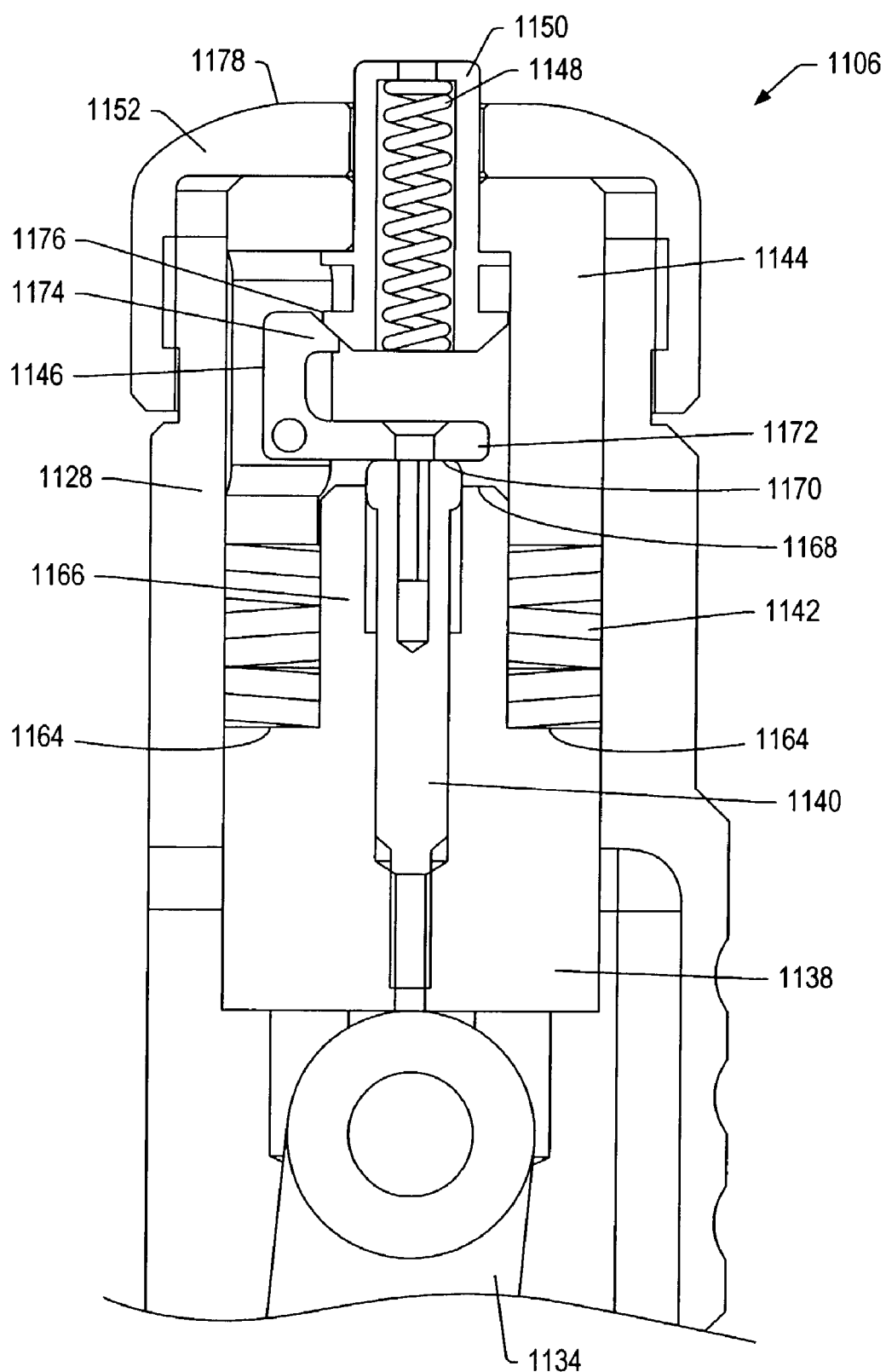
FIG. 52 shows a cross-sectional representation of an activation portion of an embodiment of a seater.
Figure 53:
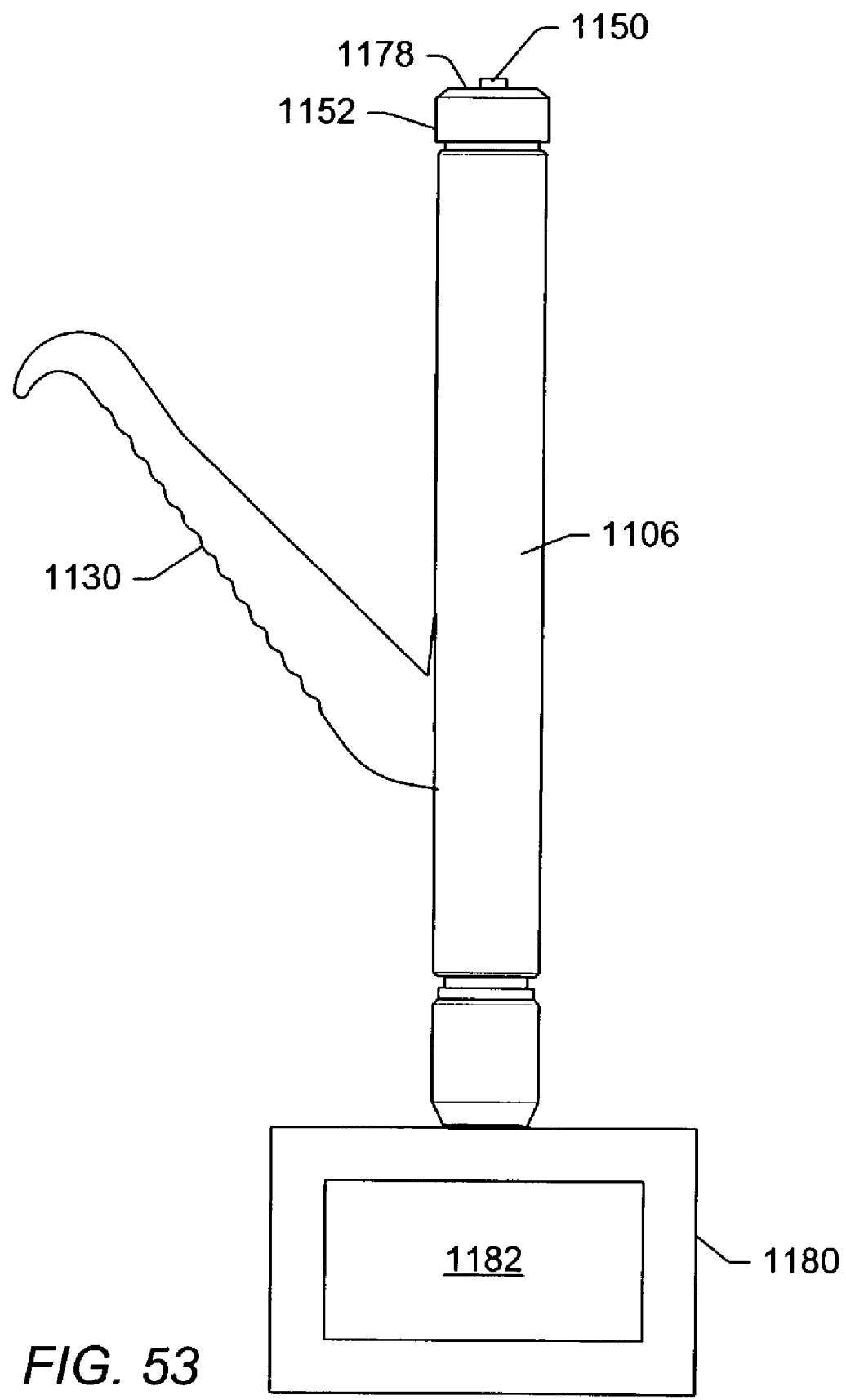
FIG. 53 shows a perspective view of an embodiment of a connector attached to a calibrator.

FIGS. 51 and 52 show cross-sectional views of an embodiment of activation mechanism 1106 of a seater. Activation mechanism 1106 may include body 1128, handle 1130, first drive rod 1132, second drive rod 1134, return spring 1136, drive plate 1138, set shaft 1140, washer springs 1142, button housing 1144, button latch 1146, button spring 1148, button 1150, and end cap 1152. Body 1128 may include first slot 1154 and second slot 1156 (as depicted in FIG. 47). First drive rod 1132 and return spring 1136 may be positioned within body 1128 of activation mechanism 1106. Handle 1130 may be coupled by pin 1158 to first slot 1154 (shown in FIG. 47) of body 1128 so that an end of the handle contacts an end of first drive rod 1132 (shown in FIG. 48). Second drive rod 1134 may be pivotally coupled to handle 1130 near a first end of second drive rod 1134 and pinned to second slot 1156 of body 1128 (shown in FIG. 51) near a second end of the second drive rod.

When handle 1130 is squeezed so that the handle moves from an initial position towards body 1128, end 1160 of the handle may contact end 1162 of first drive rod 1132 (shown in FIG. 51). The contact may extend first drive rod 1132 towards extender 1104 coupled to body 1128. End 1162 of first drive rod 1132 may contact and extend drive rod 1122 within extender 1104. Drive rod 1122 of extender 1104 may contact and extend drive rod 1110 of attachment portion 1102 of seater 1100. Return spring 1136 may return first drive rod 1132 to an initial position when handle 1130 is returned to an initial position. Similarly, return springs in attachment portion 1102 and extender 1126 may return drive rod 1110 in the attachment portion and drive rod 1122 of the extender to initial positions when the handle returns to an initial position. Connector engager 1112 may be coupled to drive rod 1110.

As depicted in FIG. 52, set shaft 1140 of a seater may thread into drive plate 1138. Drive plate 1138 may include spring support surface 1164 and spring support extension 1166. Set shaft 1140 may be threaded into spring support extension 1166 of drive plate 1138. Set shaft 1140 and drive plate 1138 may have ultrafine threading that allows for precise adjustment of a length of the set shaft that extends beyond top surface 1168 of the drive plate. A setscrew may be threaded into drive plate 1138 against an unthreaded portion of set shaft 1140. An end of the setscrew may press against set shaft 1140 to inhibit unwanted movement of the set shaft after the set shaft has been set to a desired position. Set shaft 1140 may include a drive tool slot that mates to a drive tool that rotates the set shaft. The drive tool may be a hex wrench, screwdriver, or other type of drive tool. The position of set shaft 1140 may be adjusted during calibration of the seater.

The position of set shaft 1140 may determine the amount of force that second drive rod 1134 needs to apply to drive plate 1138 to cause button 1150 to pop up through end cap 1152 (shown in FIG. 51 and FIG. 52). The amount of force needed to cause button 1150 to pop up through end cap 1152 may be substantially the same as the amount of force applied to an object that contacts the end of the first drive rod. As such, button 1150 may serve as an indicator when sufficient force is applied through the seater to the implant. Enough force may be applied to the connectors and an implant member to permanently lock and affix the connectors to the implant member as indicated when button 150 pops up through end cap 1152.

Belleville or conical washer springs 1142 may be placed over spring support extension 1166 and against spring support surface 1164 of drive plate 1138. Springs 1142 may include convex and concave sides. The convex and concave sides of springs 1142 may allow a stacked set of springs to axially compress or expand depending on a load applied to a top and bottom of a spring stack. In an embodiment of activation mechanism 1106, a convex side of first washer spring 1142 may be placed over spring support extension 1166 and against spring support surface 1164 of drive plate 1138. A concave side of second washer spring 1142 may then be placed over spring support extension 1166 and against the first washer spring. Remaining washer springs 1142 may be placed around set shaft 1140 in an alternating convex-concave pattern. In an embodiment, six washer springs 1142 are used. In other embodiments, fewer or more washer springs 1142 may be used. The convex-concave pattern allows for compression of washer springs 1142 during use so that end 1170 of set shaft 1140 may activate button trigger 1146 of the seater.

Assembled drive plate 1138, set shaft 1140, and set of washer springs 1142 may be placed in seater body 1128 against an end of second drive shaft 1134. Alternately, drive plate 1138, set shaft 1140, and set of washer springs 1142 may be individually positioned within the body against the end of second drive shaft 1134.

FIG. 52 shows a detailed view of an embodiment of an end of activation mechanism 1106. Button 1150, button spring 1148, and button latch 1146 may be coupled to button housing 1144. Button housing 1144 may be placed on top of washer springs 1142, and end cap 1152 may be threaded onto body 1128 to form assembled activation mechanism 1106. Button 1150 and button latch 1146 may have through openings that allow a drive tool to be inserted into set shaft 1140 of assembled activation mechanism 1106. A height that set shaft 1140 extends above drive plate 1138 may be adjusted with the drive tool without disassembling activation mechanism 1106.

Button latch 1146 may include arm 1172 and hook 1174 that engages surface 1176 of button 1150. Button latch 1146 may be pivotally coupled to button housing 1144. When the handle of activation mechanism 1106 moves towards body 1128 and a force is applied by end 1162 of first drive rod 1132 to an object, second drive rod 1134 applies an opposite force to drive plate 1138. The force applied to drive plate 1138 may move the drive plate toward button housing 1144 if the applied force is large enough to compress washer springs 1142. Button housing 1144 may be fixed in position by end cap 1152. The force applied to drive plate 1138 may contact end 1170 of set shaft 1140 against arm 1172 of button latch 1146. If the force applied to drive plate 1138 is large enough, end 1170 will move arm 1172 toward end cap 1152 and rotate hook 1174 away from button 1150 to release the button. Button spring 1148 may force a portion of button 1150 above top surface 1178 of end cap 1152.

To calibrate a seater, activation mechanism 1106 may be coupled to calibrator 1180. A calibrator is shown schematically in FIG. 53. In an embodiment, threading couples activation mechanism 1106 to calibrator 1180. In other embodiments, quick connects or other types of connectors may couple activation mechanism 1106 to calibrator 1180. Calibrator 1180 may include an internal force sensor. End 1162 of first drive rod 1132 (shown in FIG. 51) may contact the force sensor. A user may squeeze handle 1130 of activation mechanism 1106 until button 1150 pops up above top surface 1178 of end cap 1152. The user may observe the amount of force applied by the end to the sensor from display 1182. Display 1182 may be an analog indicator or a digital indicator (such as an LCD display). After button 1150 has popped up and handle 1130 has been returned to an initial position, the user may push the button downwards so that a latch hook engages a portion of the button. If the force needed to release button 1150 is too small, set shaft 1140 (shown in FIG. 52) may be threaded into drive plate 1138 to decrease a length of the set shaft so that more compression of springs 1142 is required before the contact between the set shaft and latch will release the button. If the force needed to release button 1150 is too large, set shaft 1140 may be threaded out of drive plate 1138 to increase the length of the set shaft so that less compression of springs 1142 is required before the contact between the set shaft and latch 1140 will release the button.

The length of set shaft 1140 that extends above drive plate 1138, shown in FIG. 52, may be adjusted by rotating the set shaft with a drive tool. The drive tool, which may be a hex wrench, may pass through button 1150 and latch 1140 without disassembly of the seater. After adjusting set shaft 1140, the user may squeeze the handle to determine the amount of force needed to release button 1150 at the new setting of set shaft 1140. The user may continue adjusting set shaft 1140 until a desired amount of force releases button 1150. The desired amount of force may directly correspond to an amount of force that needs to be applied to the connectors and implant members to affix the connectors to the implant members. When set shaft 1140 is positioned so that a proper amount of force releases button 1150 when the seater handle is squeezed, the position of the set shaft may be fixed by rotating a setscrew to drive the setscrew into drive plate 1138 and against the set shaft. The desired amount of force to couple connectors to an implant member may be between about 800 pounds and about 1200 pounds, or between about 900 pounds and about 1100 pounds, or about 1000 pounds. The activation mechanism may provide a thirty- to fifty-fold or greater mechanical advantage to a grip of a user.

An embodiment of a seater may include a pop-up button to indicate when sufficient force has been applied to couple a connector or connectors to an implant member. Other types of indicators may also be used instead of, or in conjunction with, a pop-up button. For example, an embodiment of a seater may include an indicator light that turns on when enough force is applied to affix a connector or connectors to an implant member. An embodiment of a seater may produce an audible noise when enough force is applied to affix a connector or connectors to an implant member. Other types of indicators may also be used.

Figure 54:
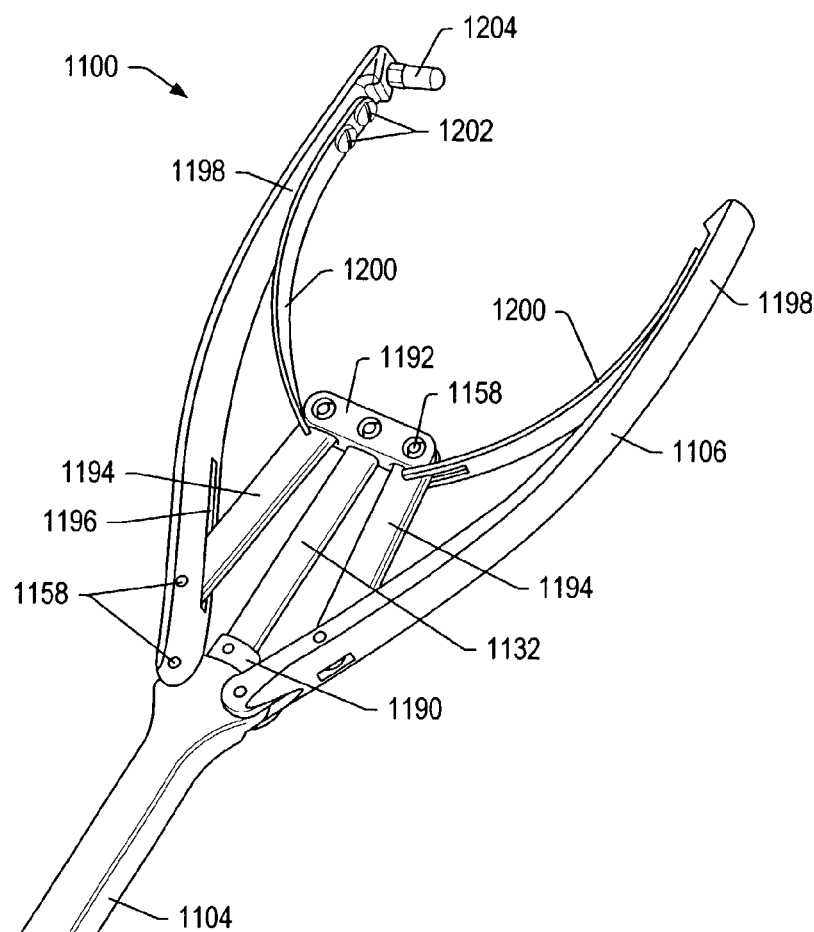
FIG. 54 shows a perspective view of an embodiment of a seater.
Figure 54:
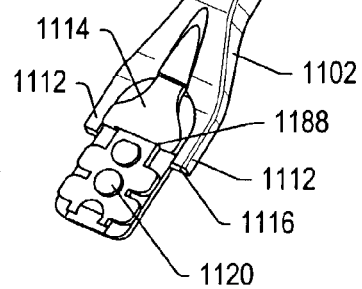

An alternate embodiment of a seater is depicted in FIG. 54. Plate engager 1114 of attachment portion 1102 may be attached to drive rod 1132 that extends through extender 1104 to activation mechanism 1106 of seater 1100. Engaging activation mechanism 1106 of seater 1100 may move drive rod 1132 from an initial position to a second position. When plate engager 1114 of seater 1100 is coupled to an implant member, applying force to activation mechanism 1106 may apply a force that retracts drive rod 1132. Drive rod 1132 may retract plate engager 1114 relative to stationary connector engager 1112. Ends 1116 of connector engager 1112 may apply a downward force against connectors in tapered slots of implant members as the implant members are moved upwards by plate engager 1114.

Connector engager 1112 of seater 1100 may have ends 1116 that press against the connectors positioned within the implant members. Connector engager 1112 may be sized to contact connectors that are spaced a set distance apart for a specific size of implant member. Connector engagers 1112 having various sizes corresponding to different sizes of implant members may be provided in an instrumentation set. The connector engagers may be modular components that attach to extender 1104 of seater 1100. In other embodiments, seaters may be integral units and complete seaters for each size of implant member included in an instrumentation set may be provided in the instrumentation set.

Member engager 1114 may be shaped to engage a recessed portion of an implant member. Member engager 1114 may include extensions 1120 that are placed within openings 28 of implant member 12 (shown in FIG. 2). Member engager 1114 may also include stop surface 1188. Stop surface 1188 may contact an anterior edge of an implant member to limit an insertion depth of member engager 1114 within the implant member. After member engager 1114 is coupled to an implant member, a retainer may be placed between a second implant member and a back surface of the member engager. The retainer may prevent unintentional removal of member engager 1114 from the implant member.

Drive rod 1132 of seater 1100 may be coupled to plate engager 1114 and extend through extender 1104 to activation mechanism 1106 of the seater. Drive rod 1132 may extend through collar 1190 proximate an opening at a top of extender 1104. Collar 1190 may limit a distance which drive rod 1132 extends through extender 1104 of the seater in an initial position.

Drive rod 1132 may be attached to activation mechanism 1106 through connection member 1192. Drive rod 1132 may be attached centrally using pins 1158 or may be welded to connection member 1192. A pair of connecting rods 1194 may be rotatably attached at an end using pins 1158, or other fastening means, to connection member 1192 on opposite sides of drive rod 1132. Opposite ends of connecting rods 1194 may be rotatably attached within slots 1196 proximate a base of a pair of grips 1198 of activation mechanism 1106.

The pair of grips 1198 may be shaped to be easily graspable by one hand of a surgeon. Grips 1198 may be rotatably attached to extender 1104 on opposite sides of collar 1190 and drive rod 1132 extending from the extender. FIG. 54 shows grips 1198 in an initial position. Spring members 1200 may bias grips 1198 to the initial position. An end of spring member 1200 may be affixed to an end of each of grips 1198 opposite extender 1104 of the seater with fasteners 1202. Fasteners may be, but are not limited to, screws, rivets, brads, and/or adhesive. The opposite end of each spring member 1200 may slidably engage an upper portion of connecting rod 1194 proximate connection member 1192.

The distal end of one of grips 1198 may include kiss pin 1204. Kiss pin 1204 may contact the distal end of other grip 1198 when the grips are squeezed together to a second position when activation mechanism 1106 of the seater is activated. Kiss pin 1204 may contact opposite grip 1198 when sufficient force is applied through the seater to the implant to permanently lock the connectors to the implant members. The seater may apply a force of approximately 2250 Newtons (N) to each connector to affix (or "cold weld") a connector within a tapered slot of an implant member to the implant member.

When grips 1198 are squeezed together to activate the seater, spring members 1200 may slide along connecting rods 1194 proximate connection member 1192. Connecting rods 1194 may rotate within slots 1196 proximate the base of grips 1198. An upper end of slots 1196 may inhibit further rotation of connecting rods 1194 when kiss pin 1204 on the end of one grip 1198 contacts the opposite grip. The ends of connecting rods 1194 rotatably attached to connection member 1192 may rotate and force the connection member upward. The upward force on connection member 1192 retracts drive rod 1132 attached centrally to the connection member through extender 1104 of the seater. As such, an implant member coupled to the end of drive rod 1132 at the attachment portion of the seater is forced upwards. Ends 1116 of connector engager 1112 may contact and apply an opposing force against the connectors in the tapered slots of the implant members as the implant member is retracted upward toward the extender. Sufficient force is applied through the seater to the implant to permanently lock and affix the connectors to the implant members.

Figure 55:
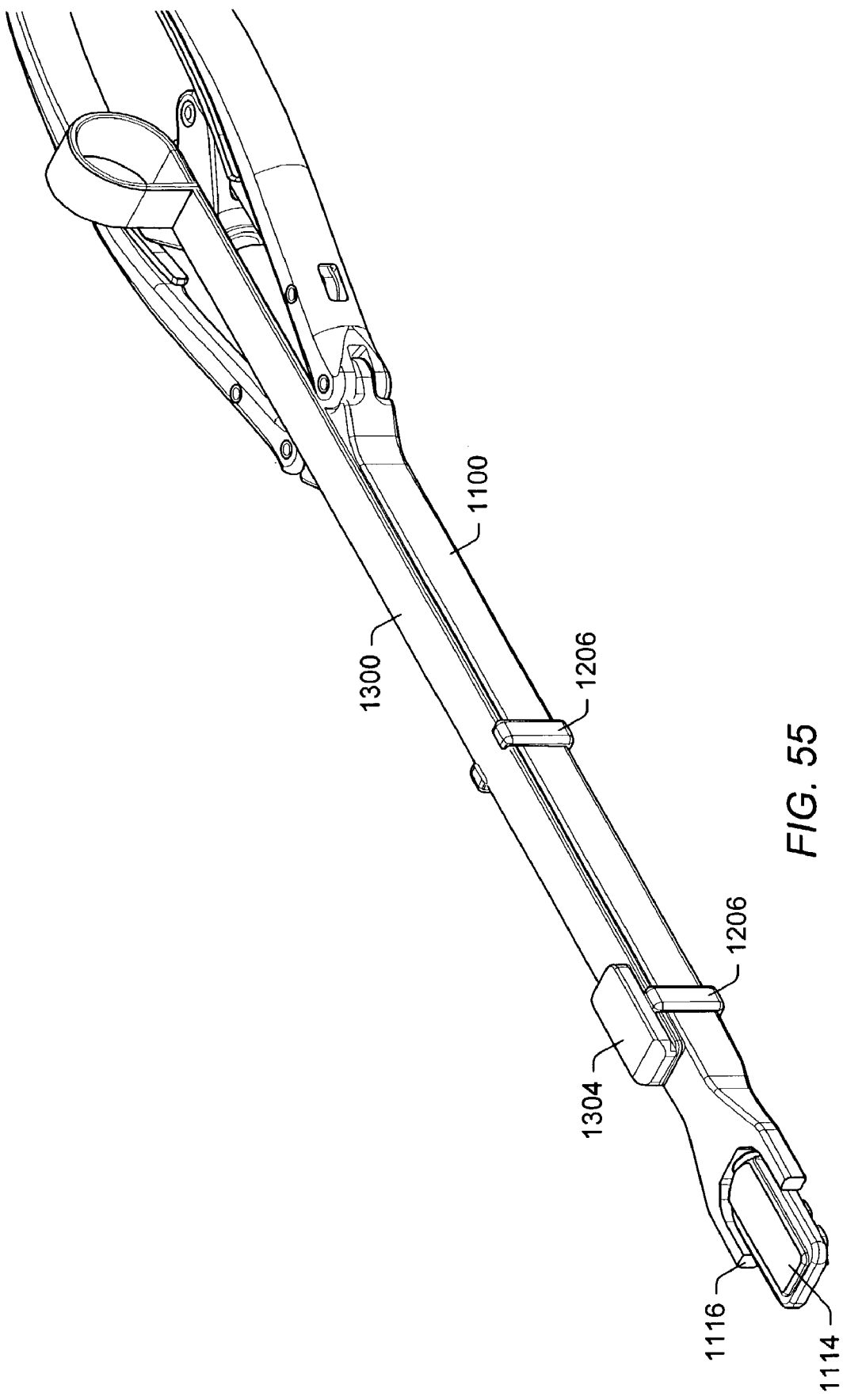
FIG. 55 shows a perspective view of a portion of a seater and retainer combination.

As shown in FIG. 55, seater 1100 may include retainer brackets 1206. Retainer brackets 1206 may be attached to extender 1104. Retainer 1300 may slide within retainer brackets 1206. Retainer brackets 1206 may allow retainer and seater to be joined together to facilitate handling of the retainer and seater during use. In some embodiments, spacer 1304 may include a tapered surface that facilitates insertion of the spacer in a space between implant members. In some embodiments, member engager 1114 of seater 1100 may include a stop that limits an insertion distance of spacer 1304 between implant members.

An instrumentation set may include the instruments and devices to form an implant in a spinal fusion procedure. A surgeon may perform a discectomy to remove a portion or all of disc 20 to form disc space 16 between adjacent vertebrae 18. A prepared disc space is shown in FIG. 3. Instruments such as curettes, rongeurs, and bone shavers may be used to prepare disc space 16 for the implant. Vertebral surfaces that will contact implant members 12 of implant 10 (shown in FIG. 1 and FIG. 2) may be cleaned of any cartilage or other tissue. The vertebral surfaces may be shaped to substantially conform to outer surfaces of implant members to be placed against the vertebral surfaces.

A width and depth spacer, such as width and depth spacer 100 depicted in FIG. 9, may be used to determine the proper width and depth of the disc space during the discectomy. Radiological images may be taken during the discectomy with spacer 100 positioned between the vertebrae to determine if disc material has been removed to form a disc space of the proper width and depth. A mark or marks may be scored or burned into a surface of a vertebra close to a center of an edge of the vertebra. The mark may be used as a reference mark to determine a proper lateral position of the implant and instrumentation during formation of the implant. The disc space may be centered laterally and transversely between adjacent vertebrae. When an implant is formed, 70% or more of each vertebral surface may contact implant members of the implant.

A height spacer, such as height spacer 200 depicted in FIG. 10, may be used to determine a height of an implant to be formed in the prepared disc space between vertebrae. Height spacer 200 may be attached to a slap hammer, such as slap hammer 900 depicted in FIG. 27. A proper height of an implant may correspond to the size of a height spacer that is positioned within the disc space with three or four impacts of slide 908 against a lower stop of slap hammer 900. The height spacer may be removed from the disc space by impacting slap hammer slide 908 against upper stop 910.

A pair of implant members may be selected depending on the size of the disc space created during the discectomy. Implant member or implant members 12 that include sloped surfaces 22 (depicted in FIG. 1) may be selected to provide lordotic correction for adjacent vertebrae, if necessary. If lordotic adjustment of the vertebrae is not needed, implant members 12 with 0° of lordotic adjustment may be selected. Connectors 14 may be selected depending on the height of the implant to be formed within the disc space.

Implant members may be attached to a spreader, such as spreader 400 depicted in FIG. 36. The implant members may be inserted into the prepared disc space. If needed, an impact cap may be placed on the spreader, and insertion guides may be placed in the disc space to facilitate insertion of the implant members into the disc space.

A separator, such as separator 300 depicted in FIG. 33, may be inserted into the spreader. Connectors may be positioned in side openings 328 prior to insertion of the separator into the spreader. Inserting the separator into the spreader may separate implant members attached to the spreader to a desired separation distance. During insertion of the separator into the spreader, protrusions of the implant members may enter into vertebral surfaces.

Depth gauges, such as depth gauge 800 depicted in FIG. 34, may be inserted into depth gauge passages in the separator. The depth gauges may dislodge the connectors from the side openings. The depth gauges may position the connectors in tapered slots of the implant members.

A slap hammer may be attached to the separator, as depicted in FIG. 46. The slap hammer may be used to remove the separator, spreader, and depth gauges from the patient. Implant members with connectors positioned in tapered slots of the implant members may be left in the disc space. Radiological images may be taken to ensure the implant members and connectors are laterally and transversely positioned properly before locking the connectors into place.

A connector seater, such as connector seater 1100 depicted in FIG. 54, may be coupled to a first implant member. A retainer may be positioned between a second implant member and the separator to inhibit separation of the seater from the first implant member. Grips of the seater may be squeezed until kiss pin on a first grip contacts a second grip. When the kiss pin contacts the second grip, the connectors are affixed to the first implant member. The retainer may be removed. The seater may be disengaged from the first implant member and may be attached to the second implant member. The retainer may be positioned between the first implant member and the seater to inhibit removal of the seater from the second implant member. Grips of the seater may be squeezed until the kiss pin on the first grip contacts the second grip. The retainer and the seater may be removed from the patient. The implant is formed in the patient.

An optional backing plate, such as backing plate 60 depicted in FIG. 8, may be sized and inserted into the implant. Backing plate 60 may be properly sized by cutting the backing plate along indentions 62. Backing plate 60 may be coupled to a positioning rod. In an embodiment, the positioning rod is a depth gauge. The positioning rod may be used to guide backing plate 60 between the implant members of the implant until tabs 64 of the backing plates engage end walls of the implant members, such as end walls 66 of implant members 12 depicted in FIG. 5.

A bone awl may be used to perforate the surfaces to initiate bleeding of adjacent vertebrae through openings 28 in implant members 12. Perforation of the surfaces may promote new bone growth. The space between implant members 12 and connectors 14 of implant 10 may be packed with bone growth material, such as bone growth material 26 depicted in FIG. 4. A covering, such as SURGICEL®, may be placed over the bone growth material to inhibit migration of bone growth material 26 from implant 10. The opening in the patient may be closed.

An advantage of forming an implant in a space between two bone portions, such as an implant between adjacent vertebrae, may be that the implant members of the implant distract the bone portions to a desired separation distance without excess distraction of the bone. Avoiding over-distraction may allow muscles and ligaments adjacent to the implant to hold the implant between the bone portions. The implant members of the implant may also include protrusions that enter into adjacent bone portions to hold the implant in place. Connectors that join the implant members together may be compressed when a compressive load is placed on the implant. The ability to compress the connectors may allow compressive force to be applied to bone growth material placed between the implant members. Applying compressive force to the bone growth material may promote bone growth that fuses the two portions of bone together.

An advantage of forming an implant using spreader embodiments and separator embodiments is that impaction applied to insert the implant may minimize scarring, deformation, and/or fracturing of bone surfaces to which the implant is coupled. Implant members may be positioned in a prepared space before distracting the bone portions.

An advantage of forming an implant using spreader embodiments and separator embodiments is that the insertion area needed for the instrumentation may be kept to a minimum. Force applied between a pair of spreader holders allows outer surfaces of implant members to distract adjacent bone portions. Using the outer surfaces of the implant members to distract the bone portions may eliminate a need to have a large surgical opening to allow for room to leverage the adjacent bone portions to provide a desired separation distance between the bone portions.

An advantage of forming an implant between bone segments using spreader embodiments and separator embodiments may be that insertion of instruments and implants may be performed above an incision in the patient. The ability to insert devices and instrumentation above the incision may allow better visibility, more efficient use of available working space, a shorter procedure time, and better placement control than inserting devices at the level of bone portions being worked on. Implants may be inserted during an anterior procedure, a lateral procedure, a posterior procedure, or other spinal fusion procedure. Inserting implants using an anterior procedure may advantageously minimize required bone removal and muscle retraction.

An advantage of forming an implant with certain spreader embodiments and separator embodiments is that locking pins may be used to couple implant members to the instrumentation during insertion of the implant members within a patient. The locking pins may attach the implant members to the spreader before the implant members are inserted into the patient. The locking pins may inhibit undesired separation of the implant members from the spreader. The locking pins may also serve as guides during insertion of the separator into the spreader.

An advantage of forming an implant with instrumentation embodiments is that the formed implant may be formed to a desired shape. For example, if the implant is a spinal implant, the implant members may have sloped surfaces so that the formed implant provides desired lordotic adjustment of adjacent vertebrae. Further advantages of using instrumentation to insert an implant may include that the instrumentation is sturdy, durable, lightweight, safe, simple, efficient, and reliable; yet the instrumentation may also be easy to manufacture and use.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An implant and instrument for surgical use, comprising:
   a modular implant, said modular implant comprising a first plate, a second plate, and a connector configured to connect the first plate to the second plate; and
   an instrument for implanting the modular implant to a disc space, said instrument comprising a spreader and a separator,
   wherein the spreader comprises a body with an opening, a first member holder extending from the opening, and a second member holder extending from the opening,
   wherein the first member holder of the spreader comprises a distal end and a proximal end, said distal end of said first member holder having a first sloped surface, wherein the second member holder of the spreader comprises a distal end and a proximal end, said distal end of said second member holder having a second sloped surface, wherein the separator comprises a distal end and a proximal end, said distal end of the separator comprising an arm, wherein the separator is insertable within the opening of the body for slidable translation between the first member holder and the second member holder, wherein the arm is configured to releasably engage the connector, and wherein when the first plate is slidably engaged to the first member holder and when the second plate is slidably engaged to the second member holder, the separator slidably translates in the opening of the spreader to deliver the connector to connect the first plate to the second plate.

2. The implant and instrument of claim 1, wherein the implant comprises two connectors, and wherein the distal end of the separator comprises two arms for holding the two connectors.

3. The implant and instrument of claim 1, wherein the connector establishes a separation distance between the first plate and the second plate.

4. The implant and instrument of claim 2, wherein the two connectors that couple to the first plate and the second plate form a modular spinal implant.

5. The implant and instrument of claim 4, wherein the modular implant has a height range from about 8 mm to about 24 mm.

6. The implant and instrument of claim 1, wherein the distal end of the first member holder comprises a slot, said slot causing the distal end of the first member holder to apply a force to the first plate to hold the first plate onto the first member holder.

7. The implant and instrument of claim 1, wherein the distal end of the first member holder comprises a stop, said stop limits insertion of the first plate onto the first member holder.

8. The implant and instrument of claim 1, wherein the first member holder comprises a compression member, said compression member configured to apply a force against a recess in the first plate to frictionally couple the implant member to the holder.

9. The implant and instrument of claim 1, wherein the spreader comprises a depth indicator to indicate an insertion depth into the disc space of the first plate and the second plate.

10. The implant and instrument of claim 1, wherein the first member holder and the second member holder are angled such that there is substantially no separation distance between ends of the holders coupled to the first plate and the second plate when the spreader is in an initial position.

11. The implant and instrument of claim 1, wherein the opening comprises a ledge to limit an insertion depth of the separator into the spreader.

12. The implant and instrument of claim 1, wherein the connector comprises an X-shaped body.

13. The implant and instrument of claim 1, wherein the connector comprises a limiter, said limiter configured to limit the compression of connector a predetermined amount.

14. The implant and instrument of claim 12, wherein the connector comprises a limiter positioned within the X-shaped body, said limiter configured to limit the compression of connector a predetermined amount.

15. The implant and instrument of claim 1, wherein the separator comprises a groove, said groove configured to guide the separator between the implant members coupled to the holders of the spreader.

16. The implant and instrument of claim 1, wherein the arm of the separator is configured to allow insertion of the connector in only one direction.

17. An implant and instrument for surgical use, comprising:
  a modular implant, said modular implant comprising a first plate, a second plate, and two connectors configured to connect the first plate to the second plate; and
  an instrument for implanting the modular implant to a disc space, said instrument comprising a spreader and a separator;
  wherein the spreader comprises a body with an opening, a first member holder extending from the opening, and a second member holder extending from the opening,
  wherein the first member holder of the spreader comprises a distal end and a proximal end, said distal end of said first member holder having a first sloped surface,
  wherein the second member holder of the spreader comprises a distal end and a proximal end, said distal end of said second member holder having a second sloped surface,
  wherein the separator comprises a distal end and a proximal end, said distal end of the separator comprising two arms,
  wherein the separator is insertable within the opening of the body for slidable translation between the first member holder and the second member holder,
  wherein the two arms are configured to releasably engage the two connectors, and
  wherein when the first plate is slidably engaged to the first member holder and when the second plate is slidably engaged to the second member holder, the separator slidably translates in the opening of the spreader to deliver the two connectors to connect the first plate to the second plate.

* * * * *